US009987241B2

(12) United States Patent
Harrison, Jr. et al.

(10) Patent No.: US 9,987,241 B2
(45) Date of Patent: Jun. 5, 2018

(54) ENZYME CONJUGATE AND PRODRUG CANCER THERAPY

(71) Applicant: The Board of Regents of the University of Oklahoma, Norman, OK (US)

(72) Inventors: Roger G. Harrison, Jr., Norman, OK (US); John J. Krais, Abington, PA (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 123 days.

(21) Appl. No.: 14/865,650

(22) Filed: Sep. 25, 2015

(65) Prior Publication Data

US 2016/0089350 A1 Mar. 31, 2016

Related U.S. Application Data

(60) Provisional application No. 62/055,264, filed on Sep. 25, 2014.

(51) Int. Cl.

| | |
|---|---|
| *A61K 39/385* | (2006.01) |
| *A61K 31/198* | (2006.01) |
| *A61K 38/51* | (2006.01) |
| *A61K 31/436* | (2006.01) |
| *A61K 31/664* | (2006.01) |
| *A61K 45/06* | (2006.01) |
| *A61K 31/675* | (2006.01) |
| *C12N 9/88* | (2006.01) |
| *A61K 47/66* | (2017.01) |

(52) U.S. Cl.
CPC .......... *A61K 31/198* (2013.01); *A61K 31/436* (2013.01); *A61K 31/664* (2013.01); *A61K 31/675* (2013.01); *A61K 38/51* (2013.01); *A61K 45/06* (2013.01); *A61K 47/67* (2017.08); *C12N 9/88* (2013.01); *C12Y 404/01001* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,473,646 A | 9/1984 | Guy et al. | |
| 5,091,308 A | 2/1992 | Klegerman et al. | |
| 5,126,134 A | 6/1992 | Heim et al. | |
| 5,382,657 A | 1/1995 | Karasiewicz et al. | |
| 5,679,350 A | 10/1997 | Jankun et al. | |
| 5,690,929 A | 11/1997 | Lishko et al. | |
| 5,715,835 A | 2/1998 | Lishko et al. | |
| 5,747,475 A | 5/1998 | Nordquist et al. | |
| 5,759,542 A | 6/1998 | Gurewich | |
| 5,766,897 A | 6/1998 | Braxton | |
| 5,767,298 A | 6/1998 | Daleke | |
| 5,888,506 A | 3/1999 | Tan | |
| 5,972,885 A | 10/1999 | Spira et al. | |
| 6,004,555 A | 12/1999 | Thorpe et al. | |
| 6,051,230 A | 4/2000 | Thorpe et al. | |
| 6,093,399 A | 7/2000 | Thorpe et al. | |
| 6,132,729 A | 10/2000 | Thorpe et al. | |
| 6,156,321 A | 12/2000 | Thorpe et al. | |
| 6,165,509 A | 12/2000 | Hoffman et al. | |
| 6,177,087 B1 | 1/2001 | Greenwald et al. | |
| 6,217,869 B1 | 4/2001 | Meyer et al. | |
| 6,231,854 B1 | 5/2001 | Yuying | |
| 6,312,694 B1 | 11/2001 | Thorpe et al. | |
| 6,319,702 B1 | 11/2001 | Smith et al. | |
| 6,406,693 B1 | 6/2002 | Thorpe et al. | |
| 6,451,312 B1 | 9/2002 | Thorpe | |
| 6,491,894 B1 | 12/2002 | Ruoslahti et al. | |
| 6,528,481 B1 | 3/2003 | Burg et al. | |
| 6,576,239 B1 | 6/2003 | Rouslahti et al. | |
| 6,610,651 B1 | 8/2003 | Rouslahti et al. | |
| 6,749,853 B1 | 6/2004 | Thorpe et al. | |
| 6,783,760 B1 | 8/2004 | Thorpe et al. | |
| 6,818,213 B1 | 11/2004 | Thorpe et al. | |
| 6,933,281 B2 | 8/2005 | Rouslahti et al. | |
| 7,067,109 B1 | 6/2006 | Thorpe et al. | |
| 7,504,397 B2 | 3/2009 | Hummersone et al. | |
| 7,652,033 B2 | 1/2010 | Van Meir et al. | |
| 8,143,228 B2 | 3/2012 | Mabjeesh | |
| 8,168,603 B2 | 5/2012 | Jing et al. | |
| 8,394,799 B2 | 3/2013 | Lee et al. | |
| 8,507,492 B2 | 8/2013 | Perrin-Ninkovic et al. | |
| 8,557,814 B2 | 10/2013 | Castelhano et al. | |
| 8,691,866 B2 | 4/2014 | Iliopoulos et al. | |
| 8,709,407 B2 | 4/2014 | Georgiou et al. | |

(Continued)

FOREIGN PATENT DOCUMENTS

WO 9517908 7/1995

OTHER PUBLICATIONS

Burgess et al. (J. Cell Biol. 111:2129-2138, 1990).*
Lazar et al. ( Mol. Cell Biol. 8:1247-1252, 1998).*
Yuan et al (Journal of Hematology & Oncology, 2009, 2(45): 1-12).*
Hsu; "Tissue Culture Methods and Applications"; Kruse and Patterson, Eds, Academic Press, NY, (1973), pp. 764-767.
Halpern, B.C., et al.; "The Effect of Replacement of Methionine by Homocystine on Survival of Malignant and Normal Adult Mammalian Cells in Culture"; Proc. Nat. Acad. Sci. USA; (1974), vol. 71, No. 4, pp. 1133-1136.
Embleton, et al.; "Monoclonal Antibodies to Osteogeni Sarcoma Antigens" Immunology Series; (1984), vol. 23, pp. 181-207.
Marquardt, H., et al.; "Rat Transforming Growth Factor Type I: Structure and Relation to Epidermal Growth Factor"; Science, (1984), vol. 223, No. 4640, pp. 1979-1082.

(Continued)

*Primary Examiner* — Sean E Aeder
(74) *Attorney, Agent, or Firm* — Dunlap Codding, P.C.

(57) ABSTRACT

A method and composition for treating a cancerous tumor in a subject by targeting the tumor's vasculature using an enzyme conjugate comprising a ligand which binds to endothelial cells in the tumor vasculature and converts a prodrug administered to the subject into an anticancer drug in the tumor vasculature.

11 Claims, 20 Drawing Sheets
(3 of 20 Drawing Sheet(s) Filed in Color)

(56) References Cited

U.S. PATENT DOCUMENTS

| | | | |
|---|---|---|---|
| 8,906,374 B2 | 12/2014 | Kim et al. | |
| 8,940,936 B2 | 1/2015 | Lee et al. | |
| 8,962,577 B2 | 2/2015 | Hanes et al. | |
| 8,986,701 B2 | 3/2015 | Harrison | |
| 9,040,574 B2 | 5/2015 | Wang et al. | |
| 9,062,072 B2 | 6/2015 | Van Meir et al. | |
| 2002/0150984 A1 | 10/2002 | Mochly-Rosen et al. | |
| 2003/0045496 A1 | 3/2003 | Miki et al. | |
| 2004/0170620 A1 | 9/2004 | Thorpe et al. | |
| 2006/0028584 A1 | 11/2006 | Lind et al. | |
| 2006/0275371 A1 | 12/2006 | Dai et al. | |
| 2011/0002978 A1* | 1/2011 | Harrison | A61K 38/51 424/450 |
| 2011/0200576 A1* | 8/2011 | Georgiou | C12N 9/88 424/94.5 |
| 2013/0323284 A1 | 12/2013 | Alonso | |

OTHER PUBLICATIONS

Stoppelli, M.P., et al.; "Differentiation-Enhanced Binding of the Amino-Terminal Fragment of Human Urokinase Plasminogen Activator to a Specific Receptor on U937 Monocytes"; Proc. Natl. Acad. Sci. USA; (1985), vol. 82, pp. 4939-4943.
Appella, E., et al.; "The Receptor-Binding Sequence of Urokinase"; J. Biol. Chem.; (1987), vol. 262, No. 10, pp. 4437-4440.
Kimmel, et al.; "In vitro drug sensitivity testing in human gliomas"; J. Neurosurg.; (1987), vol. 66, pp. 161-171.
Muraguchi, A., et al.; "The Essential Role of B Cell Stimulatory Factor 2 (BSF-2/IL-6) for the Terminal Differentiation of B Cells"; J. Exp. Med.; (1988), vol. 167, pp. 332-344.
Argos, Patrick; "An Investigation of Oligopeptides Linking Domains in Protein Tertiary Structures and Possible Candidates for General Gene Fusion"; J. Mol. Biol.; (1990), vol. 211, pp. 943-958; see figure 2, p. 950.
Chen, L., et al.; "IL-6 Receptors and Sensitivity to Growth Inhibition by IL-6 in Clones of Human Breast Carcinoma Cells"; J. Biol. Regul. Homeost. Agents; (1991), vol. 5, No. 4, pp. 125-136.
Prior, T.I., et al.; "Cytotoxic Activity of a Recombinant Fusion Protein Between Insulin-Like Growth Factor I and Pseudomonas Exotoxin"; Cancer Res.; (1991), vol. 51, pp. 174-180.
Utsugi, et al.; "Elevated Expression of Phosphatidylserine in the Outer Membrane Leaflet of Human Tumor Cells and Recognition by Activated Human Blood Monocytes"; Cancer Res.; (1991), vol. 51, No. 11, pp. 3062-3066.
Boon, Thierry; "Toward a Genetic Analysis of Tumor Rejection Antigens"; Ludwig Institute for Cancer Research; (1992), vol. 58, pp. 177-210.
Rao, et al.; "Binding of Annexin V to a Human Ovarian Carcinoma Cell Line" (OC-2008). Contrasting Effects on Cell Surface Factor VIIa/Tissue Factor Activity and Prothrombinase Activity; Thromb Res.; (1992), vol. 67, No. 5, pp. 517-531.
Pastan, I., et al.; "Recombinant Toxins as Novel Therapeutic Agents"; Annu. Rev. Biochem.; (1992), vol. 61, pp. 331-354. Abstract only.
Drexler, Hans G.; "Recent Results on the Biology of Hodgkin and Reed-Sternberg Cells"; Leukemia and Lymphoma; (1993), vol. 9, pp. 1-25.
Abbaszadegan, et al.; "Analysis of Multidrug Resistance-associated Protein (MRP) Messenger RNA in Normal and Malignant Hematopoietic Cells"; Cancer Res.; (1994), vol. 54, pp. 4676-4679.
Dermer, Gerald D. "Another Anniversary for the War on Cancer"; Bio/Technology; (1994), vol. 12, p. 320.
Phillips, et al.; "Transforming Growth Factor-α-Pseudomonas Exotoxin Fusion Protein (TGF-α-PE38) Treatment of Subcutaneous and Intracranial Human Glioma and Medulloblastoma Xenografts in Athymic Mice1"; American Association for Cancer Research.; (1993), vol. 54, pp. 1008-1015.
Stanton, et al.; "Epidermal growth factor receptor expression by human squamous cell carcinomas of the head and neck, cell lines and xenografts"; Br. J. Cancer; (1994), vol. 70, pp. 427-433.

Kobayashi, et al.; "Inhibitory Effect of a Conjugate between Human Urokinase and Urinary Trypsin Inhibitor onTumore Cell Invasion in Vitro"; J. Biol. Chem.; (1995), vol. 270, No. 14, pp. 8361-8366.
Tait, et al.; "Prourokinase-Annexin V Chimeras, Construction, Expression, and Characterization of Recombinant Proteins"; The Journal of Biological Chemistry; (1995), vol. 270, No. 37, pp. 21594-21599.
Tan, et al.; "Serum Methionine Depletion without Side Effects by Methioninase in Metastatic Breast Cancer Patients"; Anticancer Research; (1996), vol. 16, pp. 3937-3942.
Kokkinakis, D.M., et al.; "Regulation of O6-methylguanine-DNA methyltransferase by methionine in human tumor Cells"; British Journal of Cancer; (1997), vol. 75, pp. 779-788, Abstract only.
Tan, et al.; "Recombinant Methioninase Infusion Reduces the Biochemical Endpoint of Serum Methionine with Minimal Toxicity in High-Stage Cancer Patients"; Anticancer Research; (1997), vol. 17, pp. 3857-3860.
Gooch, J.L., et al.; "Interleukin 4 Inhibits Growth and Induces Apoptosis in Human Breast Cancer Cells"; American Association for Cancer Research; (1998), vol. 58, pp. 4199-4205.
Tan, et al.; "Polyethylene Glycol Conjugation of Recombinant Methioninase for Cancer Therapy"; Protein Expression and Purification; (1998), vol. 12, pp. 45-52.
Iehlé, C., et al.; "Differences in steroid 5α-reductase iso-enzymes expression between normal and pathological human prostate tissue"; J. Steroid Biochem. Mol. Biol.; (1999), vol. 68, pp. 189-195.
Bodey, et al.; "Failure of Cancer Vaccines: the Significant Limitations of this Approach to Immunotherapy"; Anticancer Res.; (2000), vol. 20, pp. 2665-2676.
Kunkel, P., et al.; "Expression and localizationof scatter factor/ hepatocyte growth factor in human astrocytomas"; Neuro-Oncology; (2001), vol. 3, No. 2, pp. 82-88.
Taylor, et al.; "A Phase I and Pharmacodynamic Evaluation of Polyethylene Gloycol-Conjugated L-Asparaginase in Patients with Advanced Solid Tumors"; Cancer Chemother. Pharmacol; (2001), vol. 47, pp. 83-88.
Ran, et al.; "Phosphatidylserine is a Marker of Tumor Vasculature and a Potential Target for Cancer Imaging and Therapy"; Int. J. Radiation Oncology Biol. Phys.; (2002), vol. 54, No. 5, pp. 1479-1484.
Ran, et al.; "Increased Exposure of Anionic Phospholipids on the Surface of Tumor Blood Vessels"; Cancer Res. (2002), vol. 62, pp. 6132-6140.
Yang, et al.; "Enhancing the Anticoagulant Potency of Soluble Tissue Factor Mutants by Increasing their Affinity to Factor VIIa"; Thromb Haemost, (2002), vol. 87, pp. 450-458.
Zaslav, A.L., et al.; "Significance of a Prenatally Diagnosed del(10)(q23)"; Amer. J. Medical Genetics; (2002), vol. 107, pp. 174-176.
Peron, et al.; "Targeting of a Novel Fusion Protein Containing Methioninase to the Urokinase Receptor to Inhibit Breast Cancer Cell Migration and Proliferation"; Cancer Chemother. Pharmacol.; (2003), vol. 52, pp. 270-276.
Van Dyke, D.L., et al.; "Monosomy 21 in hematologic deseases"; Cancer Genetics and Cytogenetics; (2003), vol. 142, pp. 137-141.
Pento, et al.; "Influence of a Methioninase Containing Fusion Protein Targeted to the Urokinase Receptors on Breast Cancer Metastasis in Nude Mouse Xenografts"; AACR Conference "Frontiers in Cancer Prevention Research"; Seattle, WA; Oct. 2004.
Tian, J., et al.; "The expression of native and cultured RPE grown on different matrices"; Physiol Genomics; (2001), vol. 17, pp. 170-182.
Zips, et al.; "New Anticancer Agents: In Vitro and In Vivo Evaluation"; In vivo; (2005), vol. 19, pp. 1-8.
Zang, et al.; "Internalizing Versus Non-internalizing Receptors for Targeting L-Methioninase to Cancer Cells"; American Journal of Pharmacology and Toxicology; (2006), vol. 1, No. 3, pp. 60-64.
Kaiser, Jocelyn; "First Pass at Cancer Genome Reveals Complex Landscape"; Science; (2006), vol. 313, p. 1370.
Mellman, Ira.; "Where Next for Cancer Immunotherapy"; The Scientist; (2006), vol. 20, No. 1, pp. 177-210.

(56) References Cited

OTHER PUBLICATIONS

Kenis, et al.; "Annexin A5: shifting from a diagnostic towards a therapeutic realm"; Cell. Mol. Life Sci.; (2007), vol. 64, pp. 2859-2862.
Dumler, et al.; "Urokinase Activates the Jak/Stat Signal Trasduction Pathway in Human Vascular Endothelial Cells", Aarterioscler Thromb Vasc Biol (1999), vol. 19, pp. 290-297.
Jafferali, S., et al.; "Insulin-Like Growth Factor-I and Its Receptor in the Frontal cortex, Hippocampus, and Cerebellum of Normal Human and Alzheimer Disease Brains"; Synapse (2000), vol. 38, pp. 450-459.
Krais, et al.; "Antitumor Synergism and Enhanced Survival with a Tumor Vasculature—Targeted Enzyme Prodrug System, Rapamycin, and Cyclophosphamide," American Association for Cancer Research Molecular Cancer Therapeutics (2017), pp. 1-11.
Krais, et al.; "Antitumor Synergism and Enhanced Survival with a Tumor Vasculature—Targeted Enzyme Prodrug System, Rapamycin, and Cyclophosphamide, Supplementary Data" American Association for Cancer Research Molecular Cancer Therapeutics (2017), pp. 1-11.
Dutcher, Janice P.; "Mammalian Target of Rapamycin (mTOR) Inhibitors," Current Oncology Reports (2004), vol. 6, pp. 111-115.
Zaytseva, et al.; "mTOR Inhibitors in Cancer Therapy," Cancer Letters (2012), vol. 319, pp. 1-7.
Gerke, et al.; "Annexins: From Structure to Function," Physiol Rev (2002), vol. 82, pp. 331-371.
Azuma, et al.; "Development of Immunoadjuvants for Immunotherapy of Cancer," International Immunopharmacology (2001), vol. 1, pp. 1249-1259.
Deonarain, et al.; "Targeting Enzymes for Cancer Therapy: Old Enzymes in New Roles," Br J. Cancer (1994), vol. 70, pp. 786-794.
Dredge, et al.; "Adjuvants and the promotion of Th1-type Cytokines in Tumour Immunotherapy," Cancer Immunol Immunother (2002), vol. 51, pp. 521-531.
Hahn, et al.; "Thermochemotherapy: Synergism Between Hyperthermia (42-43°) and Adriamycin (or Bleomycin) in Mammalian Cell Inactivation." Proc. Nat. Acad. Sci. (1975), vol. 72, No. 3, pp. 937-940.
Hurwitz, et al.; "Combination Immunotherapy of Primary Prostate Cancer in a Transgenic Mouse Model Using CTLA-4 Blockadel," Cancer Research (2000), vol. 60, pp. 2444-2448.
Naylor, et al.; "In situ Photoimmunotherapy: a Tumour-directed Treatment for Melanoma," British Journal of Dermatology (2006), vol. 155, pp. 1287-1292.
Peng, et al.; "PD-1 Blockade Enhances T Cell Migration to Tumors by Elevating IFN-$\gamma$ Inducible Chemokines," Cancer Research (2012), vol. 72, No. 20, pp. 5209-5218.
Stagg, et al.; Anti-CD73 Antibody Therapy Inhibits Breast Tumor Growth and Metastasis, PNAS (2010), vol. 107, No. 4, pp. 1547-1552.
Storm, FK; "Clinial Hyperthermia and Chemotherapy," Radiol Clin North Am. (1989), vol. 27, No. 3, pp. 621-627.
van der Zee, J.; Heating the Patient: a Promising Approach?, Annals of Oncology (2002), vol. 13, pp. 1173-1184.
Weiss, et al.; "Immunotherapy of Cancer by IL-12-based Cytokine Combinations," Expert Opin Biol Ther. (2007), vol. 7, No. 11, pp. 1705-1721.

* cited by examiner

MQKDASLSGFLPSFQHFATQAIHVGQEPEQWNSRAVVLPISLATTFKQDF    50

PGQSSGFNYSRSGNPTRNCLEKAVAALDGAKHSLAFASGLAATITITHLL    100

KAGDEIICMDEVYGGTNLYFRRVASEFGLKISFVDCSKTKLLEAAITPQT    150

KLVWIETPTNPTLKLADIGACAQIVHKRGDIILVVDNTFMSAYFQRPLAL    200

GADICMCSATKYMNGHSDVVMGLVSVNSDDLNSRLRFLQNSLGAVPSPFD    250

CYLCCRGLKTLQVRMEKHFKNGMAVARFLETNPRVEKVVYPGLPSHPQHE    300

LAKRQCSGCPGMVSFYIKGALQHAKAFLKNLKLFTLAVSLGGYESLAELP    350

AIMTHASVPEKDRATLGINDTLIRLSVGLEDEQDLLEDLDRALKAAHP    398

FIG. 17

MQEKDASSQGFLPHFQHFATQAIHVGQDPEQWTSRAVVPPISLSTTFKQG 50

APGQHSGFEYSRSGNPTRNCLEKAVAALDGAKYCLAFASGLAATVTITHL 100

LKAGDQIICMDDVYGGTNRYFRQVASEFGLKISFVDCSKIKLLEAAITPE 150

TKLVWIETPTNPTQKVIDIEGCAHIVHKHGDIILVVDNTFMSPYFQRPLA 200

LGADISMYSATKYMNGHSDVVMGLVSVNCESLHNRLRFLQNSLGAVPSPI 250

DCYLCNRGLKTLHVRMEKHFKNGMAVAQFLESNPWVEKVIYPGLPSHPQH 300

ELVKRQCTGCTGMVTFYIKGTLQHAEIFLKNLKLFTLAESLGGFESLAEL 350

PAIMTHASVLKNDRDVLGISDTLIRLSVGLEDEEDLLEDLDQALKAAHPP 400

SGSHS 405

FIG. 18

MATRGTVTDFPGFDGRADAEVLRKAMKGLGTDEDSILNLLTSRSNAQRQEIAQEFKTLF
GRDLVDDLKSELTGKFEKLIVAMMKPSRLYDAYELKHALKGAGTDEKVLTEIIASRTPE
ELSAIKQVYEEEYGSNLEDDVVGDTSGYYQRMLVVLLQANRDPDTAIDDAQVELDAQA
LFQAGELKWGTDEEKFITIFGTRSVSHLRRVFDKYMTISGFQIEETIDRETSGNLEQLLLA
VVKSIRSIPAYLAETLYYAMKGAGTDDHTLIRVVVSRSEIDLFNIRKEFRKNFATSLYSMI
KGDTSGDYKKALLLLCGGEDD

FIG. 19

MAMVSEFLKQARFLENQEQEYVQAVKSYKGGPGSAVSPYPSFNVSSDVAALHKAIMV
KGVDEATIIDILTKRTNAQRQQIKAAYLQENGKPLDEVLRKALTGHLEEVVLAMLKTPA
QFDADELRGAMKGLGTDEDTLIEILTTRSNEQIREINRVYREELKRDLAKDITSDTSGDFR
KALLALAKGDRCQDLSVNQDLADTDARALYEAGERRKGTDVNVFTTILTSRSFPHLRR
VFQNYGKYSQHDMNKALDLELKGDIEKCLTTIVKCATSTPAFFAEKLYEAMKGAGTRH
KALIRIMVSRSEIDMNEIKVFYQKKYGISLCQAILDETKGDYEKILVALCGGN

FIG. 20

MHHHHHHHHSSGLVPRGSGMKETAAAKFERQHMDSPDLGTDDDDKMLEVLFQGPMQK
DASLSGFLPSFQHFATQAIHVGQEPEQWNSRAVVLPISLATTFKQDFPGQSSGFNYS
RSGNPTRNCLEKAVAALDGAKHSLAFASGLAATITITHLLKAGDEHCMDEVYGGT
NLYFRRVASEFGLKISFVDCSKTKLLEAAITPQTKLVWIETPTNPTLKLADIGACAQI
VHKRGDIILVVDNTFMSAYFQRPLALGADICMCSATKYMNGHSDVVMGLVSVNSD
DLNSRLRFLQNSLGAVPSPFDCYLCCRGLKTLQVRMEKHFKNGMAVARFLETNPR
VEKVVYPGLPSHPQHELAKRQCSGCPGMVSFYIKGALQHAKAFLKNLKLFTLAVS
LGGYESLAELPAIMTHASVPEKDRATLGINDTLIRLSVGLEDEQDLLEDLDRALKA
AHP<u>SGGGGSGGGG</u>*MATRGTVTDFPGFDGRADAEVLRKAMKGLGTDEDSILNLLTSRSNAQ*
*RQEIAQEFKTLFGRDLVDDLKSELTGKFEKLIVAMMKPSRLYDAYELKHALKGAGTDEKVLT*
*EIIASRTPEELSAIKQVYEEEYGSNLEDDVVGDTSGYYQRMLVVLLQANRDPDTAIDDAQVELD*
*AQALFQAGELKWGTDEEKFITIFGTRSVSHLRRVFDKYMTISGFQIEETIDRETSGNLEQLLLA*
*VVKSIRSIPAYLAETLYYAMKGAGTDDHTLIRVVVSRSEIDLFNIRKEFRKNFATSLYSMIKGDTS*
*GDYKKALLLLCGGEDD*

Legend: 6X His Tag, HRV-3C protease site, mCGL, <u>linker</u>, *AV*

FIG. 21

MHHHHHHHHSSGLVPRGSGMKETAAAKFERQHMDSPDLGTDDDDKMLEVLFQGPMQK
DASLSGFLPSFQHFATQAIHVGQEPEQWNSRAVVLPISLATTFKQDFPGQSSGFNYS
RSGNPTRNCLEKAVAALDGAKHSLAFASGLAATITITHLLKAGDEHCMDEVYGGT
NLYFRRVASEFGLKISFVDCSKTKLLEAAITPQTKLVWIETPTNPTLKLADIGACAQI
VHKRGDIILVVDNTFMSAYFQRPLALGADICMCSATKYMNGHSDVVMGLVSVNSD
DLNSRLRFLQNSLGAVPSPFDCYLCCRGLKTLQVRMEKHFKNGMAVARFLETNPR
VEKVVYPGLPSHPQHELAKRQCSGCPGMVSFYIKGALQHAKAFLKNLKLFTLAVS
LGGYESLAELPAIMTHASVPEKDRATLGINDTLIRLSVGLEDEQDLLEDLDRALKA
AHP<u>SGGGGSGGGG</u>*MAMVSEFLKQARFLENQEQEYVQAVKSYKGGPGSAVSPYPSFNVSSDV*
*AALHKAIMVKGVDEATIIDILTKRTNAQRQQIKAAYLQENGKPLDEVLRKALTGHLEEVVLAM*
*LKTPAQFDADELRGAMKGLGTDEDTLIEILTTRSNEQIREINRVYREELKRDLAKDITSDTSGD*
*FRKALLALAKGDRCQDLSVNQDLADTDARALYEAGERRKGTDVNVFTTILTSRSFPHLRRVFQ*
*NYGKYSQHDMNKALDLELKGDIEKCLTTIVKCATSTPAFFAEKLYEAMKGAGTRHKALIRIMV*
*SRSEIDMNEIKVFYQKKYGISLCQAILDETKGDYEKILVALCGGN*

Legend: 6X His Tag, HRV-3C protease site, mCGL, <u>linker</u>, *AI*

FIG. 22

GPMQKDASLSGFLPSFQHFATQAIHVGQEPEQWNSRAVVLPISLATTFKQDFPGQSS
GFNYSRSGNPTRNCLEKAVAALDGAKHSLAFASGLAATITITHLLKAGDEHCMDEV
YGGTNLYFRRVASEFGLKISFVDCSKTKLLEAAITPQTKLVWIETPTNPTLKLADIG
ACAQIVHKRGDIILVVDNTFMSAYFQRPLALGADICMCSATKYMNGHSDVVMGLV
SVNSDDLNSRLRFLQNSLGAVPSPFDCYLCCRGLKTLQVRMEKHFKNGMAVARFL
ETNPRVEKVVYPGLPSHPQHELAKRQCSGCPGMVSFYIKGALQHAKAFLKNLKLF
TLAVSLGGYESLAELPAIMTHASVPEKDRATLGINDTLIRLSVGLEDEQDLLEDLDR
ALKAAHP<u>SGGGGSGGGG</u>*MATRGTVTDFPGFDGRADAEVLRKAMKGLGTDEDSILNLLTSR
SNAQRQEIAQEFKTLFGRDLVDDLKSELTGKFEKLIVAMMKPSRLYDAYELKHALKGAGTDE
KVLTEIIASRTPEELSAIKQVYEEEYGSNLEDDVVGDTSGYYQRMLVVLLQANRDPDTAIDDAQ
VELDAQALFQAGELKWGTDEEKFITIFGTRSVSHLRRVFDKYMTISGFQIEETIDRETSGNLEQ
LLLAVVKSIRSIPAYLAETLYYAMKGAGTDDHTLIRVVVSRSEIDLFNIRKEFRKNFATSLYSMIK
GDTSGDYKKALLLLCGGEDD*

Legend: mCGL, <u>linker</u>, *AV*

FIG. 23

GPMQKDASLSGFLPSFQHFATQAIHVGQEPEQWNSRAVVLPISLATTFKQDFPGQSS
GFNYSRSGNPTRNCLEKAVAALDGAKHSLAFASGLAATITITHLLKAGDEHCMDEV
YGGTNLYFRRVASEFGLKISFVDCSKTKLLEAAITPQTKLVWIETPTNPTLKLADIG
ACAQIVHKRGDIILVVDNTFMSAYFQRPLALGADICMCSATKYMNGHSDVVMGLV
SVNSDDLNSRLRFLQNSLGAVPSPFDCYLCCRGLKTLQVRMEKHFKNGMAVARFL
ETNPRVEKVVYPGLPSHPQHELAKRQCSGCPGMVSFYIKGALQHAKAFLKNLKLF
TLAVSLGGYESLAELPAIMTHASVPEKDRATLGINDTLIRLSVGLEDEQDLLEDLDR
ALKAAHP<u>SGGGGSGGGG</u>*MAMVSEFLKQARFLENQEQEYVQAVKSYKGGPGSAVSPYPSFN
VSSDVAALHKAIMVKGVDEATIIDILTKRTNAQRQQIKAAYLQENGKPLDEVLRKALTGHLEEV
VLAMLKTPAQFDADELRGAMKGLGTDEDTLIEILTTRSNEQIREINRVYREELKRDLAKDITSD
TSGDFRKALLALAKGDRCQDLSVNQDLADTDARALYEAGERRKGTDVNVFTTILTSRSFPHLR
RVFQNYGKYSQHDMNKALDLELKGDIEKCLTTIVKCATSTPAFFAEKLYEAMKGAGTRHKAL
IRIMVSRSEIDMNEIKVFYQKKYGISLCQAILDETKGDYEKILVALCGGN*

Legend: mCGL, <u>linker</u>, *AI*

FIG. 24

ATGCACCATCATCATCATCATTCTTCTGGTCTGGTGCCACGCGGTTCTGGTATGAAA
GAAACCGCTGCTGCTAAATTCGAACGCCAGCACATGGACAGCCCAGATCTGGGTAC
CGATGACGACGACAAGATGCTGGAAGTTCTGTTCCAGGGTCCGATGCAGAAAGACG
CGAGCCTGTCTGGCTTCCTGCCGTCTTTTCAGCACTTCGCAACTCAGGCGATCCACGT
TGGTCAGGAGCCTGAACAATGGAACTCTCGTGCGGTTGTTCTGCCGATCAGCCTCGC
CACGACCTTCAAACAGGATTTCCCGGGTCAGTCTTCTGGTTTCAACTACTCCCGTTCT
GGCAATCCGACCCGTAACTGCCTGGAAAAAGCGGTAGCCGCGCTGGACGGTGCGAA
ACACTCTCTGGCGTTCGCCTCTGGTCTCGCGGCGACCATCACGATCACCCATCTGCT
CAAGGCCGGTGACGAAATCATCTGTATGGACGAAGTTTACGGTGGCACCAACCTGT
ATTTTCGTCGTGTTGCGTCTGAATTCGGTCTGAAAATCTCTTTCGTTGACTGCTCTAA
AACCAAACTCCTGGAGGCAGCAATTACTCCGCAGACGAAACTCGTTTGGATCGAAA
CCCCGACCAACCCGACCCTGAAGCTCGCCGACATCGGTGCGTGCGCTCAAATCGTTC
ACAAACGTGGTGACATCATCCTGGTTGTTGATAATACCTTCATGTCTGCGTACTTTCA
GCGTCCGCTGGCGCTGGGCGCTGACATCTGCATGTGCTCCGCGACCAAATACATGAA
CGGTCACTCTGACGTAGTTATGGGTCTGGTTAGCGTTAACAGCGACGATCTCAATTC
CCGCCTGCGTTTCCTGCAGAACTCCCTCGGCGCAGTACCGTCCCCGTTCGACTGCTA
TCTCTGCTGCCGTGGTCTCAAAACGCTGCAGGTTCGTATGGAAAAGCATTTCAAGAA
CGGTATGGCGGTGGCGCGCTTCCTCGAAACGAACCCGCGTGTTGAAAAAGTTGTTTA
CCCTGGCCTCCCGTCCCACCCGCAGCACGAACTGGCGAAACGTCAGTGCTCTGGTTG
CCCTGGCATGGTTTCCTTCTACATCAAAGGTGCCCTCCAGCACGCGAAAGCCTTCCT
GAAAAACCTGAAACTGTTCACCCTCGCGGTTTCTCTGGGTGGTTACGAATCTCTCGC
TGAACTGCCGGCGATCATGACCCACGCTTCTGTACCTGAAAAAGACCGTGCGACCCT
CGGTATCAACGATACCCTGATCCGTCTGTCTGTTGGTCTGGAGGACGAACAGGACCT
GCTGGAAGACCTGGATCGTGCTCTCAAAGCGGCGCACCCGAGCGGTGGTGGTGGTA
GTGGTGGCGGTGGTATGGCAATGGTTAGCGAATTTCTGAAACAGGCACGTTTTCTGG
AAAACCAAGAACAAGAATATGTTCAGGCCGTGAAAAGCTATAAAGGTGGTCCGGGT
AGCGCAGTTAGCCCGTATCCGAGCTTTAATGTTAGCAGTGATGTTGCAGCACTGCAT
AAAGCCATTATGGTTAAAGGTGTTGATGAAGCCACCATCATTGATATTCTGACCAAA
CGTACCAATGCACAGCGTCAGCAGATTAAAGCAGCATATCTGCAAGAAATGGTAA
ACCGCTGGATGAAGTTCTGCGTAAAGCACTGACAGGTCATCTGGAAGAGGTTGTTCT
GGCAATGCTGAAAACACCGGCACAGTTTGATGCAGATGAACTGCGTGGTGCAATGA
AAGGTCTGGGCACCGATGAAGATACACTGATTGAAATCCTGACCACCCGTAGCAAT
GAGCAGATTCGTGAAATTAATCGTGTGTATCGCGAAGAACTGAAACGTGATCTGGC
AAAAGATATCACCAGCGATACCAGCGGTGATTTTCGTAAAGCCCTGCTGGCACTGGC
CAAAGGTGATCGTTGTCAGGATCTGAGCGTTAACCAGGATCTGGCAGATACCGATG
CACGTGCCCTGTATGAAGCCGGTGAGCGTCGTAAAGGTACTGATGTGAACGTTTTCA
CTACGATTCTGACCTCCCGTTCTTTCCCGCATCTCCGTCGTGTGTTCCAGAACTATGG
TAAGTACTCTCAGCACGACATGAACAAAGCGCTGGACCTGGAACTCAAAGGTGACA
TTGAAAAGTGCCTCACCACCATCGTTAAATGCGCGACCTCTACCCCTGCTTTCTTCGC
GGAAAAACTGTATGAGGCCATGAAGGGTGCGGGCACTCGTCACAAGGCTCTGATCC
GTATTATGGTTTCCCGTAGCGAGATTGATATGAACGAAATTAAGGTTTTCTACCAGA
AAAAGTACGGTATCAGCCTGTGCCAGGCGATCCTGGACGAAACCAAAGGCGACTAC
GAAAAGATTCTGGTTGCGCTGTGCGGTGGTAACTGA

FIG. 25

```
ATGCACCATCATCATCATCATTCTTCTGGTCTGGTGCCACGCGGTTCTGGTATGAAA
GAAACCGCTGCTGCTAAATTCGAACGCCAGCACATGGACAGCCCAGATCTGGGTAC
CGATGACGACGACAAGATGCTGGAAGTTCTGTTCCAGGGTCCGATGCAGAAAGACG
CGAGCCTGTCTGGCTTCCTGCCGTCTTTTCAGCACTTCGCAACTCAGGCGATCCACGT
TGGTCAGGAGCCTGAACAATGGAACTCTCGTGCGGTTGTTCTGCCGATCAGCCTCGC
CACGACCTTCAAACAGGATTTCCCGGGTCAGTCTTCTGGTTTCAACTACTCCCGTTCT
GGCAATCCGACCCGTAACTGCCTGGAAAAAGCGGTAGCCGCGCTGGACGGTGCGAA
ACACTCTCTGGCGTTCGCCTCTGGTCTCGCGGCGACCATCACGATCACCCATCTGCT
CAAGGCCGGTGACGAAATCATCTGTATGGACGAAGTTTACGGTGGCACCAACCTGT
ATTTTCGTCGTGTTGCGTCTGAATTCGGTCTGAAAATCTCTTTCGTTGACTGCTCTAA
AACCAAACTCCTGGAGGCAGCAATTACTCCGCAGACGAAACTCGTTTGGATCGAAA
CCCCGACCAACCCGACCCTGAAGCTCGCCGACATCGGTGCGTGCGCTCAAATCGTTC
ACAAACGTGGTGACATCATCCTGGTTGTTGATAATACCTTCATGTCTGCGTACTTTCA
GCGTCCGCTGGCGCTGGGCGCTGACATCTGCATGTGCTCCGCGACCAAATACATGAA
CGGTCACTCTGACGTAGTTATGGGTCTGGTTAGCGTTAACAGCGACGATCTCAATTC
CCGCCTGCGTTTCCTGCAGAACTCCCTCGGCGCAGTACCGTCCCCGTTCGACTGCTA
TCTCTGCTGCCGTGGTCTCAAAACGCTGCAGGTTCGTATGGAAAAGCATTTCAAGAA
CGGTATGGCGGTGGCGCGCTTCCTCGAAACGAACCCGCGTGTTGAAAAAGTTGTTTA
CCCTGGCCTCCCGTCCCACCCGCAGCACGAACTGGCGAAACGTCAGTGCTCTGGTTG
CCCTGGCATGGTTTCCTTCTACATCAAAGGTGCCCTCCAGCACGCGAAAGCCTTCCT
GAAAAACCTGAAACTGTTCACCCTCGCGGTTTCTCTGGGTGGTTACGAATCTCTCGC
TGAACTGCCGGCGATCATGACCCACGCTTCTGTACCTGAAAAAGACCGTGCGACCCT
CGGTATCAACGATACCCTGATCCGTCTGTCTGTTGGTCTGGAGGACGAACAGGACCT
GCTGGAAGACCTGGATCGTGCTCTCAAAGCGGCGCACCCGAGCGGTGGTGGTGGTA
GTGGTGGCGGTGGTATGGCGACCCGTGGTACCGTTACTGATTTCCCGGGTTTCGACG
GTCGTGCGGACGCGGAAGTTCTGCGTAAAGCGATGAAAGGCCTGGGTACGGATGAA
GATTCTATCCTGAACCTGCTGACGTCTCGTTCTAACGCGCAACGCCAGGAAATCGCG
CAGGAGTTCAAAACGCTGTTTGGCCGCGACCTGGTGGACGACCTCAAGTCCGAGCT
GACCGGTAAATTCGAAAAACTGATTGTTGCCATGATGAAGCCGTCCCGTCTGTATGA
CGCGTACGAGCTCAAGCATGCGCTGAAAGGTGCTGGCACCGACGAAAAGGTTCTGA
CCGAGATCATCGCCTCTCGTACCCCGGAAGAACTGTCTGCGATTAAACAGGTTTACG
AGGAAGAATACGGTTCTAATCTGGAGGACGACGTGGTCGGCGATACTTCTGGTTACT
ATCAGCGTATGCTCGTTGTCCTGCTCCAGGCCAATCGTGATCCGGACACTGCGATCG
ACGATGCGCAAGTTGAGCTGGACGCACAGGCGCTCTTCCAGGCTGGTGAACTGAAA
TGGGGCACGGACGAGGAGAAGTTCATCACCATCTTCGGCACGCGTTCTGTTAGCCAC
CTGCGTCGTGTTTTCGACAAATACATGACCATCTCTGGCTTTCAGATCGAAGAAACC
ATTGACCGTGAGACCTCTGGTAACCTGGAACAGCTGCTGCTGGCGGTTGTTAAATCT
ATCCGTTCTATTCCGGCGTACCTGGCGGAAACCCTGTACTACGCCATGAAGGGTGCG
GGCACTGACGATCACACCCTGATTCGTGTTGTTGTTTCTCGCTCCGAGATTGATCTCT
TCAATATCCGTAAGGAATTTCGTAAAAACTTTGCGACTTCCCTCTACTCTATGATCAA
AGGCGACACTAGCGGCGACTACAAAAAAGCGCTGCTCCTGCTGTGCGGTGGTGAAG
ACGACTGA
```

ENZYME CONJUGATE AND PRODRUG CANCER THERAPY

CROSS REFERENCE TO RELATED APPLICATIONS/INCORPORATION BY REFERENCE STATEMENT

This application claims benefit under 35 USC § 119(e) of provisional application U.S. Ser. No. 62/055,264, filed Sep. 25, 2014. The entire contents of the above-referenced application are hereby expressly incorporated herein by reference.

STATEMENT REGARDING FEDERALLY SPONSORED RESEARCH OR DEVELOPMENT

This invention was made with government support under Contract Number W81XWH-08-1-0722 awarded by the U.S. Department of Defense. The government has certain rights in the invention.

BACKGROUND

Although the rate of cancer incidence has declined since 1990, the number of people in the U.S. who are expected to die in 2015 from cancer is still expected to exceed half a million. The five most prevalent types of cancer in the U.S., ranked by the estimated number of new cases for the year 2015 (excluding base and squamous cell cancers of the skin), are as follows: prostate, female breast, lung and bronchus, colon and rectum, and urinary bladder. Breast cancer is the leading cause of cancer in U.S. women, with approximately 232,000 new cases diagnosed and 40,000 deaths per year.

Several modalities, including radiation, chemotherapy, and surgery, either alone or in combination, are being used for the treatment of cancer. Because of these treatments, most patients with skin cancer, and about half the people treated for internal cancers, are completely freed of their disease. However, the therapies now available for internal cancers often give rise to side effects so harmful that they compromise the benefits of treatment, and existing therapies for such internal cancers often fail in many cases. Radiation and surgery are limited in that they cannot treat widespread metastases that eventually form full-fledged tumors at numerous sites. In the 1960's it was discovered that chemotherapy could cure some cancers when several drugs were given in combination. Unfortunately, the most common cancers (breast, lung, colorectal, and prostate cancer) are not yet curable with chemotherapy alone.

Enzyme prodrug therapy was proposed in the mid-1980's as a means of restricting the action of cytotoxic drugs to tumor sites, thereby increasing their efficacy and reducing their normal tissue toxicity. Enzyme prodrug therapy is a two-step approach. In the first step, a drug-activating enzyme is targeted to the tumor cells. In the second step, a nontoxic prodrug, a substrate of the exogenous enzyme that is not expressed in tumors, is administered systemically. The net gain is that a systemically administered prodrug can be converted to high local concentration of an active anticancer drug in tumors. The enzyme should be either of nonhuman origin or a human protein that is absent or expressed only at low concentrations in normal tissues. The enzyme prodrug systems developed to-date have used antibodies to target the enzyme to the tumor, and this therapy has been called antibody-directed enzyme prodrug therapy (ADEPT). Drawbacks of ADEPT include poor accessibility of the enzyme/antibody conjugate to the tumor, the cost and difficulties with development and purification of antibodies, and immunogenicity of both the antibody and the enzyme. In other prodrug therapies, high doses of the prodrug and/or targeting enzymes are necessary.

Therefore, there is a need in the art for new and improved methods of targeting anticancer agents specifically to the surface of cancer cells, or specifically to the surface of blood vessels supplying the cancer cells. It is to such methods of targeting anticancer agents to the surface of cancer cells or blood vessels supplying the cancer cells, thereby requiring significantly lower dosages of anticancer agents than current methods, and thus overcoming the disadvantages and defects of the prior art, that the presently disclosed inventive concepts is directed.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 17 shows the amino acid sequence of a wild-type mouse cystathione-gamma-lyase (SEQ ID NO:1).

FIG. 18 shows the amino acid sequence of a wild-type human cystathione-gamma-lyase (SEQ ID NO:2).

FIG. 19 shows the amino acid sequence of Annexin V (SEQ ID. NO:5).

FIG. 20 shows the amino acid sequence of Annexin I (SEQ ID. NO:6).

FIG. 21 shows the pre-cleavage amino acid sequence of the mCGL-AV fusion protein (SEQ ID NO: 8).

FIG. 22 shows the pre-cleavage amino acid sequence of the mCGL-AI fusion protein (SEQ ID NO: 9).

FIG. 23 shows the post-cleavage amino acid sequence of the mCGL-AV fusion protein (SEQ ID NO: 10).

FIG. 24 shows the post-cleavage amino acid sequence of the mCGL-AI fusion protein (SEQ ID NO: 11).

FIG. 25 shows the DNA sequence of the mCGL-AI fusion gene (SEQ ID NO:12) including sequencing primer (underlined).

FIG. 26 shows the DNA sequence of the mCGL-AV fusion gene (SEQ ID NO:13) including sequencing primer (underlined).

DETAILED DESCRIPTION

Figure 1:
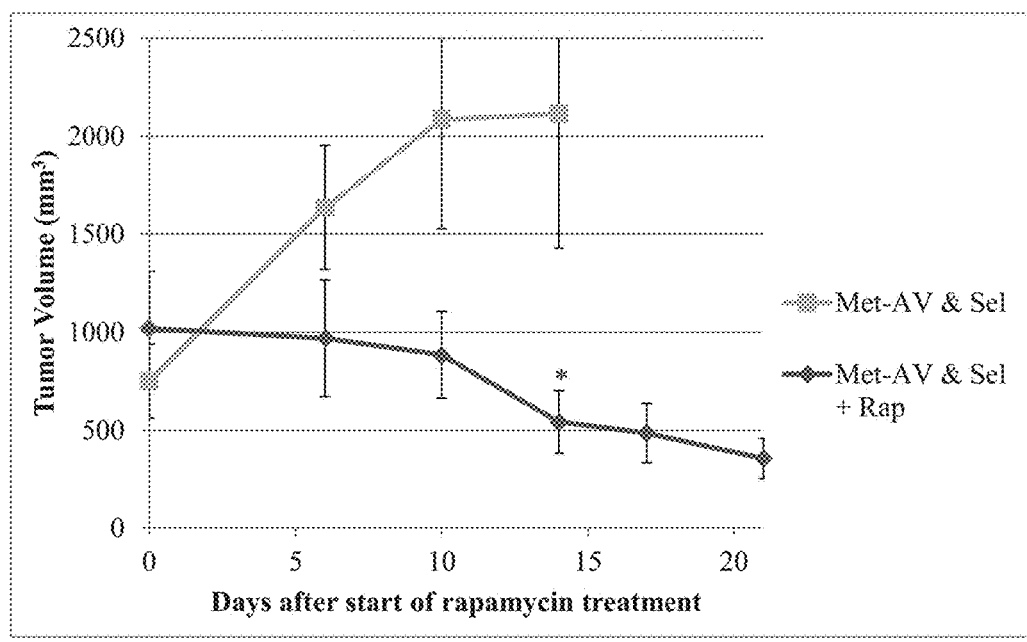
FIG. 1 shows preliminary results of enzyme prodrug combination therapy with rapamycin. An L-methioninase-annexin V (Met-AV) conjugate was administered daily by intraperitoneal (IP) injection at 10 mg/kg followed 12 h later by the administration of selenomethionine (Sel) at 5 mg/kg IP. Upon strong tumor growth despite enzyme prodrug treatment, daily rapamycin co-treatment was initiated at 5 mg/kg IP. Data is presented as mean±SE (n=6-9). Statistical significance is indicated by * (p<0.05). The combination therapy with rapamycin produces antitumor effect on large human MDA-MB-231 breast tumors (implanted orthotopically) in SCID mice.

The presently disclosed inventive concepts are directed to methods of treating cancer utilizing an enzyme prodrug therapy, as well as methods of producing cancer cell-targeted enzyme conjugates including the enzyme utilized in the enzyme prodrug therapy. The presently disclosed inventive concepts are further related to compositions comprising said enzyme conjugate and prodrug, wherein the compositions may be utilized in the methods of treating cancer described herein. The presently disclosed inventive concepts are also related to kits that include said enzyme conjugate and prodrug.

In another embodiment, the presently disclosed inventive concepts are also directed to methods of treating cancer as described herein, wherein such methods further include the use of an immunostimulant, and/or a hypoxia-inducible factor-1 (HIF-1) inhibitor (for example, but not by way of limitation, a mammalian mechanistic target of rapamycin (mTOR) inhibitor), and/or a chemotherapeutic agent in such methods. The presently disclosed inventive concepts also include compositions that comprise the enzyme conjugate and prodrug as well as the immunostimulant, and/or an HIF-1 inhibitor, and/or chemotherapeutic agent. In addition, the presently disclosed inventive concepts are directed to kits that include the enzyme conjugate, prodrug, and/or an immunostimulant, and/or an HIF-1 inhibitor, and/or a chemotherapeutic agent.

Before further description of embodiments of the presently disclosed inventive concepts by way of exemplary drawings, experimentation, results, and laboratory procedures, it is to be understood that the presently disclosed inventive concepts are not limited in application to the details of compositions and methods set forth in the following description or illustrated in the drawings, experimentation and/or results. The presently disclosed inventive concepts are capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concepts shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. *Molecular Cloning: A Laboratory Manual* (2nd ed., Cold Spring Harbor Laboratory Press, Cold Spring Harbor, N.Y. (1989) and Coligan et al. *Current Protocols in Immunology* (Current Protocols, Wiley Interscience (1994)), which are incorporated herein by reference. The nomenclatures utilized in connection with, and the laboratory procedures and techniques of, analytical chemistry, synthetic organic chemistry, molecular and cellular biology, and medicinal and pharmaceutical chemistry described herein are those well known and commonly used in the art. Standard techniques are used for chemical syntheses, chemical analyses, pharmaceutical preparation, formulation, and delivery, and treatment of patients.

All publications, published patent applications, and issued patents mentioned in the specification are indicative of the level of skill of those skilled in the art to which the presently disclosed inventive concepts pertain. All publications, published patent applications, and issued patents are explicitly incorporated by reference herein to the same extent as if each individual publication, published patent application, or issued patent was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and/or claimed herein can be made and executed without undue experimentation in light of the present disclosure. While the compositions and methods of the presently disclosed inventive concepts have been described in terms of particular embodiments, it will be apparent to those of ordinary skill in the art that variations may be applied to the compositions and/or methods and in the steps or in the sequence of steps of the methods described herein without departing from the concept, spirit and scope of the inventive concepts. All such similar substitutes and modifications apparent to those skilled in the art are deemed to be within the spirit, scope and concept of the inventive concepts as described herein.

According to the presently disclosed inventive concepts, enzyme conjugates for use in a prodrug cancer therapy treatment protocol include a ligand having the ability to specifically and stably bind to an external receptor and/or binding site on an outer surface of a tumor vasculature endothelial cell and/or cancer cell, wherein the external receptor and/or binding site is specific for tumor vasculature endothelial cells and/or cancer cells (i.e., is uniquely expressed or overexpressed on a luminal surface of the tumor vasculature endothelial cell or cancer cell). The enzyme conjugate further includes an enzyme that is operatively attached to the ligand, wherein the enzyme is able to convert a prodrug into an active anticancer drug. In at least one embodiment, the enzyme conjugate is maintained on the outer surface of the tumor vasculature endothelial cell and/or cancer cell with substantially no internalization of the enzyme conjugate.

The ligand of the enzyme conjugate of the presently disclosed inventive concepts may be any protein or composition which binds to the receptor or other targeting molecule uniquely present on the surface of cancer cells or cells in the tumor vasculature (i.e., an aminophospholipid). When the ligand is a protein, the ligand may contain the entire protein that binds to the desired receptor or other targeting molecule, or the ligand may contain only a portion of the protein. For example, it may be desirable to remove a portion of the protein that has an undesirable biological activity, or it may be desirable to remove a portion of the protein to enable attachment of the anticancer agent. When a portion of the protein is present as the ligand in the enzyme conjugate, the only requirement is that the portion of the protein substantially retains the protein's receptor or targeting molecule binding activity. In addition, if the protein contains a portion that targets the protein for internalization, such portion should be removed so that the enzyme conjugate of the presently disclosed inventive concepts is stably bound to the outer surface of the cancer cell or blood vessel supplying the tumor. In one embodiment, the enzyme conjugate is maintained on the outer surface of the cancer cell or blood vessel with substantially no internalization thereof. The terms "portion" and "fragment" are used herein interchangeably.

Likewise, the enzyme conjugate may contain a variant or mutant of the ligand. For example, it may be desirable to modify a portion of the ligand that has an undesirable biological activity, or it may be desirable to modify a portion of the ligand to enable attachment of the anticancer agent. When a variant of the ligand is present in the enzyme conjugate, the only requirement is that the ligand variant substantially retains the ligand's receptor or targeting molecule binding activity. Also, sequences may be added to, or inserted within, the ligand during modification, as long as the modified ligand substantially retains the ligand's receptor binding activity. Therefore, it is to be understood that the term "ligand variant" includes both substitutions (including but not limited to conservative and semi-conservative substitutions) as well as additions and insertions to the native ligand's sequence that do not substantially affect the ligand's receptor binding activity. Such variations may occur at the nucleic acid level during construction of the construct from which the enzyme conjugate is expressed, or the variations may be produced by other posttranscriptional or posttranslational means known to those or ordinary skill in the art, including but not limited to, mutations and chemical modifications.

Examples of receptors that may be targeted by enzyme conjugates in accordance with the presently disclosed inventive concepts include, but are not limited to, urokinase receptor, epidermal growth factor (EGF) receptor, insulin-like growth factor receptor, interleukin-4 (IL-4) receptor, interleukin 6 (IL-6) receptor, keratinocyte growth factor (KGF) receptor, platelet-derived growth factor (PDGF) receptor, fibroblast growth factor (FGF) receptor, laminin receptor, vascular endothelial growth factor (VEGF) receptor, transferrin receptor, phosphatidylserine (PS), fibronectin, and the like, as well as portions thereof, and variants thereof, that substantially maintain the ability to bind to the ligand of the enzyme conjugate of the presently disclosed inventive concepts and/or maintain the enzyme conjugate on the surface of the cell with substantially no internalization thereof.

As stated above, the ligand portion of the enzyme conjugate specifically binds to the external receptor or binding site on the outer surface of the cell. In one embodiment, the ligand may be selected from the group consisting of annexins; antibodies to a receptor or aminophospholipid that is uniquely expressed or overexpressed on a surface of a tumor vasculature endothelial cell or cancer cell; RGD-motif peptides (Receptor: integrins alpha-v-beta 3 and alpha-v-beta 5); NGR-motif peptides (Receptor: aminopeptidase N, also known as CD13); F3, a 34-amino acid basic peptide from HMGN2 (Receptor: cell surface nucleolin); HWGF-motif peptides (selective inhibitors of matrix metalloproteinase-2 and matrix metalloproteinase-9, also known as gelatinase A and gelatinase B); the synthetic peptide CTTHWGFTLC (SEQ ID NO:7), which targets angiogenic blood vessels, inhibits the migration of human endothelial cells and tumor cells, and also prevents tumor growth and invasion in animal models and improves survival of mice bearing human tumors; amino-terminal fragment (ATF) of urokinase (which binds to the urokinase receptor, but, unlike full length urokinase, is not internalized); and fragments or variants thereof which substantially retain the ability to bind to the receptor or binding site. In one embodiment, the ligand may be a phosphatidylserine-binding protein.

Where used herein, the terms "specifically binds to," "specific binding," "binds specifically to," and "binding specificity" refer to the ability of a ligand (e.g., an annexin) or other agent to detectably bind to a receptor or a binding epitope while having relatively little detectable reactivity with other proteins, epitopes, or receptor structures presented on cells to which the ligand or other agent may be exposed.

Where used herein the term "annexin" refers to any of annexins 1-11 and 13, which are more particularly designated as annexins A1, A2, A3, A4, A5, A6, A7, A8, A9, A10, A11, and A13. Annexin I and annexin V where used herein refer to Annexin A1 and Annexin A5, respectively, for example. The annexins contemplated herein further include non-human cognate orthologs of A1-A11 and A13 from non-human vertebrates, including but not limited to, non-human primates, dogs, cats, horses, livestock animals and zoo animals, which may be used for treatment in said non-human mammals in the methods contemplated herein. The annexins contemplated for use herein are discussed in further detail in V. Gerke and S. E. Moss (Physiol. Rev., 82:331-371 (2002)), the entirety of which is expressly incorporated by reference herein.

Anionic phospholipids are largely absent from the surfaces of resting mammalian cells under normal conditions. Phosphatidylserine (PS) is the most abundant anionic phospholipid of the plasma membrane and is tightly segregated to the internal side of the plasma membrane in most cell types. Recently, it has been discovered that PS is expressed on the outside surface of the endothelial cells that line the blood vessels in tumors in mice but is not expressed on the outside surface of the vascular endothelium in normal organs. In addition, anionic phospholipids have been shown to be expressed on the outside surface of cancer cells.

The tumor vasculature is increasingly recognized as a target for cancer therapy. Angiogenesis, the formation of new capillaries from existing blood vessels, is essential for the growth of solid tumors beyond 1-3 mm in size. Damage to the endothelial cells that line the blood vessels results in the induction of the coagulation cascade, causing intratumoral vessel occlusion and subsequent tumor necrosis. Targeting the tumor vasculature has the advantage that the delivery vehicle, once in the bloodstream, has direct access to the target endothelial cells. Other advantages of targeting the tumor vasculature rather than the tumor cells themselves include a potentiation effect, because one blood vessel nourishes hundreds of tumor cells. There have, however, been no studies reported of targeting enzyme/prodrug therapy to the tumor vasculature.

In one embodiment of the enzyme conjugate of the presently disclosed inventive concepts, human annexin V, a member of the annexin family of $Ca^{2+}$-dependent anionic phospholipid binding proteins (others are noted above), is used as the ligand and is operatively attached to or otherwise physically associated with an enzyme for targeting the tumor vasculature endothelial cells. Annexin V is a member of a class of widely distributed proteins which bind to anionic phospholipids and membranes in a $Ca^{2+}$-dependent manner. Annexin V is a monomeric protein, which has been crystallized and shown to consist of four tandem repeats of similar structure. Structural evidence shows that the N-terminus of annexin V is located at the surface of the protein and faces away from the membrane-binding side of the molecule. It was later found that the attachment of prourokinase at the N-terminus of annexin V did not alter its affinity for cell membranes in which PS was exposed on the membrane surface, which is consistent with the previous structural evidence.

Annexin V (and other annexins) binds with very high affinity to PS-containing phospholipid bilayers. Annexin V may be obtained, for example, as described in U.S. Pat. No. 7,393,833, issued to Lind et al. on Jul. 1, 2008, the entire contents of which are hereby expressly incorporated by reference.

Examples of other PS-binding proteins that can be used in substitution include those in the Annexin family (listed above), lactadherin, domains found in proteins known to bind PS, such as Factor V/Va, Factor X/Xa, Factor II/II, Factor VII/VIIa, Factor IX/IXa, Factor VIII/IIIa, Spectrin, Class B Scavenger receptor type I, Protein Kinase C, and proteins containing the C2 domains of protein kinase C (this includes synaptotagmins), Rabphilin family members, the PS receptor, endothelial lectin-like OxLDL receptor-1 (LOX-1), antibodies to PS, phosphatidylserine decarboxylase, MARCKS (myristoylated, alanine-rich protein kinase C substrate), PS-p68, Myosin, Erythrocyte protein 4.1, hemoglobin, Calponin family members, S100A, S100B, calcyclin-binding protein family members, milk membrane-glycoprotein, MFG-E8 (milk fat globule-EGF factor 8), and other PS-binding motifs known to those of ordinary skill in the art.

Alternatively, the ligand of the enzyme conjugate of the presently disclosed inventive concepts may be an anionic phospholipid-specific antibody, such as (but not limited to) a PS-specific monoclonal antibody. Non-limiting examples of PS-specific monoclonal antibodies include those described in U.S. Pat. Nos. 6,312,694; 6,406,693; 6,783,760; 6,818,213; and 7,067,109. The ligand may be a non PS-binding moiety which binds to another tumor specific feature, such as (but not limited to) those described in U.S. Pat. Nos. 6,451,312; 6,093,399; 6,004,555; and 6,051,230. The ligands of the presently disclosed inventive concepts may be targeted to other tumor/cancer specific external receptors other than anionic phospholipids. Such receptors include, for example, those described in U.S. Pat. Nos. 6,818,213; 6,783,760; 6,451,312; and 6,406,693. As noted above, all of the patents, published patent applications, and publications listed herein are hereby expressly incorporated herein by reference in their entireties.

The modification of one of the receptor-binding ligands described herein above to provide a fragment or variant thereof that substantially maintains the receptor binding ability of the native receptor-binding ligand is fully within the skill of a person in the art and therefore is also within the scope of the presently disclosed inventive concepts. The term "substantially maintains the receptor-binding ability of the native receptor-binding ligand" means that the protein fragment or variant maintains at least 50% of the native ligand's receptor-binding ability, at least 75% of the native ligand's receptor-binding ability, at least 90% of the native ligand's receptor-binding ability, or at least 95% of the native ligand's receptor-binding ability.

The enzyme attached to the ligand of the enzyme conjugate may include any enzyme capable of converting a prodrug into an active anticancer drug that can function in accordance with the presently disclosed inventive concepts. The enzyme can either be (i) of nonhuman origin, (ii) a human protein that is absent or expressed only at low concentrations in normal tissues, or (iii) a variant that is non-immunogenic. Examples of enzymes that may be utilized in enzyme conjugates in accordance with the presently disclosed inventive concepts include, but are not limited to, cystathione-gamma-lyase, L-methioninase, nitroreductase, cytochrome P450, purine-nucleoside phosphorylase, thymidine kinase, alkaline phosphatase, β-glucuronidase, glycosidase, carboxypeptidase, carboxyesterase, penicillin amidase, β-lactamase, and cytosine deaminase, and effective variants (mutants) thereof.

In one embodiment, the enzyme may be L-methioninase (also known as methionine γ-lyase). In certain embodiments the enzyme is a non-L-methioninase that has methioninase activity, such as (but not limited to) a variant of a wild type mammalian cystathione-gamma-lyase (CGL). In at least one embodiment, the enzyme is a variant of wild type mouse CGL or of wild type human CGL. A non-limiting example of one such variant is the mutant of mouse CGL having the amino acid sequence as set forth in SEQ ID NO:3, which is like wild type mouse CGL (SEQ ID NO:1) except for having substitutions in positions 58, 118, and 338 (see Table 5). Other variants may contain substitutions in only one or two of positions 58, 118, and 338. In another variant, position 58 is substituted with valine rather than asparagine. Another non-limiting example of such a variant is the mutant of human CGL having the amino acid sequence as set forth in SEQ ID NO:4, which is like wild type human CGL (SEQ ID NO:2) except for having substitutions in positions 59, 119, and 339 (see Table 5). Other variants may contain substitutions in only one or two of positions 59, 119, and 339. In another variant position 59 is substituted with valine rather than asparagine. The amino acids included in the substitutions in said variant may include amino acids others than those identified in Table 5, including conservative amino acid substitutions described hereinbelow and those identified in U.S. Pat. No. 8,709,407 (for example, in columns 2, 3, and 32 therein). Other variants include variants (with mutations in the homologous positions) of any other primate CGL (e.g., see U.S. Pat. No. 8,709,407, and Stone et al., "De Novo Engineering of a Human Cystathione-gamma-Lyase for Systemic L-Methionine Depletion Cancer Therapy," ACS Chem. Biol. 2012, 7, 1822-1829), or other mammalian CGL, such as (but not limited to) dog, cat, and horse. Other variants include mutant CGLs which have additional substituted amino acids such that they have at least 80% identity to the CGL sequences listed above, or at least 81% identity thereto, or at least 82% identity thereto, or at least 83% identity thereto, or at least 84% identity thereto, or at least 85% identity thereto, or at least 86% identity thereto, or at least 87% identity thereto, or at least 88% identity thereto, or at least 89% identity thereto, or at least 90% identity thereto, or at least 91% identity thereto, or at least 92% identity thereto, or at least 93% identity thereto, or at least 94% identity thereto, or at least 95% identity thereto, or at least 96% identity thereto, or at least 97% identity thereto, or at least 98% identity thereto, or at least 99% identity thereto, wherein "% identity" is defined in at least one embodiment as the percentage of amino acids (or nucleotides) which are identical at corresponding positions in two amino acid (or nucleic acid) sequences of a protein (or nucleic acid). Said variants of CGL described herein have L-methioninase activity.

The proteins of the presently disclosed inventive concepts may be produced using any nucleotide sequence which encodes the desired amino acid sequence. The proteins may include, for example (but not by way of limitation), conservative substitutions of the amino acid residues of the CGL sequence described herein, wherein such amino acid substitutions do not substantially reduce the L-methioninase activities of the encoded enzyme variant. Examples of conservative amino acid substitutions include, but are not limited to, glycine:alanine substitutions; valine:isoleucine: leucine substitutions; asparagine:glutamine:histidine substitutions; aspartic acid:glutamic acid substitutions; serine: threonine:methionine substitutions; lysine:arginine:histidine substitutions; and phenylalanine:tyrosine:tryptophan substitutions. Other examples of conservative and semi-conservative amino acid substitutions that may be utilized in accordance with the presently disclosed inventive concepts are shown in Table 2. Other types of substitutions, variations, additions, deletions, and derivatives that result in functional CGL variants are also encompassed by the presently disclosed inventive concepts, and one of ordinary skill in the art would readily know how to make, identify, or select such variants or derivatives, and how to test for methioninase activity of those variants.

In one embodiment, the CGL enzyme may itself also have an anticancer activity. Examples of enzyme/anticancer agents that may be utilized in accordance with the presently disclosed inventive concepts include, but are not limited to, L-methioninase and fragments and variants thereof which substantially retain the ability to degrade methionine.

The enzyme and the ligand of the enzyme conjugate may be directly coupled together (e.g., via a covalent bond) or indirectly coupled together via a linker, such as (but not limited to) via a linker peptide. In addition, the enzyme may be conjugated to polyethylene glycol (PEG), or the enzyme conjugate may be encapsulated in a liposome.

In one embodiment, the enzyme conjugate includes (1) an amino acid sequence as set forth in SEQ ID NO:3 or 4, or mutants (variants) thereof as described elsewhere herein, and (2) a ligand such as (but not limited to) an annexin (e.g., one of annexins 1-13) or functional variants thereof.

The presently disclosed inventive concepts include a purified nucleic acid segment encoding an enzyme-ligand conjugate described herein, a recombinant vector comprising said nucleic acid segment, and a recombinant host cell comprising said recombinant vector.

The enzyme conjugates described herein are utilized in combination with a prodrug which may be administered with the enzyme conjugate or separately from the enzyme conjugate. The prodrug utilized in accordance with the presently disclosed inventive concepts is a substrate for the enzyme of the enzyme conjugate and therefore is convertible into an active anticancer drug by the enzyme of the enzyme conjugate. For example but not by way of limitation, a doxorubicin prodrug is converted to doxorubicin by penicillin-V amidase, or a selenomethionine prodrug is converted to methylselenol by L-methioninase or a CGL having L-methioninase activity. Examples of other prodrugs that may be used in accordance with the presently disclosed inventive concepts include but are not limited to, methotrexate, 5-fluorouracil, daunomycin, adriamycin, and vinca alkaloid (Deonarain et al., Br. J. Cancer, 70:786-794 (1994). However, the list above is not to be considered exhaustive, but is only a small sample of prodrugs known in the art or otherwise capable of functioning in accordance with the presently disclosed inventive concepts and thus falls within the scope of the presently disclosed inventive concepts.

Examples of various compounds which may be used in combination with a CGL enzyme conjugate of the presently disclosed inventive concepts include, but are not limited to, mechanistic Target Of Rapamycin (mTOR)) inhibitors such as (but not limited to) rapamycin (sirolimus), everolimus (RAD001), temsirolimus (CCI-779), ridaforolimus (deforolimus, AP-23573), metformin, tacrolimus, ABT-578, AP23675, AP-23841, 7-epi-rapamycin, 7-thiomethyl-rapamycin, 7-epi-tromethoxyphenyyl-rapamycin, 7-epi-thiomethyl-rapamycin, 7-demethoxy-rapamycin, 32-demethoxy-rapamycin, 7-desmethyl-rapamycin, 42-O-(2-hydroxy) ethyl-rapamycin, and other analogs of rapamycin ("rapalogs"). Other mTOR inhibitors which may be used in the compositions and methods of the present disclosure include, but are not limited to, those described in U.S. Pat. Nos. 7,504,397; 8,507,492; 8,557,814; 8,906,374; and 9,040,574.

The presently disclosed inventive concepts also include methods of treating a cancer tumor and/or cancer cells supplied by a tumor vasculature. In one embodiment, the method includes providing an enzyme conjugate as described herein above and providing a prodrug that is a substrate for the enzyme of the enzyme conjugate. In the method, the enzyme conjugate is administered to a subject (patient) in need thereof such that a therapeutically effective amount of the enzyme conjugate is brought into contact with at least one cancer cell and/or at least one blood vessel supplying a tumor. In at least one embodiment, the enzyme conjugate is maintained on the outer surface of the cancer cell and/or tumor vasculature endothelial cell with substantially no internalization thereof. Free (unbound) enzyme conjugate may be allowed to clear from the subject's bloodstream, and then a therapeutically effective amount of the prodrug is administered to the subject. The prodrug may be administered alone, or other co-therapeutic drugs may be also administered, either simultaneously with the prodrug or separate from the prodrug. The prodrug comes into contact with the enzyme conjugate and is converted to an active anticancer drug by the enzyme, wherein a high local concentration of the active anticancer drug is generated in close proximity to the tumor cells and/tumor vasculature. The active anticancer drug is then taken up by the tumor cell and/or tumor vasculature and is selectively toxic to the tumor cells and/or tumor vasculature. For example, the anticancer drug is carried across the artery wall to the tumor cells by diffusion and permeation flow (fluid permeates across the artery wall because the pressure is higher inside the artery than outside). Thus, the anticancer drug is released specifically in the tumor, which will cause cells in the tumor to die, including the tumor's endothelial cells that line the tumor vasculature. This will cause much less toxicity to normal organs and tissue compared to when the drug itself is injected into the bloodstream. Death of the tumor vasculature endothelial cells will lead to clotting of the tumor vasculature and cutting off of the blood supply of the tumor cells, thereby causing these cells to die. Non-limiting examples of prodrugs and their corresponding enzymes are shown in Table 1.

In certain embodiments, practice of the method of the presently disclosed inventive concepts may comprise administering to a subject a therapeutically effective amount of the enzyme conjugate, prodrug, and other therapeutics described herein in any suitable systemic and/or local formulation and in therapeutically-effective amounts. Non-limiting examples of therapeutically-effective amounts include amounts in a range of from about 0.1 µg/kg to about 100 mg/kg each of the enzyme conjugates and compound(s). Typically, but not by way of limitation, one or more of the various compounds may be administered over multiple times (for example but not by way of limitation, from one to five times per day, or once or twice per week or month), or continuously or intermittently via a venous drip, depending on the desired therapeutic effect. In one non-limiting example of a therapeutic method of the presently disclosed inventive concepts, the compounds are provided in an IV infusion in the range of from about 1 µg/kg to about 10 mg/kg of body weight once a day.

In a particular embodiment of the presently disclosed inventive concepts, the enzyme conjugate comprises a ligand bound to a mutant cystathione-gamma-lyase having L-methioninase activity. The binding of the enzyme conjugate to the surface of the tumor cells and/or tumor vasculature results in a depletion of exogenous methionine in a vicinity of the cancer cell and/or tumor vasculature, whereby the enzyme conjugate itself is also selectively toxic to the cancer cells and/or tumor vasculature.

TABLE 1

Examples of Enzyme Prodrug Systems

| Enzyme | Prodrug |
| --- | --- |
| Alkaline phosphatase | Etoposide phosphate |
|  | Mitomycin C phosphate |
|  | Doxorubicin phosphate |
|  | Phenolmustard phosphate |
| Carboxypeptidase G2 | Benzoic mustard glutamates |
|  | CMDA |
| Carboxypeptidase A | Methotrexate peptide |
|  | Methotrexate alanine |
| Cytosine deaminase | 5-fluorocytosine |
| β-Lactamase | LY 266070 |
|  | C-DOX |
|  | PRODOX |
|  | Cephalosporin mustards |
|  | Cephalosporin-DACCP |
|  | PROTAX |
|  | Cephalosporin mitomycin C |
|  | C-Mel |

TABLE 1-continued

Examples of Enzyme Prodrug Systems

| Enzyme | Prodrug |
| --- | --- |
| β-Glucuronidase | Phenol mustard glucuronide |
|  | Daunorubicin glucuronide |
|  | Glucuronide camptothecin |
| Nitroreductase | CB1954 |
| Penicillin amidase | N-(4'-hydroxyphenylacetyl) palytoxin |
|  | Doxorubicin-phenoxyacetamide |
|  | Melphalan-phenoxyacetamide |
|  | N-(phenylacetyl) doxorubicin |
|  | N-(phenylacetyl) melphalan |
| Carboxyesterases | CPT-11, Irinotecan |
| Glycosidases | Glycosides |
| Alcohol dehydrogenase | Alcohol |
| Cytochrome P450 | 4-Ipomeanol |
|  | Ifosfamide |
|  | Cyclophosphamide |
| Purine-nucleoside phosphorylase | Fludarabine |
|  | MeP-dR |
| Methionine γ-lyase, | Selenomethionine |
| cystathione γ-lyase (CGL) | Trifluoromethionine |
| Thymidine kinase | Ganciclovir |

Abbreviations:
CMDA: 4-[N-(2-chloroethyl)-N-[2-(mesyloxy)ethyl] amino]benzoyl-L-glutamic acid,
PROTAX: cephalothin-derived prodrug of taxol,
C-Mel: cephalosporin carbamate derivative of melphalan,
MeP-dR: 9-(β-2-deoxy-erythropentofuranosyl)-6-methylpurine In an alternative embodiment of the presently disclosed inventive concepts, the enzyme conjugate and prodrug compositions can be used in concert with chemotherapeutic agents which have increased effectiveness at temperatures elevated above normal physiologic temperatures. Examples of chemotherapeutic agents which can be used herein include, but are not limited to, mitomycin C, nitrosureas, platin analogs, doxorubicin, mitoxantrone, alkylating agents, bleomycin, and anthracyclins, thiotepa, cisplatin, methotrexate, cyclophosphamide, and amphotericin B. The cytotoxic drug produced by the conversion of the prodrug by the enzyme conjugate may also have increased effectiveness at elevated temperatures and may be used either by itself or in combination with another chemotherapeutic agent. The chemotherapeutic agents, the enzyme conjugate, and the prodrug compositions may be administered simultaneously, or the chemotherapeutic agent may be supplied after the enzyme conjugate and prodrug compositions have been administered and are ready to be irradiated. The simultaneous treatment with a cytotoxic drug and enzyme conjugate-prodrug heating therefore results in the increased killing of cancer cells as compared to when the cytotoxic drug is not administered with the enzyme conjugate-prodrug compositions. Dosages at which these chemotherapeutic agents are administered in thermochemotherapeutic treatments can be determined by those of ordinary skill in the art, for example as shown in Hahn et al. (Proc. Nt. Acad. Sci. 72:937-940 (1975)), Zee (Annals of Oncology, 13:1173-1184 (2002)), and Storm (Radiol. Clin. North Am. 27:621-627 (1989)).

In another embodiment of the presently disclosed inventive concepts, the enzyme conjugate-prodrug compositions and methods of use thereof are combined with the use of an immunostimulant. The destruction of the tumor cells and/or tumor vasculature causes tumor antigens to be released into the bloodstream. Tumor antigens alone may not be sufficient to stimulate an appropriate immune response (Dredge et al., Cancer Immunol. Immunother. 51:521-531 (2002). However, the addition of an immunostimulant has been shown to significantly enhance the immune response of the host to the tumor cells, which allows the immune system to mount a systemic attack on the remaining cells of the tumor.

Any immunostimulant known in the art or otherwise capable of functioning in accordance with the presently disclosed inventive concepts may be utilized in the compositions, methods and kits described herein. Examples of immunostimulants that may be utilized in accordance with the presently disclosed and claimed inventive concept include, but are not limited to, cyclophosphamide, glycated chitosan (Naylor et al., The British Journal of Dermatology, 155:1287-1292 (2006)); muramyldipeptide derivatives; trehalose-dimycolates; and BCG-cell wall skeleton (Azuma et al., International Immunopharmacology, 1:1249-1259 (2001)); various cytokines (Weiss et al., Expert opinion on biological therapy, 7:1705-1721 (2007)); anti-CTLA-4 monoclonal antibody (Hurwitz et al., Cancer Research, 60:2444-2448 (2000)); anti-PD-1 monoclonal antibody (Peng et al., Cancer Research, 72:5209-5218 (2012); anti-CD73 monoclonal antibody (Stagg et al., Proc. Nt. Acad. Sci., 107:1547-1552 (2010)); and combinations and/or derivatives thereof. Dosages of immunostimulants can be in the range of, for example, 0.001 to 100 mg/kg of body weight/day, depending on the method of administration.

In the same manner, the methods described herein above may thus include the step of administering an effective amount of an immunostimulant, wherein the immunostimulant is effective in significantly enhancing the immune response of the patient to the tumor cells, and thereby allowing the immune system to mount a systemic attack on the remaining cells of the tumor. The immunostimulant may be administered at the same time as either the enzyme conjugate or the prodrug, or may be administered before or after the administration of the enzyme conjugate and the prodrug; alternatively, the immunostimulant may be administered multiple times to the patient.

In the same manner, the methods described herein above may thus include the step of administering an effective amount of a hypoxia-inducible factor-1 (HIF-1) inhibitor. Examples of HIF-1 inhibitors include, but are not limited to, mTOR inhibitors, such as described above, wherein the mTOR inhibitor is effective in directly or indirectly decreasing the activity of mTOR. mTOR inhibitors can act to inhibit the activity of HIF-1. HIF-1 is a transcripton factor that regulates the expression of hundreds of genes in response to hypoxia, including VEGF, which encodes vascular endothelial factor, a key regulator of antiogenesis; GLUT1, which encodes glucose transporter 1; and HK1 and HK2, which encode hexokinase, the first enzyme of the glycolytic pathway (Zhang et al., Proc. Nt. Acad. Sci., 105:19579-19586 (2008)). Expression of these proteins serves either to increase $O_2$ delivery (VEGF) or to allow metabolic adaptation to reduced $O_2$ availability (GLUT1, HK1, HK2). The HIF-1 inhibitor (such as the mTOR inhibitor) may be administered at the same time as either the enzyme conjugate or the prodrug, or may be administered before or after the administration of the enzyme conjugate and the prodrug; alternatively, the HIF-1 inhibitor may be administered multiple times to the patient.

Other examples of HIF-1 inhibitors include, but are not limited to, compounds shown in U.S. Pat. Nos. 7,652,033; 8,143,228; 8,168,603; 8,394,799; 8,691,866; 8,940,936; 8,962,577; and 9,062,072. Specific non-limiting examples of HIF-1 inhibitors include anthracyclines such as doxorubicin and Daunorubicin; cardiac glycosides such as digoxin, ouabain, and proscillaridin A; BAY 43-9006; CCI-779; CELEBREX® (celecoxib; Pfizer Inc., New York City, N.Y.); PD98059; Trastuzumab (HERCEPTIN®; Roche, Basel, Switzerland); ZD-1839; OSI-774; Imatinib; 2ME2; 17-AAG; Camptothecin; Topotecan; Pleurotin; 1-methylpropyl 2-imidazolyl disulphide; YC-1; and combinations thereof.

As utilized in accordance with the present disclosure, the following terms, unless otherwise indicated shall be understood to have the following meanings:

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a coding sequence isolated away from, or purified free from, unrelated genomic DNA, genes and other coding segments. Included within the term "DNA segment," are DNA segments and smaller fragments of such segments, and also recombinant vectors, including, for example, plasmids, cosmids, phage, viruses, and the like. In this respect, the term "gene" is used for simplicity to refer to a functional protein-, polypeptide-, or peptide-encoding unit. As will be understood by those in the art, this functional term includes genomic sequences, cDNA sequences or combinations thereof "Isolated substantially away from other coding sequences" means that the gene of interest forms the significant part of the coding region of the DNA segment, and that the DNA segment does not contain other non-relevant large portions of naturally-occurring coding DNA, such as large chromosomal fragments or other functional genes or DNA coding regions. Of course, this refers to the DNA segment as originally isolated, and does not exclude genes or coding regions later added to, or intentionally left in, the segment by the hand of man.

In certain embodiments, DNA sequences in accordance with the presently disclosed inventive concepts may include genetic control regions which allow for the expression of the sequence in a selected recombinant host. The genetic control region may be native to the cell from which the gene was isolated, or may be native to the recombinant host cell, or may be an exogenous segment that is compatible with and recognized by the transcriptional machinery of the selected recombinant host cell. Of course, the nature of the control region employed will generally vary depending on the particular use (e.g., cloning host) envisioned.

Truncated genes also fall within the definition of particular DNA sequences as set forth above. Those of ordinary skill in the art would appreciate that simple amino acid removal can be accomplished, and the truncated versions of the sequence simply have to be checked for the desired biological activity in order to determine if such a truncated sequence is still capable of functioning as required. In certain instances, it may be desired to truncate a gene encoding a protein to remove an undesired biological activity, as described herein.

Nucleic acid segments having a desired biological activity may be isolated by the methods described herein. The term "a sequence essentially as set forth in SEQ ID NO:X" means that the sequence substantially corresponds to a portion of SEQ ID NO:X and has relatively few amino acids or codons encoding amino acids which are not identical to, or a biologically functional equivalent of, the amino acids or codons encoding amino acids of SEQ ID NO:X. The term "biologically functional equivalent" is well understood in the art and is further defined in detail herein, as a gene having a sequence essentially as set forth in SEQ ID NO:X, and that is associated with the ability to perform a desired biological activity in vitro or in vivo.

The presently disclosed inventive concepts are not to be regarded as being solely limited to the specific sequences disclosed herein. As described herein above, the scope of sequences contemplated herein may contain one or more substitutions, variations, additions, and deletions when compared to the specific sequences disclosed herein. For example, standardized and accepted functionally equivalent amino acid substitutions are presented in Table 2. One of ordinary skill in the art, given the present specification, would be able to identify, isolate, create, and test DNA sequences and/or enzymes that produce natural, mutant, chimeric, or hybrid molecules having the desired biological activity. As such, the presently disclosed inventive concepts should not be regarded as being limited to the specific sequences disclosed herein.

TABLE 2

Conservative and Semi-conservative Substitutions in amino acids

| Amino Acid Group | Conservative and Semi-Conservative Substitutions |
| --- | --- |
| Nonpolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

The DNA segments of the presently disclosed inventive concepts encompass DNA segments encoding biologically functional equivalent proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the protein or to test mutants in order to examine biological activity at the molecular level or to produce mutants having changed or novel enzymatic activity and/or substrate specificity.

By "polypeptide" is meant a molecule comprising a series of amino acids linked through amide linkages along the alpha carbon backbone. Modifications of the peptide side chains may be present, along with glycosylations, hydroxylations, and the like. Additionally, other nonpeptide molecules, including lipids and small molecule agents, may be attached to the polypeptide.

Another embodiment of the presently disclosed inventive concepts is a purified nucleic acid segment that encodes a protein in accordance with the presently disclosed inventive concepts, further defined as being contained within a recombinant vector. As used herein, the term "recombinant vector" refers to a vector that has been modified to contain a nucleic acid segment that encodes a desired protein or fragment thereof. The recombinant vector may be further defined as an expression vector comprising a promoter operatively linked to said nucleic acid segment.

A further embodiment of the presently disclosed inventive concepts is a host cell, made with a recombinant vector comprising one or more genes encoding one or more desired proteins, such as an enzyme conjugate. The recombinant host cell may be a prokaryotic cell. In another embodiment, the recombinant host cell is a eukaryotic cell. As used herein, the term "engineered" or "recombinant" cell is intended to refer to a cell into which one or more recombinant genes have been introduced mechanically or by the hand of man. Therefore, engineered cells are distinguishable from naturally occurring cells which do not contain a recombinantly introduced gene. Engineered cells are thus cells having a gene or genes introduced therein through the hand of man. Recombinantly introduced genes will either be in the form of a cDNA gene, a copy of a genomic gene, or will include genes positioned adjacent to a promoter associated, or not naturally associated, with the particular introduced gene.

In certain embodiments, the DNA segments further include DNA sequences, known in the art functionally as origins of replication or "replicons," which allow replication of contiguous sequences by the particular host. Such origins allow the preparation of extrachromosomally localized and replicating chimeric or hybrid segments of plasmids, to which the desired DNA sequences are ligated. In certain instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The nucleic acid segments of the presently disclosed inventive concepts, regardless of the length of the coding sequence itself, may be combined with other DNA sequences, such as (but not limited to) promoters, polyadenylation signals, additional restriction enzyme sites, multiple cloning sites, epitope tags, polyhistidine regions, other coding segments, and the like, such that their overall length may vary considerably. It is, therefore, contemplated that a nucleic acid fragment of almost any length may be employed, with the total length preferably being limited by the ease of preparation and use in the intended recombinant DNA protocol.

As used herein, an "enzyme conjugate" refers to a molecule that contains at least one receptor-binding ligand and at least one enzyme that are coupled directly or via a linker and that are produced by chemical coupling methods or by recombinant expression of chimeric DNA molecules to produce fusion proteins.

As used herein, the terms "covalently coupled," "linked," "bonded," "joined," and the like, with reference to the ligand and enzyme components of the enzyme conjugates of the presently disclosed inventive concepts, mean that the specified components are either directly covalently bonded to one another or indirectly covalently bonded to one another through an intervening moiety or components, such as (but not limited to) a bridge, spacer, linker or the like. For example but not by way of limitation, the ligand and the enzyme may be chemically coupled together via a thioether linkage as described in Mickisch et al. (1993). Another example, but not by way of limitation, is the covalent linking of the ligand and the enzyme by a flexible peptide oligopeptide as described by Argos (An investigation of oligopeptides linking domains in protein tertiary structures and possible candidates for general gene fusion, J. Mol. Biol., 211, 943-958 (1990)).

The term "effective amount" refers to an amount of a biologically active molecule or enzyme conjugate or prodrug or derivative thereof or other therapeutic drug sufficient to exhibit a detectable therapeutic effect when used in the manner of the presently disclosed inventive concepts. The therapeutic effect may include, for example but not by way of limitation, inhibiting or reversing the size or effect of a cancerous tumor. The effective amount for a subject will depend upon the type of subject, the subject's size and health, the nature and severity of the condition to be treated, the method of administration, the duration of treatment, the nature of concurrent therapy (if any), the specific formulations employed, and the like. The effective amount for a given situation can be determined by one of ordinary skill in the art using routine experimentation based on the information provided herein.

As used herein, the term "concurrent therapy" is used interchangeably with the terms "combination therapy" and "adjunct therapy," and will be understood to mean that the patient in need of treatment is treated or given another drug for the disease in conjunction with the enzyme conjugates of the presently disclosed inventive concepts. This concurrent therapy can be sequential therapy where the patient is treated first with one drug and then the other, or the two drugs are given simultaneously.

The term "pharmaceutically acceptable" refers to compounds and compositions which are suitable for administration to humans and/or animals without undue adverse side effects.

By "biologically active" is meant the ability to modify the physiological system of an organism. A molecule can be biologically active through its own functionalities, or may be biologically active based on its ability to activate or inhibit molecules having their own biological activity.

As used herein, "substantially pure" means an object species is the predominant species present (i.e., on a molar basis it is more abundant than any other individual species in the composition). In certain embodiments, a substantially purified fraction is a composition wherein the object species comprises at least about 50 percent (on a molar basis) of all macromolecular species present. In certain embodiments, a substantially pure composition will comprise more than about 80 percent of all macromolecular species present in the composition, or more than about 85%, or more than about 90%, or more than about 95%, or more than about 99% of all macromolecular species present in the composition.

A "liposome" is a small vesicle composed of various types of lipids, phospholipids and/or surfactant. The components of the liposome are commonly arranged in a bilayer formation, similar to the lipid arrangement of biological membranes.

As used herein, the term "anticancer agent" refers to a molecule that is formed as a result of the action of the enzyme portion of the enzyme conjugate on a prodrug substrate and that is capable of inhibiting cancer cell function. The anticancer agent may inhibit proliferation or may be cytotoxic to cells. A variety of anticancer agents can be used and include those that inhibit protein synthesis and those that inhibit expression of certain genes essential for cellular growth or survival. Anticancer agents include those that result in cell death and those that inhibit cell growth, proliferation and/or differentiation. In one embodiment, the anticancer agent may be selectively toxic against certain types of cancer cells but does not affect or is less effective against other normal cells.

In certain embodiments, the anticancer agent is an antineoplastic agent. The term "antineoplastic agent" is used herein to refer to agents that have the functional property of inhibiting a development or progression of a neoplasm in a human or animal, particularly a malignant (cancerous) lesion or tumor, such as (but not limited to) a carcinoma, sarcoma, lymphoma, or leukemia. Inhibition of metastasis is frequently a property of antineoplastic agents.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, renal cancer, prostate cancer, vulval cancer, thyroid cancer, hepatic carcinoma and various types of head and neck cancer.

The term "subject" is used interchangeably herein with the term "patient" and includes human and veterinary subjects. For purposes of treatment, the term "mammal" as used herein refers to any animal classified as a mammal, including (but not limited to) humans, non-human primates, monkeys, domestic animals (such as, but not limited to, dogs and cats), farm animals (such as, but not limited to, horses, pigs, cattle, goats, sheep, and llamas), and any other animal that has mammary tissue.

The terms "treat," "treating" and "treatment," as used herein, will be understood to include both inhibition of tumor growth as well as induction of tumor cell death.

The term "receptor" as used herein will be understood to include any peptide, protein, glycoprotein, lipoprotein, polycarbohydrate, or lipid that is uniquely expressed or overexpressed on the surface of cancer cells or cells in the tumor vasculature and is exposed on the surface of cancer cells or cells in the tumor vasculature in a manner that will allow interaction with a circulating targeting agent, such as the enzyme conjugate.

The phrase "substantially no internalization," as used herein, refers to a lack of internalization of a substantial amount of the enzyme conjugates of the presently disclosed inventive concepts. For example, the phrase "substantially no internalization" will be understood as less than 25% of the enzyme conjugates of the presently disclosed inventive concepts being internalized by a cell to which the enzyme conjugate is bound, or less than 10% of the enzyme conjugates of the presently disclosed inventive concepts being internalized by a cell to which the enzyme conjugate is bound, or less than 5% of the enzyme conjugates of the presently disclosed inventive concepts being internalized by a cell to which the enzyme conjugate is bound, or less than 3% of the enzyme conjugates of the presently disclosed inventive concepts being internalized by a cell to which the enzyme conjugate is bound, or less than 1% of the enzyme conjugates of the presently disclosed inventive concepts being internalized by a cell to which the enzyme conjugate is bound.

Since the enzymes described herein are typically bacterially-derived proteins, the enzymes of the enzyme conjugate of the presently disclosed inventive concepts may be modified so as to reduce the immunogenicity thereof. One method for reducing a protein's immunogenicity is to conjugate the protein to polyethylene glycol (PEG). By "polyethylene glycol" or "PEG" is also meant any other polyalkylene glycol compound or a derivative thereof, with or without coupling agents or derivatization with coupling or activating moieties (e.g., with thiol, triflate, tresylate, azirdine, oxirane, or particularly with a maleimide moiety). Compounds such as maleimido monomethoxy PEG are exemplary of activated PEG compounds of the presently disclosed inventive concepts. Other polyalkylene glycol compounds, such as (but not limited to) polypropylene glycol, may be used in the presently disclosed inventive concepts. Other appropriate polymer conjugates include, but are not limited to, non-polypeptide polymers, charged or neutral polymers of the following types: dextran, colominic acids or other carbohydrate based polymers, biotin derivatives and dendrimers, for example. The term PEG is also meant to include other polymers of the class polyalkylene oxides.

The PEG can be linked to any N-terminal amino acid of the enzyme conjugate, and/or can be linked to an amino acid residue downstream of the N-terminal amino acid, such as lysine, histidine, tryptophan, aspartic acid, glutamic acid, and cysteine, for example or other such linkable amino acids known to those of ordinary skill in the art. Cysteine-PEGylated enzyme conjugates, for example, are created by attaching polyethylene glycol to a thio group on a cysteine residue of the enzyme conjugate.

The PEG moiety attached to the enzyme conjugate may range in molecular weight, for example, but not limited to, from about 200 to about 40,000 MW.

The enzyme conjugates contemplated herein can be adsorbed or linked to PEG molecules using techniques shown, for example (but not limited to), in U.S. Pat. Nos. 4,179,337; 5,382,657; 5,972,885; 6,177,087; 6,165,509; 5,766,897; and 6,217,869; and Published Application 2006/0275371; the specifications and drawings each of which are hereby expressly incorporated by reference herein in their entirety.

The immunological response to the enzyme can be greatly reduced or eliminated by either conjugation to PEG or by encapsulation in liposomes, without significant effect on enzymatic activity of the enzyme. Liposome encapsulation has the advantage that covalent attachment of moieties to the enzyme is not required, which may be helpful to preserve binding of the proposed enzyme conjugates to the receptors on cancer cells.

The compositions of the presently disclosed inventive concepts (including the enzyme conjugates, prodrugs, immunostimulants, HIF-1 inhibitors, and/or chemotherapeutic agents described herein) may be administered to a subject by any methods known in the art, including but not limited to, oral, topical, transdermal, parenteral, subcutaneous, intranasal, intramuscular, intraperitoneal, and intravenous routes, including both local and systemic applications. In addition, the compositions of the presently disclosed inventive concepts may be designed to provide delayed or controlled release using formulation techniques which are well known in the art.

The presently disclosed inventive concepts also include a pharmaceutical composition comprising a therapeutically effective amount of any of the compositions described herein above in combination with a pharmaceutically acceptable carrier. As used herein, a "pharmaceutically acceptable carrier" is a pharmaceutically acceptable solvent, suspending agent or vehicle for delivering the enzyme conjugates of the presently disclosed inventive concepts to the human or animal. The carrier may be liquid or solid and is selected with the planned manner of administration in mind. Examples of pharmaceutically acceptable carriers that may be utilized in accordance with the presently disclosed inventive concepts include, but are not limited to, PEG, liposomes, ethanol, DMSO, aqueous buffers (such as, but not limited to, phosphate buffered saline), oils, and combinations thereof.

EXAMPLE

The following non-limiting example serves to illustrate certain useful embodiments and aspects of the presently disclosed inventive concepts and is not to be construed as limiting the scope thereof. Alternative materials and methods can be utilized to obtain similar results.

The fusion protein enzyme conjugate of this example comprises an annexin (e.g. annexin I or annexin V) and an enzyme (a mutant variant of CGL) which binds specifically to the surfaces of the endothelial cells of a tumor vasculature via the annexin ligand portion of the enzyme conjugate. The CGL mutant of the enzyme conjugate acts to catalyze the conversion of an administered non-toxic prodrug, such as (but not limited to) selenomethionine (SeMet), into a toxic drug (e.g., methylselenol) which, by means of permeation and diffusion, travels inside the cells and causes their death. The death of the endothelial cells causes the clotting of tumor vasculature, preventing cancer cells of the tumor from getting necessary nutrients and oxygen. The breaking up of the cells also causes the release of tumor antigens in the blood stream, leading the immune system to mount an attack against tumors throughout the body.

Such a therapy has many advantages. First, the enzyme conjugate is relatively easy to produce and purify. Second, the enzyme conjugate can be easily administered, e.g., through an intravenous injection. Third, there are minimal side effects since the toxic anticancer drug is generated locally in the tumor. Fourth, the breaking up of the endothelial cells causes the release of tumor antigens into the bloodstream, leading the immune system to mount an immune attack against cancer cells throughout the body.

An enzyme prodrug therapy targeted to the tumor vasculature which used an L-methioninase-annexin V enzyme conjugate with selenomethionine as the prodrug was previously developed (e.g., see U.S. Pat. No. 8,986,701). Tests in mice demonstrated a substantial cutoff of blood flowing through the tumor treated with the selenomethionine/enzyme prodrug system. However, there was some regrowth of the tumor at the end of the enzyme conjugate/prodrug treatment. The enzyme conjugates of the present disclosure are directed, in one embodiment, to addressing this issue of tumor regrowth. The addition of rapamycin, an inhibitor of mammalian (mechanistic) target of rapamycin (mTOR) and of HIF-1, to the enzyme conjugate/prodrug therapy was studied. The results of this study are shown in this example.

Various combinations of a novel enzyme conjugate-prodrug therapy were conducted with the antibiotic rapamycin and with the immunostimulant cyclophosphamide. This example used an enzyme conjugate comprising a mouse cystathione-γ-lyase mutant (denoted mCGL) comprising three amino acid mutations in the wild-type amino acid sequence (as discussed above) as the enzyme in the ligand+ enzyme fusion protein.

MDA-MB-231 Implantation in SCID Mice

Six to eight week old female SCID mice (The Jackson Laboratory; Bar Harbor, Me.; 001303) were injected with either (1) 6-8 million MDA-MB-231/GFP cells per mouse subcutaneously in the flank, or (2) 1-2 million MDA-MB-231/GFP cells per mouse in mammary fat pad number 4. Injections were performed with 25 G needles with 50% MATRIGEL® matrix (Fisher Scientific; CB-40234A) and 50% cell suspension in PBS for total volumes of 200 μL for flank injections and 100 μL for fat pad injections. The amino acid sequences of the precleavage mCGL-AV and mCGL-AI (mutant) fusion proteins are shown in FIGS. 21-22, respectively, and the amino acid sequeneces of the postcleavage mCGL-AV and mCGL-AI (mutant) fusion proteins are shown in FIGS. 23-24, respectively. FIGS. 25 and 26 show mCGL Fusion Sequencing Primers and Sequences used to make the fusion proteins. Sequencing primers are indicated with underlines on the fusion gene to indicate the sequencing approach. In addition to the underlined primers indicated below, the sequencing facility at Oklahoma Medical Research Foundation provided T7 promoter and T7 terminator primers. All primers are oriented in the forward direction for simplicity of analysis, with the exception of the T7 terminator primer. Primer spacing was optimized to 350-500 base pairs to ensure accuracy and maximize reuse of primers for mCGL-AI and mCGL-AV. Primers were designed using Gene Designer software (DNA 2.0; Menlo Park, Calif.) and analyzed with OligoAnalyzer 3.1 (Integrated DNA Technologies, Coralville, Iowa) to the following specifications: melting temperature of 55-50° C., length of 18-24 base pairs, no hairpins with a melting temperature >50° C., no self-dimers with $\Delta G<-6$ kcal/mol, and no single base strings >4 base pairs.

Rapamycin resulted in a large antitumor effect when it was used in addition to enzyme prodrug therapy (using an L-methioninase-Annexin V (Met-AV)) fusion protein and selenomethionine prodrug) in SCID mice with implanted human MDA-MB-231 breast tumors, compared to the enzyme prodrug therapy alone (FIG. 1).

Figure 2:
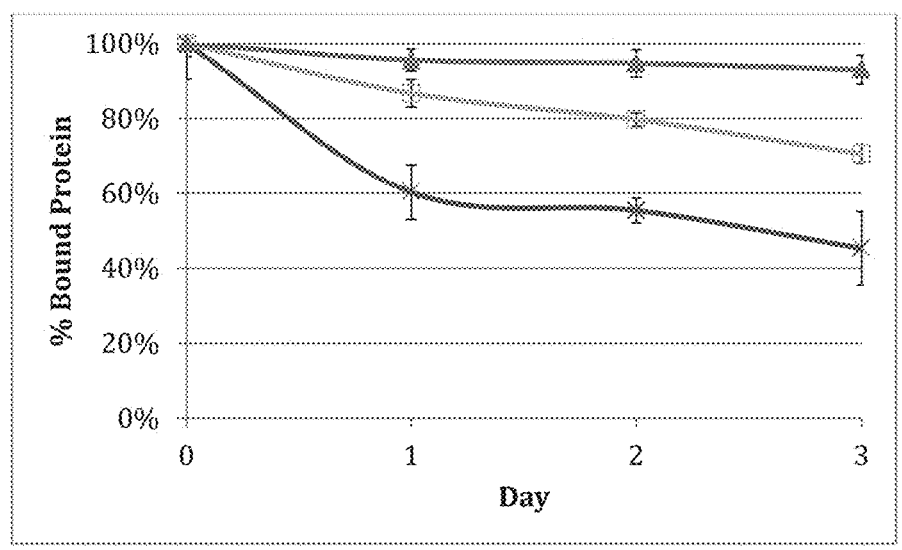
FIG. 2 shows binding stability of a mouse cystathione-gamma-lyase-Annexin I conjugate (mCGL-AI), a mouse cystathione-gamma-lyase-Annexin V conjugate (mCGL-AV), and Met-AV on MDA-MB-231 cells for 3 days. Biotinylated mCGL-AI (x), mCGL-AV (open squares), and Met-AV (▲) were incubated on MDA-MB-231 cells for 2 h at 37° C., and unbound protein was washed away. Streptavidin enzyme conjugated peroxidase was used to determine protein present on the three following days and is presented as a percentage of protein present immediately after the initial wash. Data is mean±SE (n=3). mCGL is a protein with the amino acid sequence as set forth in SEQ ID NO:3.
Figure 3:
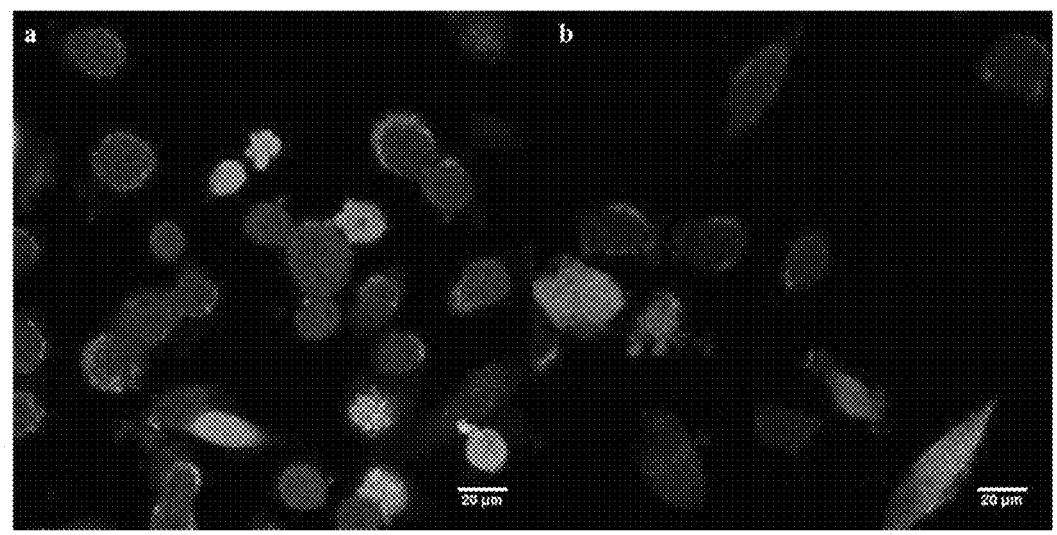
FIG. 3 shows live-cell confocal micrographs confirming membrane binding of mCGL-AI and mCGL-AV. (a) mCGL-AI and (b) mCGL-AV were conjugated to DyLight® 680 fluorescent dye (Pierce Biotechnology, Inc., Rockford, Ill.) (red) and incubated with MDA-MB-231/GFP cells (green). After 2 h at 37° C., cells were washed with culture medium to remove excess protein and imaged using a Leica SP8 confocal microscope with HyD detectors. Cells were kept at 37° C. using a Peltier stage, and viability was confirmed through the lack of nucleic acid staining despite inclusion of membrane impermeable Hoechst 33258 in the imaging medium.

Both the mCGL-AI and mCGL-AV fusion proteins bound strongly to MDA-MB-231 tumor cells and HAAE-1 human endothelial cells in vitro (FIG. 2 and Table 3). Binding of fluorescent-labeled mCGL-AI and mCGL-AV to MDA-MB-231 cells was confirmed using live cell confocal microscopy (FIG. 3).

TABLE 3

Dissociation constants of mCGL-AI, mCGL-AV, and Met-AV on human MDA-MB-231 breast tumors and human HAAE-1 endothelial cells grown in vitro*

| Fusion Protein | MDA-MB-231 | HAAE-1 |
| --- | --- | --- |
| mCGL-AI | 0.68 nM ± 0.3 nM | 2.3 nM ± 1.1 nM |
| mCGL-AV | 2.5 nM ± 1.7 nM | 0.11 nM ± 0.02 nM |
| Met-AV | 4.9 nM ± 0.9 nM | 0.5 nM ± 0.2 nM |

*mCGL-AI: mouse cystathione-γ-lyase-annexin I with three mutations mCGL-AV: mouse cystathione-γ-lyase-annexin V with three mutations Dissociation Constant ($K_d$) ± SE (n = 3)

The L-methioninase enzyme activity of the mCGL-AI and mCGL-AV fusion proteins was substantially equivalent to that of the Met-AV fusion protein (Table 4).

TABLE 4

L-methioninase enzyme activity

| Fusion Protein | Activity |
| --- | --- |
| Met-AV | 1.0 U/mg |
| mCGL-AI | 1.0 U/mg |
| mCGL-AV | 1.3 U/mg |

The specific mutations of the mCGL mutant (SEQ ID NO:3) and the homologous mutations of human CGL (hCGL) (SEQ ID NO:4) are shown in Table 5.

TABLE 5

Substitutions made in wild type mouse CGL (SEQ ID NO: 1) and wild type human CGL (SEQ ID NO: 2) to obtain mCGL (SEQ ID NO: 3) and hCGL (SEQ ID NO: 4) mutants

| Mouse CGL Position | Mutation (WT→mutant) to produce SEQ ID NO: 3 | Human CGL Position | Mutation (WT→mutant) to produce SEQ ID NO: 4 |
| --- | --- | --- | --- |
| 58 | E → N | 59 | E → N |
| 118 | R → L | 119 | R → L |
| 338 | E → V | 339 | E → V |

Figure 4:
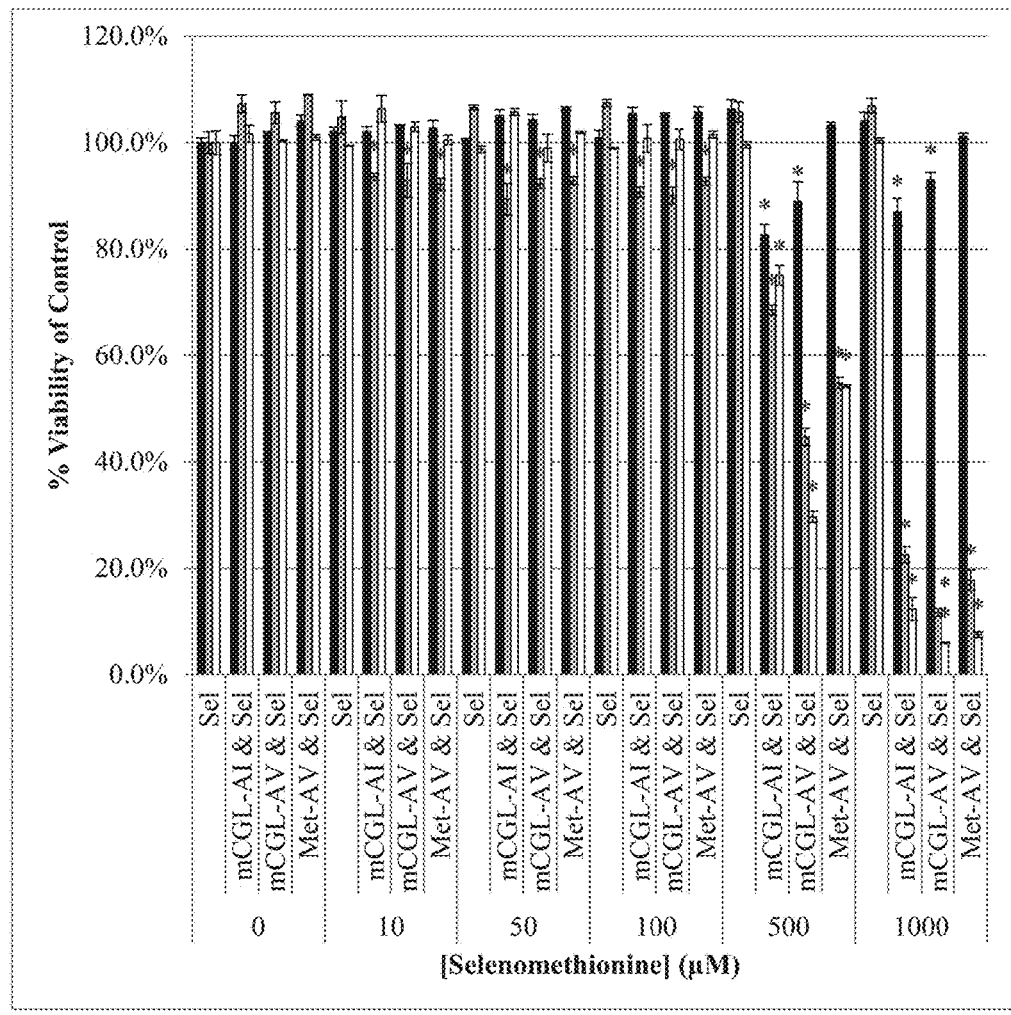
FIG. 4 is a comparison of cytotoxic effects of mCGL-AI, mCGL-AV, and Met-AV enzyme prodrug therapy on MDA-MB-231 cells. Groups that received enzyme conjugate (fusion protein) were treated on day 0. Selenomethionine was administered daily. Viability was determined by the Alamar Blue assay on days 1, 2, and 3 (black, gray, and white bars, respectively), and each sample was represented as a percentage of untreated control on each day. Statistical analysis was performed with a one-way ANOVA test with data presented as mean±SE (n=3). Statistical significance vs. untreated control on the same day is denoted by *(p<0.001).
Figure 5:
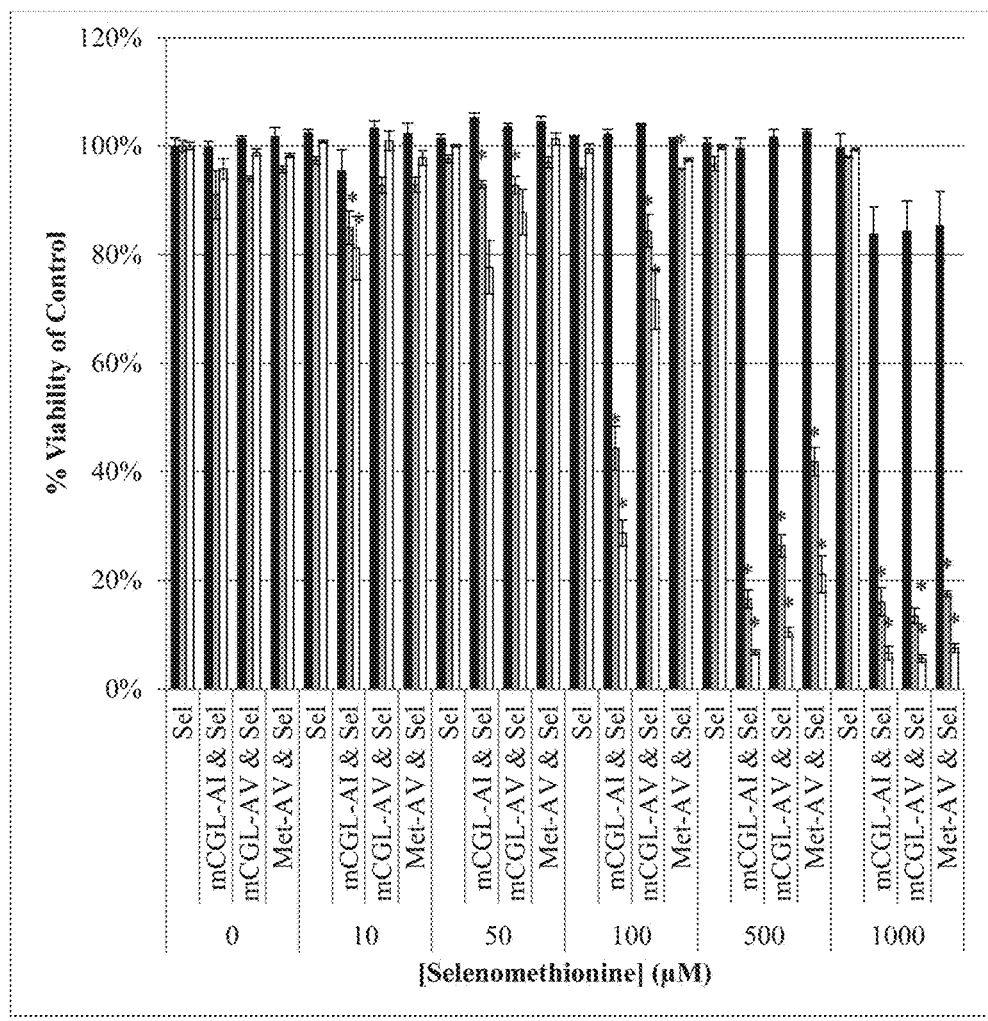
FIG. 5 is a comparison of cytotoxic effects of mCGL-AI, mCGL-AV, and Met-AV enzyme prodrug therapy on mouse 4T1 breast cancer cells. Groups that received enzyme conjugate were treated on day 0. Selenomethionine was administered daily. Viability was determined by the Alamar Blue assay on days 1, 2, and 3 (black, gray, and white bars, respectively), and each sample was represented as a percentage of untreated control on each day. Statistical analysis was performed with a one-way ANOVA test with data presented as mean±SE (n=3). Statistical significance vs. untreated control on the same day is denoted by *(p<0.001).

The cytotoxicity in vitro of the mCGL-AI/Sel and mCGL-AV/Sel enzyme prodrug systems (Sel=selenomethionine) was similar to that for the Met-AV/Sel enzyme prodrug system for MDA-MB-231 tumor cells and HAAE-1 endothelial cells (FIGS. 4 and 5).

Figure 6:
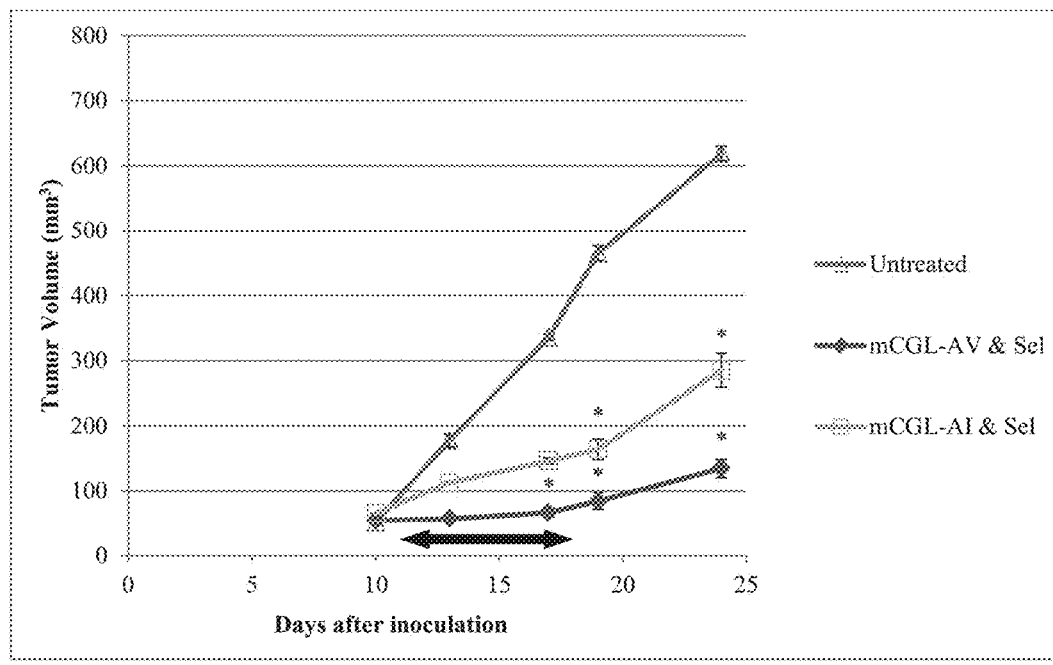
FIG. 6 is a comparison of efficacy of AV- and AI-targeted mCGL enzyme prodrug therapy with selenomethionine on 4T1 tumors implanted orthotopically in BALB/c mice. mCGL-AV and mCGL-AI were administered daily (10 mg/kg IP). Selenomethionine (5 mg/kg IP) was administered 10 h post fusion protein administration. Treatment began on day 11 and continued until day 18 as indicated by the arrow. Statistical significance vs. untreated is indicated by * (p<0.001). No significant difference was observed between treatment groups. No negative effects were observed with either treatment. Data is presented as mean volume±SE (n=6).

The mCGL-AI/Sel enzyme prodrug system was not significantly more effective than the mCGL-AV/Sel enzyme prodrug system for treating mouse 4T1 breast tumors in immune-competent BALB/c mice (FIG. 6).

In Vivo mCGL-AV Plasma Clearance

Figure 7:
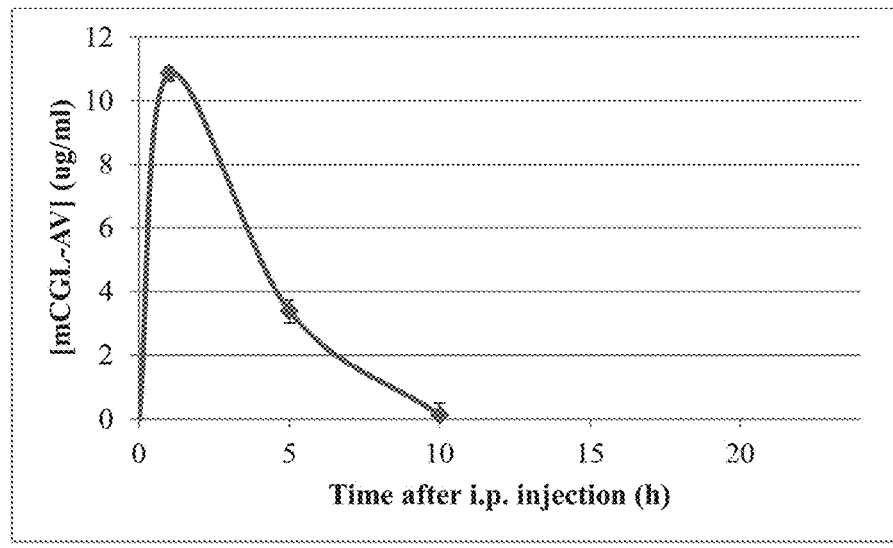
FIG. 7 demonstrates clearance of mCGL-AV from the circulation of SCID mice in <10 h. An ELISA assay for mCGL-AV was performed on serum samples at intervals following intraperitoneal administration of mCGL-AV at 10 mg/kg. Data is presented as mean±SE (n=3).

Clearance of the mCGL-AV protein from the circulation of BALB/cJ mice occurred with pharmacokinetics similar to the other enzyme prodrug systems in SCID mice. Complete clearance occurred within 10 h of a 10 mg/kg intraperitoneal administration of mCGL-AV (FIG. 7).

Using daily intraperitoneal administration, the mCGL-AV fusion protein did not produce detectable IgG+IgM antibody titers in the bloodstream of BALB/c mice during the 21 day period tested (i.e., was not immunogenic), while the Met-AV fusion protein produced detectable antibody titers after 7 days (Table 6).

TABLE 6

Fusion protein specific IgG + IgM Titers in BALB/c mice improved with daily intraperitoneal (IP) administration of mCGL-AV over Met-AV (10 mg/kg IP)

| Fusion Protein | Day 0 | Day 7 | Day 14 | Day 21 |
| --- | --- | --- | --- | --- |
| mCGL-AV | Not detected | Not Detected | Not Detected | Not Detected |
| Met-AV | Not Detected | $10^{-4}$ | $10^{-4}$ | $10^{-5}$ |

After 20 days of treatment, mCGL-AV/Sel enzyme prodrug treatment combined with rapamycin resulted in a large reduction in tumor volume (FIG. 8) and a large increase in survival (FIG. 9 and Table 7) compared to untreated BALB/c mice with 4T1 tumors and also compared to mice receiving only the enzyme prodrug treatment.

TABLE 7

Figure 8:
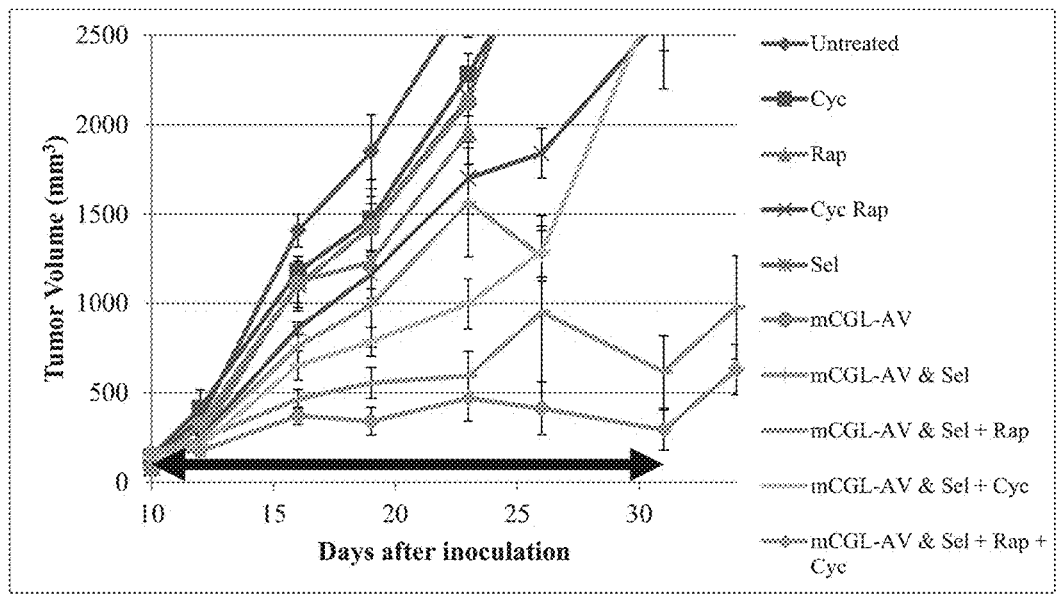
FIG. 8 shows the effects of combination therapy on 4T1 tumor volume in BALB/cJ mice (tumors implanted orthotopically). mCGL-AV and Met-AV were administered daily (10 mg/kg IP). Selenomethionine (5 mg/kg IP) was administered 10 h post fusion protein administration. Rapamycin (5 mg/kg IP) and cyclophosphamide (10 mg/kg IP) were administered daily. Treatment began on day 10 and continued until day 30 as indicated by the arrow. Statistical significance vs. untreated is indicated by * (p<0.001). Data is presented as mean volume±SE (n=5-10 initially, though does drop to as low as 2 as survival decreases towards the conclusion of the study).
Figure 9:
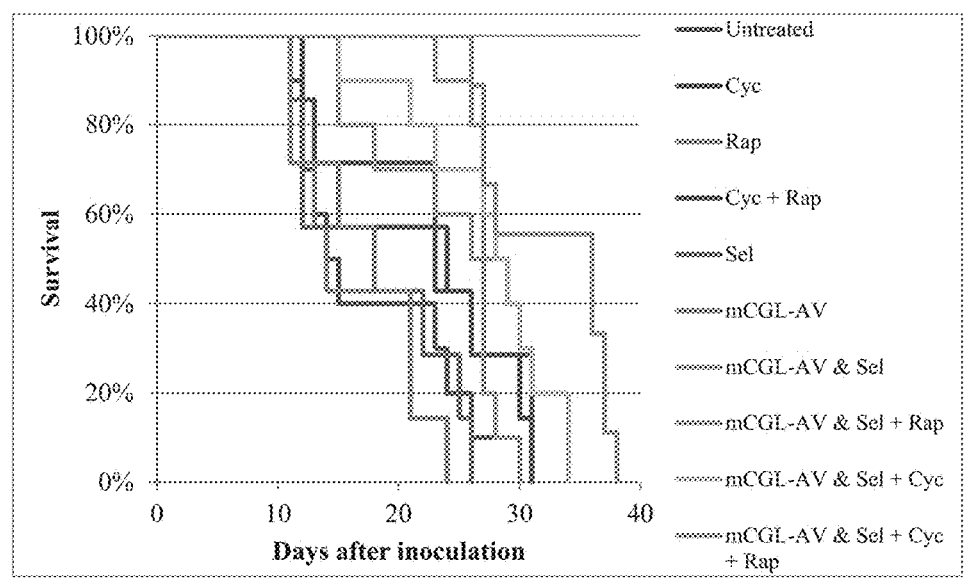
FIG. 9 shows Kaplan-Meier survival curves for combination therapies which demonstrate the effects of combination therapy on survival in BALB/cJ mice (tumors implanted orthotopically). mCGL-AV and Met-AV were administered daily (10 mg/kg IP). Selenomethionine (5 mg/kg IP) was administered 10 h post fusion protein administration. Rapamycin (5 mg/kg IP) and cyclophosphamide (10 mg/kg IP) were administered daily. Treatment began on day 10 and continued until day 30 as indicated by the arrow. Statistical significance vs. untreated is indicated by * (p<0.001). Data is presented as mean volume±SE (n=5-10 initially, though does drop to as low as 2 as survival decreases towards the conclusion of the study).

Survival after treatment using the protocols of FIGS. 8 and 9

| Treatment Protocol | Median Survival (days) |
| --- | --- |
| Untreated | 14 |
| Cyc | 23 |
| Rap | 14 |
| Cyc + Rap | 24 |
| Sel | 18 |
| mCGL-AV | 18 |
| mCGL-AV & Sel | 26 |
| mCGL-AV & Sel + Rap | 27 |
| mCGL-AV & Sel + Cyc | 28 |
| mCGL-AV & Sel + Cyc + Rap | >36 |

Figure 10:
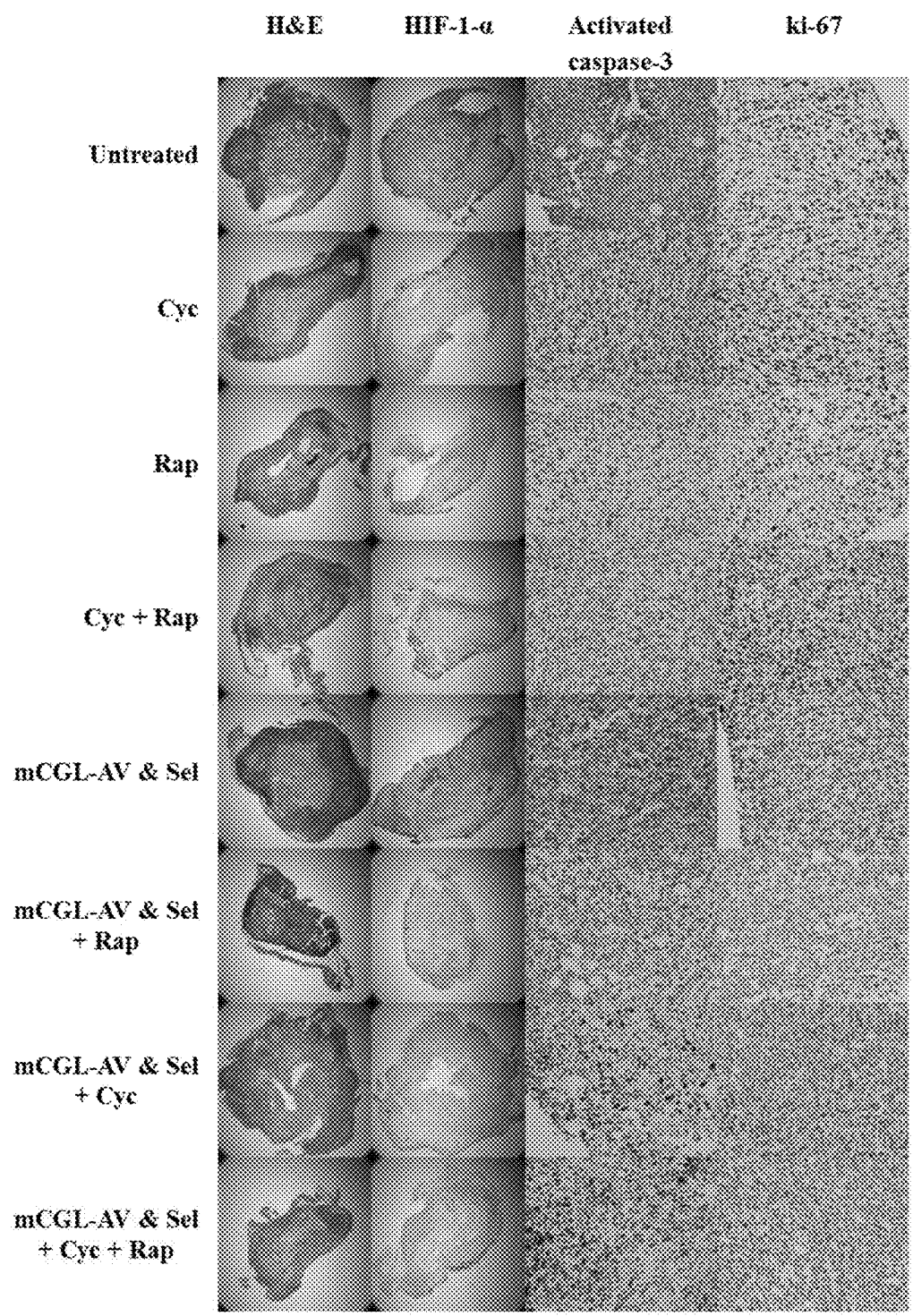
FIG. 10 shows representative immunohistochemical images taken after the treatments of FIG. 9.

The cytotoxic effect on the tumors by the enzyme prodrug therapy was further evaluated with immunohistochemical staining for apoptosis (activated caspase-3) and proliferation (ki-67). The reduction of the hypoxic response due to rapamycin was evaluated through immunohistochemical staining of HIF-1-α and quantification of tumor necrosis. Representative images from each of these experimental approaches are presented in FIG. 10.

Figure 11:
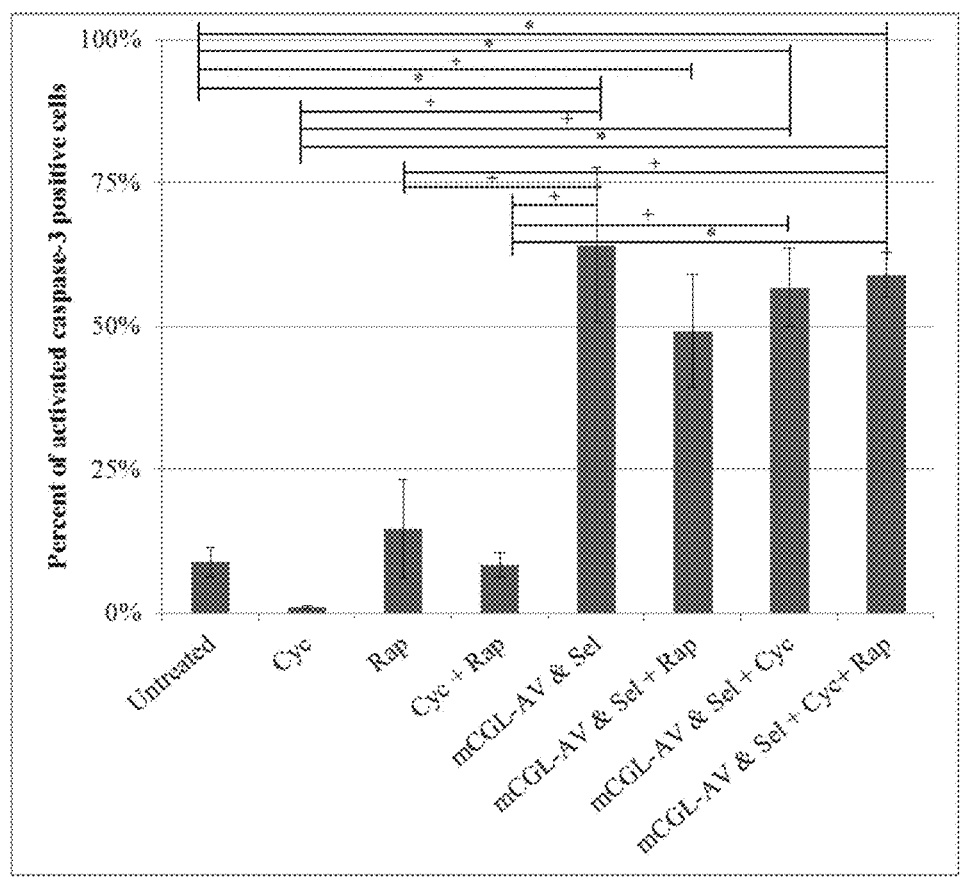
FIG. 11 shows results demonstrating that enzyme prodrug treatment increases staining of apoptosis marker activated caspase-3. A Nikon Eclipse E800 compound microscope was used to capture 15 fields of view of tumor sections from 3 mice per group (necrotic tumor cores were excluded). Immunostaining for activated caspase-3 was quantified as percent of cells (hematoxylin counterstain) with DAB and is presented as mean±SE. Statistical significance between groups is indicated by +(p<0.01) or * (p<0.001).

The extrinsic and intrinsic apoptotic pathways, extrinsic involving the death receptors and the intrinsic involving cell stress causing mitochondrial release of cytochrome c, converge with the proteolytic cascade and activation of caspase-3. The presence of activated caspase-3 indicates forthcoming apoptosis (though necrosis is possible), and the data in FIG. 11 indicate that the enzyme prodrug therapy results in increased activation of apoptotic pathways.

Figure 12:
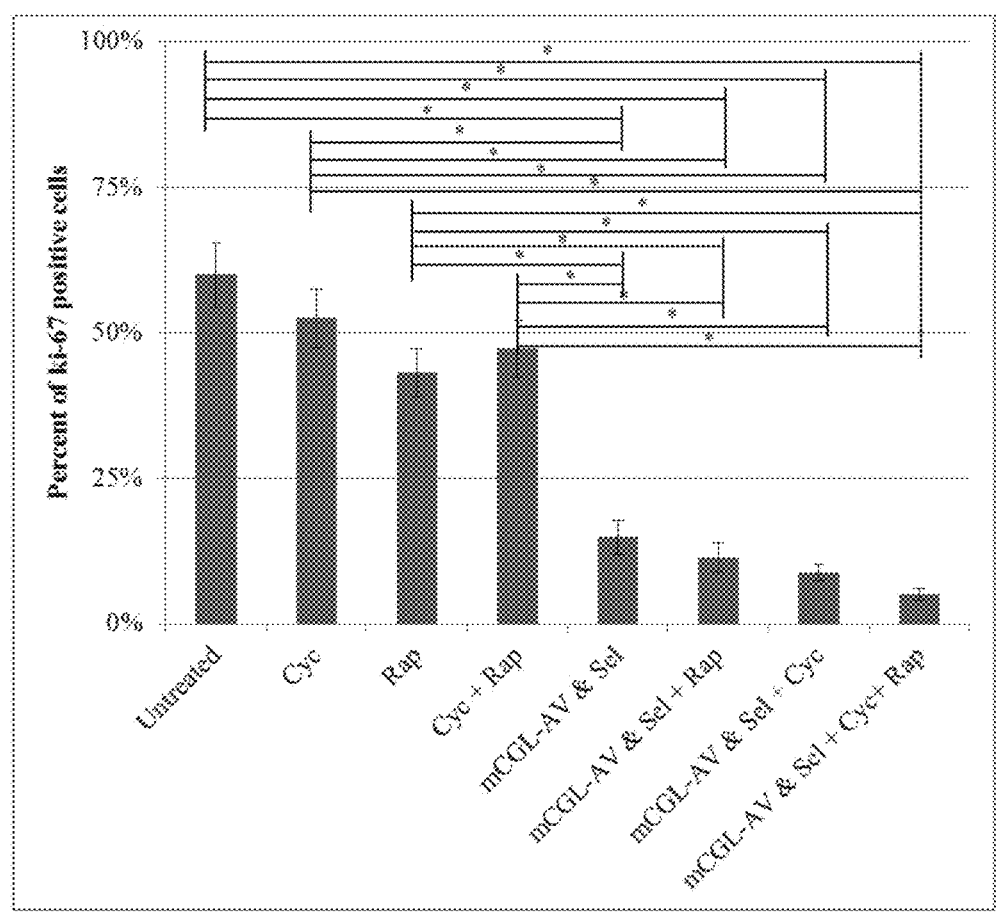
FIG. 12 shows results demonstrating that enzyme prodrug treatment causes decreased staining of proliferation marker ki-67. A Nikon Eclipse E800 compound microscope was used to capture 15 fields of view of tumor sections from 3 mice per group (necrotic tumor cores were excluded). Immunostaining staining for ki-67 was quantified as percent of cells (hematoxylin counterstain) with DAB and is presented as mean±SE. Statistical significance between groups is indicated by * (p<0.001).

Staining for ki-67, a common marker for proliferative activity, displayed the inverse trend of that observed with activated caspase-3, as anticipated. The quantification of ki-67 staining is presented in FIG. 12. Based on the data showing increased levels of apoptosis in mCGL-AV and selenomethionine treated groups, decreased levels of proliferation in the enzyme prodrug treated groups are unsurprising.

Figure 13:
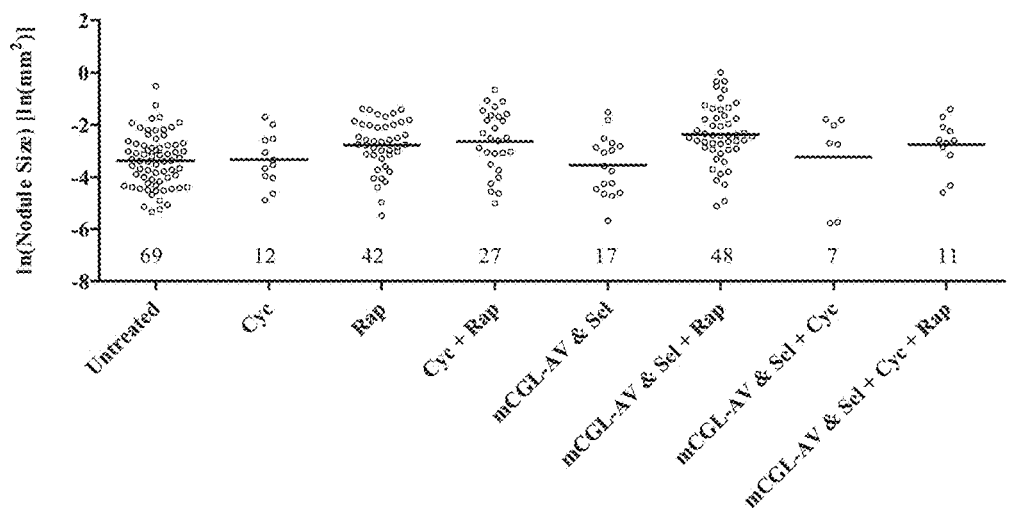
FIG. 13 demonstrates that enzyme prodrug treatments with cyclophosphamide included reduces the number of lung metastasis in 4T1-TdTomato BALB/c mouse model. A Leica stereomicroscope with an automated ImageJ macro was used to quantify fluorescent nodules in the lung. Data is shown as individual nodules from the lungs of 3 mice per group after 3 weeks of treatment on a log-normal scale, as the nodule sizes were logarithmically distributed. Median nodule size on the log scale is marked. Total nodules per group (n=3 mice) is summed and shown.

Metastatic progression is hypothesized as the primary cause of death in the mice bearing 4T1 mammary tumors; hence, determination of the presence of metastatic nodules holds predictive therapeutic value. Individual metastatic nodules on the lungs of tumor bearing mice are graphically presented as a function of nodule size with nodule quantities summarized in FIG. 13. A logarithmic scale is utilized for the graphical display of metastatic nodules as the sizes are fairly normally distributed on the logarithmic scale, explained by the expected exponential growth of the cells at the metastatic sites. The quantities of metastatic nodules observed for each experimental group correlate well with the observed survival data.

Cyclophosphamide provides clear benefit through reduced numbers of metastases. The enzyme prodrug therapy also shows reduced numbers and size of metastatic nodules. Rapamycin by itself, however, exhibits only a minimal benefit regarding metastatic size or quantity. When rapamycin is combined with the enzyme prodrug therapy, metastatic progression is actually enhanced compared to the enzyme prodrug therapy alone, contrary to the observed survival data. Enhanced metastatic formation with rapamycin, likely a result of its immunosuppressive properties, can be attenuated with a reduced dose (reduction from 5 mg/kg to 1.5 mg/kg eliminated metastatic progression, though the antitumor effect at reduced dose is unreported). Fortunately, rapamycin does not act in an antagonistic manner with cyclophosphamide, and the complete combination of rapamycin, cyclophosphamide, and mCGL-AV and selenomethionine resulted overall in a strong reduction of metastatic nodules.

Figure 14:
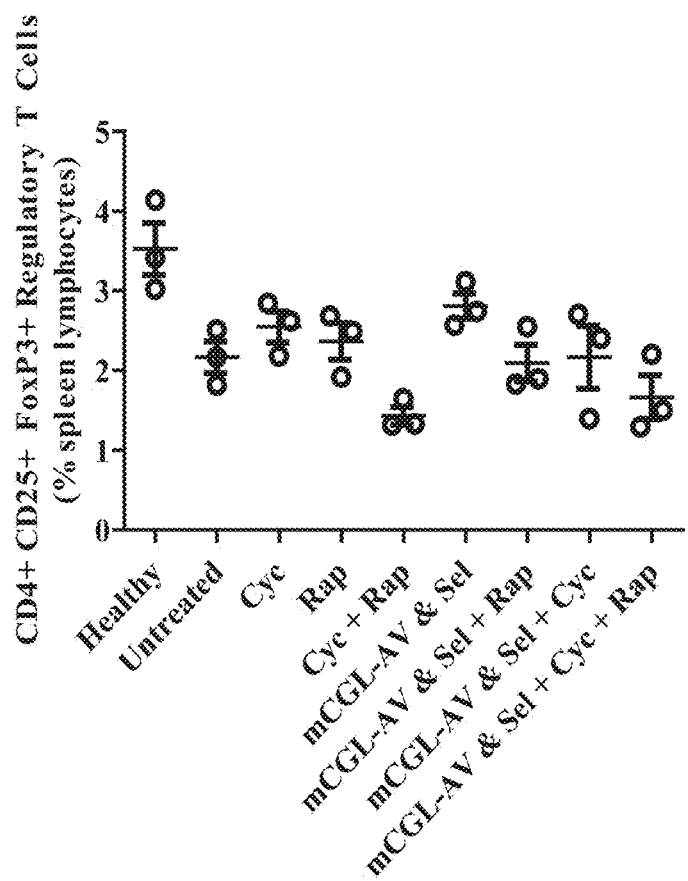
FIG. 14 demonstrates the effects of combination enzyme prodrug treatments on regulatory T cell levels in the spleen. CD4+ CD25+ FoxP3+ regulatory T cell levels were quantified with flow cytometry and are presented as a percentage of spleen lymphocytes in BALB/c mice with 4T1 grafts after 3 weeks of treatment or healthy BALB/c mice with no tumor. Data is mean±SE (n=3 mice). Statistical significance was observed compared with healthy mice, but no statistical significance was observed between groups bearing tumors.

To determine whether cyclophosphamide's anti-metastatic activity was a result of reduced regulatory T cells, flow cytometry of the spleens of the mice was performed. The quantification of the regulatory T cell levels is shown in FIG. 14. A drastic reduction in regulatory T cell levels upon cyclophosphamide treatment was not observed. In comparing the mCGL-AV& Sel, mCGL-AV & Sel+Cyc, and mCGL-AV & Sel+Cyc+Rap levels (the experimental groups presented with similar levels of metastases and in a similar state of health at the time of data collection), cyclophosphamide did cause a mild reduction in regulatory T cell levels.

Figure 15:
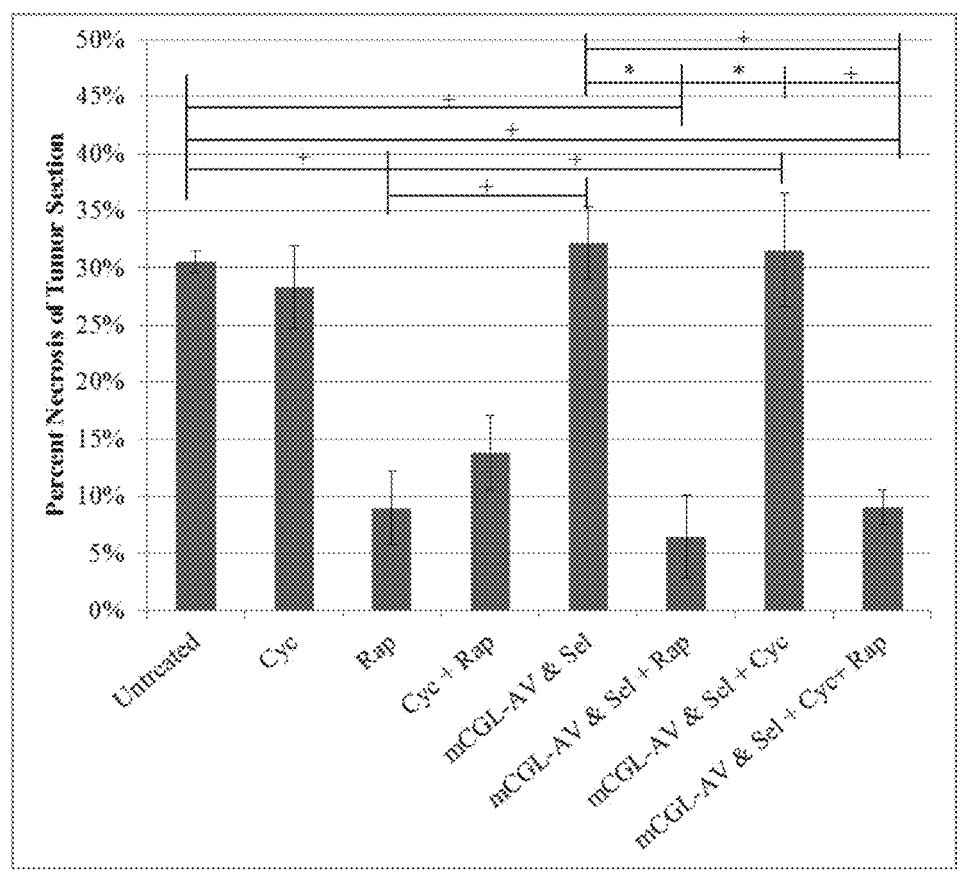
FIG. 15 shows that Rapamycin with enzyme prodrug treatment reduces percent necrosis in 4T1 tumor sections. Necrotic regions were determined from hematoxylin and eosin stained tumor sections and quantified from whole section images of mice sacrificed after 3 weeks of treatment. Data is presented as mean±SE (n=3 mice). Statistical significance between groups is indicated by +(p<0.01) or * (p<0.001).

Intratumoral hypoxia frequently results in necrotic tumor cores, particularly with in vivo models bearing tumor grafts. Some degree of coagulative necrosis was apparent in tumor sections from all treated and untreated groups, with the quantification shown in FIG. 15. The fast-growing and aggressiveness of the 4T1 mammary tumors results in high necrotic percentages in untreated tumors as the tumor mass outgrows its blood supply. The targeted mCGL-AV enzyme prodrug therapy may be expected to actually increase necrosis, since it is shown to reduce tumor blood flow; however, minimal increase of necrotic percentage compared to untreated mice was observed. Reduced necrosis in tumor sections treated with rapamycin is unsurprising given the role of mTOR in preventing tumor necrosis factor-α (TNF-α) related necrosis, potentially through the inhibition of TNF-α production.

Figure 16:
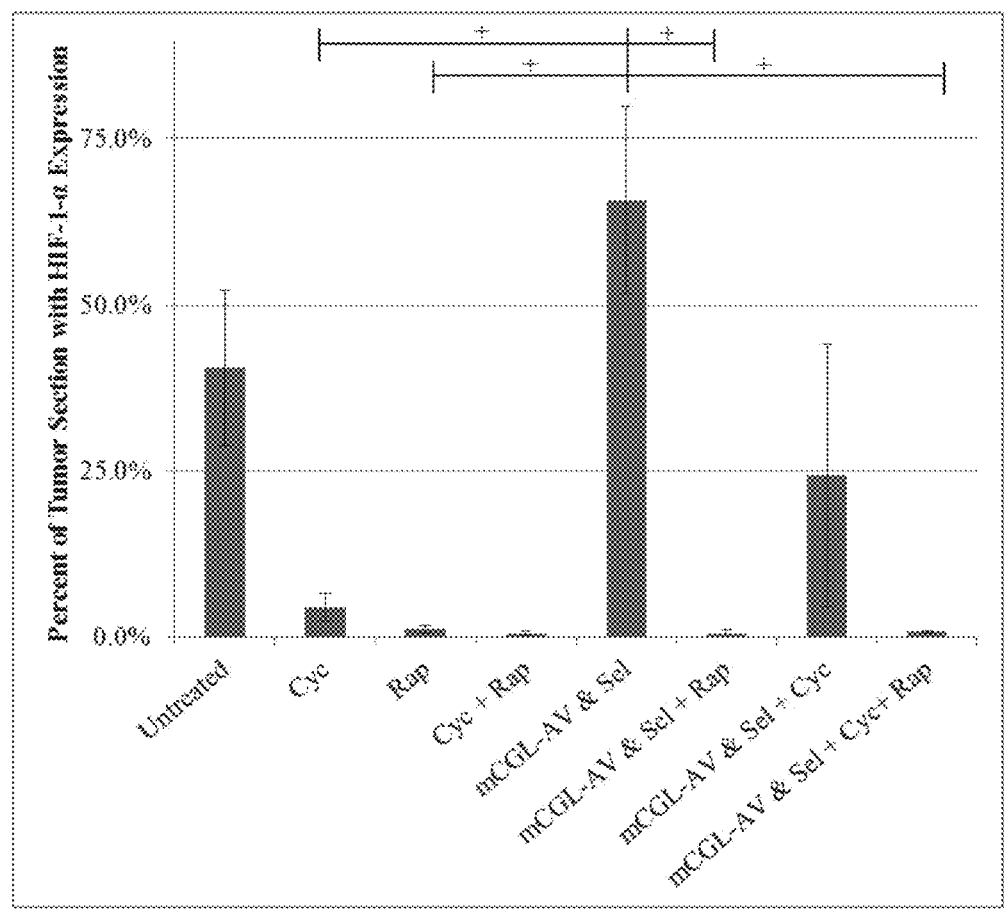
FIG. 16 shows that Rapamycin with enzyme prodrug treatment reduces percent of tumor expressing hypoxia-inducible factor-1 alpha (HIF-1-α). Immunohistochemistry staining of HIF-1-α with DAB development was quantified from whole section images of mice sacrificed after 3 weeks of treatment. Data is presented as mean±SE (n=3 mice). Statistical significance between groups is indicated by +(p<0.01) or * (p<0.001).

The primary intended downstream target of mTOR inhibition with rapamycin and the main controller of the hypoxic response is HIF-1-α. Necrosis is a strong indicator of hypoxia and the subsequent enhanced expression of HIF-1-α, which is expected to be highest in the surrounding viable cancer tissue. Quantification of HIF-1-α staining of tumor sections is shown in FIG. 16. The decreased levels of HIF-1-α in rapamycin-treated mice correlate with the observed decreased necrotic region, as anticipated. Unexpectedly, low dose cyclophosphamide also resulted in a drastic reduction of HIF-1-α expression in the tumor sections. The effect was not as pronounced when combined with the enzyme prodrug therapy, though results were variable. The results show that rapamycin reduced the percentage of 4T1 tumors expressing HIF-1α in BALB/c mice. Without wishing to be bound by theory, this finding appears to validate that rapamycin is inhibiting the synthesis of HIF-1α.

Synergism

The definition of drug synergy can be vague and application dependent, though in general an enhanced effect achieved through the combination of two compounds beyond the sum of the two effects is considered superadditive or synergistic. Assessment of drug synergy is typically approached using different variations of the Bliss independence and Loewe additivity models. The Bliss independence model is more relevant for examination of treatment effect enhancement and applies to mechanistically independent combination approaches. Alternatively, the Loewe additivity model applies more directly to competing compounds and efforts towards dose reduction.

The implication of synergism of the combination therapy as opposed to purely additive effects stems from the design of the combination therapy in which each therapeutic component acts upon separate mechanisms and pathways. The full combination therapy (mCGL-AV with selenomethionine, cyclophosphamide, and rapamycin) is a three-pronged anticancer approach that introduces targeted cytotoxicity to promote tumor death, immune stimulation for reduction of metastases, and attenuation of the hypoxic response to prevent tumor regrowth. The primary means for evaluating treatment efficacy, survival, and tumor volume, and the independent mechanisms of drug action implicate the Bliss independence approach as the most relevant methodology to analyze potential synergism.

Using this approach, the predicted response of a combination therapy can be achieved using the additivity of probability theory for independent mechanisms (A and B) which can be applied to inhibition of tumor growth using the equation below. The predicted percent inhibition of a combination therapy is determined using the experimentally observed percent inhibitions of the combination therapy constituents.

$$\text{Predicted}_{\%\ Inhibition} = A_{\%\ Inhibition} + B_{\%\ Inhibition} - A_{\%\ Inhibition} * B_{\%\ Inhibition}$$

Subtracting the predicted effect value from the actual observed value generates a "synergism assessment factor", adapted to simply define synergism as values greater than 0, additive effects equal to 0, and antagonistic effects less than 0. For example, to evaluate the synergism of selenomethionine with mCGL-AV, the measured values for tumor growth percent inhibition at a determined time point for mCGL-AV alone and for selenomethionine alone would replace A and B in the above equation. That calculated value would then be subtracted from the measured value for the selenomethionine and mCGL-AV group to obtain the synergism assessment factor. Table 8 displays the synergism assessment factors for the different combinations for the first two weeks of treatment, after which the values become skewed by plateaued tumor volumes of untreated mice rapidly reaching the end points of the study. The ampersand indicates grouped components, and the plus sign indicates the separation of the constituents undergoing evaluation for synergism. For example, "mCGL-AV+Sel" represents the evaluation of mCGL-AV and selenomethionine for synergism, whereas the other representation "mCGL-AV & Sel" classifies the enzyme prodrug therapy as its own constituent to provide a stronger comparison for the evaluation of rapamycin and cyclophosphamide synergism.

TABLE 8

Synergism assessment factors for tumor growth inhibition

| | Day of Treatment | | | | |
|---|---|---|---|---|---|
| | 0 | 2 | 6 | 9 | 13 |
| Rap + Cyc | 0.00 | −0.03 | 0.06 | −0.10 | −0.02 |
| mCGL-AV + Sel | 0.00 | 0.12 | 0.07 | 0.06 | 0.04 |
| mCGL-AV & Sel + Rap | 0.00 | −0.23 | 0.10 | 0.06 | 0.20 |
| mCGL-AV & Sel + Cyc | 0.00 | 0.09 | −0.01 | 0.00 | 0.12 |
| mCGL-AV & Sel + Rap & Cyc | 0.00 | −0.03 | 0.07 | 0.15 | 0.19 |

Evaluation of tumor growth inhibition at the conclusion of the treatment period using the Bliss independence model for synergy indicates that combination of the mCGL-AV enzyme prodrug system with rapamycin produced a synergistic effect. The mCGL-AV system combined with rapamycin and cyclophosphamide also exhibits synergism compared to the effects of the enzyme prodrug system alone and rapamycin and cyclophosphamide effects together. Cyclophosphamide combined with the enzyme prodrug treatment does not have a synergistic effect on inhibition of tumor growth. The combination of rapamycin and cyclophosphamide without the enzyme prodrug therapy is also not synergistic. Strong synergism of mCGL-AV and selenomethionine was apparent through the duration of the treatment.

The synergistic effect on tumor growth inhibition exhibited by the combination of rapamycin with the enzyme prodrug therapy likely results from the cytotoxic effect of the enzyme prodrug therapy combined with the inhibition of the hypoxic response by rapamycin. Alone, rapamycin reduces HIF-1 expression as expected; however, it is only through its combination with the enzyme prodrug therapy that a significant inhibition of tumor growth occurs. The enzyme prodrug therapy alone does achieve tumor growth inhibition; however, continuous regrowth of cancer cells, presumably increased through the hypoxic response, contributes to the eventual progression of the tumor. Enzyme prodrug therapy-related killing of the tumor cells combined with the modulation of tumor regrowth resulting from rapamycin inhibition of the hypoxic response produce the synergistic effect on tumor growth inhibition.

The theorized utility of the enzyme prodrug combination with cyclophosphamide is an enhancement of mouse survival through reduction of pulmonary metastases by stimulating the immune system. Hence, a lack of synergistic inhibition of tumor growth with cyclophosphamide and the enzyme prodrug therapy is unsurprising. Evaluation of primary tumor growth is a standard strategy for the evaluation of an antitumor therapy; however, survival is a function of metastatic formation in addition to tumor growth. Metastatic formation is perhaps a more vital indicator of treatment efficacy, as evidenced by the enhanced survival with cyclophosphamide and cyclophosphamide combination therapies and the related reduction in metastases. The synergistic antitumor effect of rapamycin with the enzyme prodrug therapy produces an enhanced survival as anticipated but does not, however, significantly reduce metastatic formation. Further enhancement of survival with the enzyme prodrug therapy combined with rapamycin and cyclophosphamide occurs as a result of the antitumor growth effects as well as metastatic reductions. The total combined advantage is not obvious and, in fact, opposes the reasonable theory that rapamycin, an immunosuppressive drug, would have an antagonistic effect when combined with cyclophosphamide used at immunostimulatory doses.

Thus, in accordance with the presently disclosed inventive concepts, there have been provided enzyme conjugate and prodrug compositions, as well as kits containing same and methods of producing and utilizing same that fully satisfy the objectives and advantages set forth hereinabove. Although the presently disclosed inventive concepts have been described in conjunction with the specific drawings, experimentation, results and language set forth hereinabove, it is evident that many alternatives, modifications, and variations will be apparent to those skilled in the art. Accordingly, it is intended to embrace all such alternatives, modifications and variations that fall within the spirit and broad scope of the presently disclosed inventive concepts.

What is claimed is:

1. A method of treating a cancerous tumor in a subject, comprising:
   administering to the subject a therapeutically-effective amount of an enzyme conjugate comprising a variant cystathione-gamma-lyase (CGL) enzyme conjugated to a ligand, wherein the variant CGL enzyme has L-methioninase activity, and wherein (1) the variant CGL enzyme is at least 95% identical to SEQ ID NO:1 and comprises amino acid substitutions at amino acid positions 58, 118, and 338 thereof, or is at least 95% identical to SEQ ID NO:2 and comprises amino acid substitutions at amino acid positions 59, 119, and 339 thereof, (2) the ligand has the ability to specifically and stably bind to at least one of an external receptor and a binding site on an outer surface of an endothelial cell of a tumor vasculature of the cancerous tumor, wherein the ligand is an annexin, and (3) the at least one of an external receptor and a binding site is specific to the endothelial cells of the tumor vasculature;
   administering a therapeutically-effective amount of a prodrug which is a substrate for the variant CGL enzyme, wherein the prodrug is converted within the tumor vasculature to an active anticancer drug by the variant CGL enzyme at the site of the endothelial cell to which the enzyme conjugate is bound, thereby reducing and/or inhibiting growth of the cancerous tumor by killing the endothelial cells of the tumor vasculature, and wherein the prodrug comprises a selenomethionine prodrug; and
   administering a therapeutically-effective amount of a hypoxia-inducible factor-1 (HIF-1) inhibitor, wherein the HIF-1 inhibitor is a mechanistic target of rapamycin (mTOR) inhibitor, and wherein the mTOR inhibitor is selected from the group consisting of rapamycin, everolimus, temsirolimus, ridaforolimus, tacrolimus, ABT-578, AP23675, AP-23841, 7-epi-rapamycin, 7-thiomethyl-rapamycin, 7-epi-tromethoxyphenyyl-rapamycin, 7-epi-thiomethyl-rapamycin, 7-demethoxy-rapamycin, 32-demethoxy-rapamycin, 7-desmethyl-rapamycin, and 42-O-(2-hydroxy) ethyl-rapamycin.

2. The method of claim 1, wherein unbound enzyme conjugate is allowed to be cleared from bloodstream of the subject before the prodrug is administered.

3. The method of claim 1, further comprising administering a therapeutically-effective amount of an immunostimulant to the subject.

4. A kit, comprising:
   an enzyme conjugate comprising a variant cystathione-gamma-lyase (CGL) enzyme conjugated to a ligand, wherein the variant CGL enzyme has L-methioninase activity, and wherein (1) the variant CGL enzyme is at least 95% identical to SEQ ID NO:1 and comprises amino acid substitutions at amino acid positions 58, 118, and 338 thereof, or is at least 94% 95% identical to SEQ ID NO:2 and comprises amino acid substitutions at amino acid positions 59, 119, and 339 thereof, (2) the ligand has the ability to specifically and stably bind to at least one of an external receptor and a binding site on an outer surface of an endothelial cell of a tumor vasculature of the cancerous tumor, wherein the ligand is an annexin, and (3) the at least one of an external receptor and a binding site is specific to the endothelial cells of the tumor vasculature;
   a prodrug cleavable by the variant CGL enzyme, wherein the prodrug comprises a selenomethionine prodrug; and
   a hypoxia-inducible factor-1 (HIF-1) inhibitor, wherein the HIF-1 inhibitor is a mechanistic target of rapamycin (mTOR) inhibitor, and wherein the mTOR inhibitor is selected from the group consisting of rapamycin, everolimus, temsirolimus, ridaforolimus, tacrolimus, ABT-578, AP23675, AP-23841, 7-epi-rapamycin, 7-thiomethyl-rapamycin, 7-epi-tromethoxyphenyyl-rapamycin, 7-epi-thiomethyl-rapamycin, 7-demethoxy-rapamycin, 32-demethoxy-rapamycin, 7-desmethyl-rapamycin, and 42-O-(2-hydroxy) ethyl-rapamycin.

5. The kit of claim 4, further comprising an immunostimulant.

6. The method of claim 1, wherein the variant CGL enzyme and the ligand are directly coupled together.

7. The method of claim 1, wherein the variant CGL enzyme and the ligand are indirectly coupled together via a linker.

8. The method of claim 1, wherein the enzyme conjugate further comprises polyethylene glycol (PEG).

9. The kit of claim 4, wherein the variant CGL enzyme and the ligand are directly coupled together.

10. The kit of claim 4, wherein the variant CGL enzyme and the ligand are indirectly coupled together via a linker.

11. The kit of claim 4, wherein the enzyme conjugate further comprises polyethylene glycol (PEG).

* * * * *

SEQUENCE LISTING

<160> NUMBER OF SEQ ID NOS: 13

<210> SEQ ID NO 1
<211> LENGTH: 398
<212> TYPE: PRT
<213> ORGANISM: Mus musculus

<400> SEQUENCE: 1

Met Gln Lys Asp Ala Ser Leu Ser Gly Phe Leu Pro Ser Phe Gln His
1               5                   10                  15

Phe Ala Thr Gln Ala Ile His Val Gly Gln Glu Pro Glu Gln Trp Asn
                20                  25                  30

Ser Arg Ala Val Val Leu Pro Ile Ser Leu Ala Thr Thr Phe Lys Gln
            35                  40                  45

Asp Phe Pro Gly Gln Ser Ser Gly Phe Glu Tyr Ser Arg Ser Gly Asn
    50                  55                  60

Pro Thr Arg Asn Cys Leu Glu Lys Ala Val Ala Ala Leu Asp Gly Ala
65                  70                  75                  80

Lys His Ser Leu Ala Phe Ala Ser Gly Leu Ala Ala Thr Ile Thr Ile
                85                  90                  95

Thr His Leu Leu Lys Ala Gly Asp Glu Ile Ile Cys Met Asp Glu Val
            100                 105                 110

Tyr Gly Gly Thr Asn Arg Tyr Phe Arg Arg Val Ala Ser Glu Phe Gly
            115                 120                 125

Leu Lys Ile Ser Phe Val Asp Cys Ser Lys Thr Lys Leu Leu Glu Ala
    130                 135                 140

Ala Ile Thr Pro Gln Thr Lys Leu Val Trp Ile Glu Thr Pro Thr Asn
145                 150                 155                 160

Pro Thr Leu Lys Leu Ala Asp Ile Gly Ala Cys Ala Gln Ile Val His
                165                 170                 175

Lys Arg Gly Asp Ile Ile Leu Val Val Asp Asn Thr Phe Met Ser Ala
            180                 185                 190

Tyr Phe Gln Arg Pro Leu Ala Leu Gly Ala Asp Ile Cys Met Cys Ser
    195                 200                 205

Ala Thr Lys Tyr Met Asn Gly His Ser Asp Val Val Met Gly Leu Val
210                 215                 220

Ser Val Asn Ser Asp Asp Leu Asn Ser Arg Leu Arg Phe Leu Gln Asn
225                 230                 235                 240

Ser Leu Gly Ala Val Pro Ser Pro Phe Asp Cys Tyr Leu Cys Cys Arg
            245                 250                 255

Gly Leu Lys Thr Leu Gln Val Arg Met Glu Lys His Phe Lys Asn Gly
            260                 265                 270

Met Ala Val Ala Arg Phe Leu Glu Thr Asn Pro Arg Val Glu Lys Val
            275                 280                 285

Val Tyr Pro Gly Leu Pro Ser His Pro Gln His Glu Leu Ala Lys Arg
    290                 295                 300

Gln Cys Ser Gly Cys Pro Gly Met Val Ser Phe Tyr Ile Lys Gly Ala
305                 310                 315                 320

Leu Gln His Ala Lys Ala Phe Leu Lys Asn Leu Lys Leu Phe Thr Leu
                325                 330                 335

Ala Glu Ser Leu Gly Gly Tyr Glu Ser Leu Ala Glu Leu Pro Ala Ile
            340                 345                 350

Met Thr His Ala Ser Val Pro Glu Lys Asp Arg Ala Thr Leu Gly Ile
            355                 360                 365

Asn Asp Thr Leu Ile Arg Leu Ser Val Gly Leu Glu Asp Glu Gln Asp
    370                 375                 380

Leu Leu Glu Asp Leu Asp Arg Ala Leu Lys Ala Ala His Pro
385                 390                 395

<210> SEQ ID NO 2
<211> LENGTH: 405

<212> TYPE: PRT
<213> ORGANISM: Homo sapiens

<400> SEQUENCE: 2

```
Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
            20                  25                  30

Thr Ser Arg Ala Val Val Pro Pro Ile Ser Leu Ser Thr Thr Phe Lys
        35                  40                  45

Gln Gly Ala Pro Gly Gln His Ser Gly Phe Glu Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Arg Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335

Leu Ala Glu Ser Leu Gly Gly Phe Glu Ser Leu Ala Glu Leu Pro Ala
            340                 345                 350

Ile Met Thr His Ala Ser Val Leu Lys Asn Asp Arg Asp Val Leu Gly
        355                 360                 365

Ile Ser Asp Thr Leu Ile Arg Leu Ser Val Gly Leu Glu Asp Glu Glu
    370                 375                 380

Asp Leu Leu Glu Asp Leu Asp Gln Ala Leu Lys Ala Ala His Pro Pro
385                 390                 395                 400
```

Ser Gly Ser His Ser
            405

<210> SEQ ID NO 3
<211> LENGTH: 398
<212> TYPE: PRT
<213> ORGANISM: Mus musculus

<400> SEQUENCE: 3

Met Gln Lys Asp Ala Ser Leu Ser Gly Phe Leu Pro Ser Phe Gln His
1               5                   10                  15

Phe Ala Thr Gln Ala Ile His Val Gly Gln Glu Pro Glu Gln Trp Asn
            20                  25                  30

Ser Arg Ala Val Val Leu Pro Ile Ser Leu Ala Thr Thr Phe Lys Gln
        35                  40                  45

Asp Phe Pro Gly Gln Ser Ser Gly Phe Asn Tyr Ser Arg Ser Gly Asn
    50                  55                  60

Pro Thr Arg Asn Cys Leu Glu Lys Ala Val Ala Ala Leu Asp Gly Ala
65                  70                  75                  80

Lys His Ser Leu Ala Phe Ala Ser Gly Leu Ala Ala Thr Ile Thr Ile
                85                  90                  95

Thr His Leu Leu Lys Ala Gly Asp Glu Ile Ile Cys Met Asp Glu Val
            100                 105                 110

Tyr Gly Gly Thr Asn Leu Tyr Phe Arg Arg Val Ala Ser Glu Phe Gly
        115                 120                 125

Leu Lys Ile Ser Phe Val Asp Cys Ser Lys Thr Lys Leu Leu Glu Ala
130                 135                 140

Ala Ile Thr Pro Gln Thr Lys Leu Val Trp Ile Glu Thr Pro Thr Asn
145                 150                 155                 160

Pro Thr Leu Lys Leu Ala Asp Ile Gly Ala Cys Ala Gln Ile Val His
                165                 170                 175

Lys Arg Gly Asp Ile Ile Leu Val Val Asp Asn Thr Phe Met Ser Ala
            180                 185                 190

Tyr Phe Gln Arg Pro Leu Ala Leu Gly Ala Asp Ile Cys Met Cys Ser
        195                 200                 205

Ala Thr Lys Tyr Met Asn Gly His Ser Asp Val Val Met Gly Leu Val
210                 215                 220

Ser Val Asn Ser Asp Asp Leu Asn Ser Arg Leu Arg Phe Leu Gln Asn
225                 230                 235                 240

Ser Leu Gly Ala Val Pro Ser Pro Phe Asp Cys Tyr Leu Cys Cys Arg
                245                 250                 255

Gly Leu Lys Thr Leu Gln Val Arg Met Glu Lys His Phe Lys Asn Gly
            260                 265                 270

Met Ala Val Ala Arg Phe Leu Glu Thr Asn Pro Arg Val Glu Lys Val
        275                 280                 285

Val Tyr Pro Gly Leu Pro Ser His Pro Gln His Glu Leu Ala Lys Arg
290                 295                 300

Gln Cys Ser Gly Cys Pro Gly Met Val Ser Phe Tyr Ile Lys Gly Ala
305                 310                 315                 320

Leu Gln His Ala Lys Ala Phe Leu Lys Asn Leu Lys Leu Phe Thr Leu
                325                 330                 335

Ala Val Ser Leu Gly Gly Tyr Glu Ser Leu Ala Glu Leu Pro Ala Ile
            340                 345                 350

Met Thr His Ala Ser Val Pro Glu Lys Asp Arg Ala Thr Leu Gly Ile

```
                355                 360                 365
Asn Asp Thr Leu Ile Arg Leu Ser Val Gly Leu Glu Asp Glu Gln Asp
370                 375                 380

Leu Leu Glu Asp Leu Asp Arg Ala Leu Lys Ala Ala His Pro
385                 390                 395

<210> SEQ ID NO 4
<211> LENGTH: 405
<212> TYPE: PRT
<213> ORGANISM: Homo sapiens

<400> SEQUENCE: 4

Met Gln Glu Lys Asp Ala Ser Ser Gln Gly Phe Leu Pro His Phe Gln
1               5                   10                  15

His Phe Ala Thr Gln Ala Ile His Val Gly Gln Asp Pro Glu Gln Trp
                20                  25                  30

Thr Ser Arg Ala Val Val Pro Ile Ser Leu Ser Thr Thr Phe Lys
        35                  40                  45

Gln Gly Ala Pro Gly Gln His Ser Gly Phe Asn Tyr Ser Arg Ser Gly
    50                  55                  60

Asn Pro Thr Arg Asn Cys Leu Glu Lys Ala Val Ala Ala Leu Asp Gly
65                  70                  75                  80

Ala Lys Tyr Cys Leu Ala Phe Ala Ser Gly Leu Ala Ala Thr Val Thr
                85                  90                  95

Ile Thr His Leu Leu Lys Ala Gly Asp Gln Ile Ile Cys Met Asp Asp
            100                 105                 110

Val Tyr Gly Gly Thr Asn Leu Tyr Phe Arg Gln Val Ala Ser Glu Phe
        115                 120                 125

Gly Leu Lys Ile Ser Phe Val Asp Cys Ser Lys Ile Lys Leu Leu Glu
    130                 135                 140

Ala Ala Ile Thr Pro Glu Thr Lys Leu Val Trp Ile Glu Thr Pro Thr
145                 150                 155                 160

Asn Pro Thr Gln Lys Val Ile Asp Ile Glu Gly Cys Ala His Ile Val
                165                 170                 175

His Lys His Gly Asp Ile Ile Leu Val Val Asp Asn Thr Phe Met Ser
            180                 185                 190

Pro Tyr Phe Gln Arg Pro Leu Ala Leu Gly Ala Asp Ile Ser Met Tyr
        195                 200                 205

Ser Ala Thr Lys Tyr Met Asn Gly His Ser Asp Val Val Met Gly Leu
    210                 215                 220

Val Ser Val Asn Cys Glu Ser Leu His Asn Arg Leu Arg Phe Leu Gln
225                 230                 235                 240

Asn Ser Leu Gly Ala Val Pro Ser Pro Ile Asp Cys Tyr Leu Cys Asn
                245                 250                 255

Arg Gly Leu Lys Thr Leu His Val Arg Met Glu Lys His Phe Lys Asn
            260                 265                 270

Gly Met Ala Val Ala Gln Phe Leu Glu Ser Asn Pro Trp Val Glu Lys
        275                 280                 285

Val Ile Tyr Pro Gly Leu Pro Ser His Pro Gln His Glu Leu Val Lys
    290                 295                 300

Arg Gln Cys Thr Gly Cys Thr Gly Met Val Thr Phe Tyr Ile Lys Gly
305                 310                 315                 320

Thr Leu Gln His Ala Glu Ile Phe Leu Lys Asn Leu Lys Leu Phe Thr
                325                 330                 335
```

```
Leu Ala Val Ser Leu Gly Gly Phe Glu Ser Leu Ala Glu Leu Pro Ala
                340                 345                 350

Ile Met Thr His Ala Ser Val Leu Lys Asn Asp Arg Asp Val Leu Gly
            355                 360                 365

Ile Ser Asp Thr Leu Ile Arg Leu Ser Val Gly Leu Glu Asp Glu Glu
        370                 375                 380

Asp Leu Leu Glu Asp Leu Asp Gln Ala Leu Lys Ala Ala His Pro Pro
385                 390                 395                 400

Ser Gly Ser His Ser
                405

<210> SEQ ID NO 5
<211> LENGTH: 319
<212> TYPE: PRT
<213> ORGANISM: Homo sapiens

<400> SEQUENCE: 5

Met Ala Thr Arg Gly Thr Val Thr Asp Phe Pro Gly Phe Asp Gly Arg
1               5                   10                  15

Ala Asp Ala Glu Val Leu Arg Lys Ala Met Lys Gly Leu Gly Thr Asp
            20                  25                  30

Glu Asp Ser Ile Leu Asn Leu Leu Thr Ser Arg Ser Asn Ala Gln Arg
        35                  40                  45

Gln Glu Ile Ala Gln Glu Phe Lys Thr Leu Phe Gly Arg Asp Leu Val
    50                  55                  60

Asp Asp Leu Lys Ser Glu Leu Thr Gly Lys Phe Glu Lys Leu Ile Val
65                  70                  75                  80

Ala Met Met Lys Pro Ser Arg Leu Tyr Asp Ala Tyr Glu Leu Lys His
                85                  90                  95

Ala Leu Lys Gly Ala Gly Thr Asp Glu Lys Val Leu Thr Glu Ile Ile
            100                 105                 110

Ala Ser Arg Thr Pro Glu Glu Leu Ser Ala Ile Lys Gln Val Tyr Glu
        115                 120                 125

Glu Glu Tyr Gly Ser Asn Leu Glu Asp Asp Val Val Gly Asp Thr Ser
    130                 135                 140

Gly Tyr Tyr Gln Arg Met Leu Val Val Leu Leu Gln Ala Asn Arg Asp
145                 150                 155                 160

Pro Asp Thr Ala Ile Asp Asp Ala Gln Val Glu Leu Asp Ala Gln Ala
                165                 170                 175

Leu Phe Gln Ala Gly Glu Leu Lys Trp Gly Thr Asp Glu Glu Lys Phe
            180                 185                 190

Ile Thr Ile Phe Gly Thr Arg Ser Val Ser His Leu Arg Arg Val Phe
        195                 200                 205

Asp Lys Tyr Met Thr Ile Ser Gly Phe Gln Ile Glu Glu Thr Ile Asp
    210                 215                 220

Arg Glu Thr Ser Gly Asn Leu Glu Gln Leu Leu Leu Ala Val Val Lys
225                 230                 235                 240

Ser Ile Arg Ser Ile Pro Ala Tyr Leu Ala Glu Thr Leu Tyr Tyr Ala
                245                 250                 255

Met Lys Gly Ala Gly Thr Asp Asp His Thr Leu Ile Arg Val Val Val
            260                 265                 270

Ser Arg Ser Glu Ile Asp Leu Phe Asn Ile Arg Lys Glu Phe Arg Lys
        275                 280                 285

Asn Phe Ala Thr Ser Leu Tyr Ser Met Ile Lys Gly Asp Thr Ser Gly
    290                 295                 300
```

```
Asp Tyr Lys Lys Ala Leu Leu Leu Leu Cys Gly Gly Glu Asp Asp
305                 310                 315
```

<210> SEQ ID NO 6
<211> LENGTH: 346
<212> TYPE: PRT
<213> ORGANISM: Homo sapiens

<400> SEQUENCE: 6

```
Met Ala Met Val Ser Glu Phe Leu Lys Gln Ala Arg Phe Leu Glu Asn
1               5                   10                  15

Gln Glu Gln Glu Tyr Val Gln Ala Val Lys Ser Tyr Lys Gly Gly Pro
            20                  25                  30

Gly Ser Ala Val Ser Pro Tyr Pro Ser Phe Asn Val Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Thr Asn Ala Gln Arg Gln Gln Ile
65                  70                  75                  80

Lys Ala Ala Tyr Leu Gln Glu Asn Gly Lys Pro Leu Asp Glu Val Leu
                85                  90                  95

Arg Lys Ala Leu Thr Gly His Leu Glu Glu Val Val Leu Ala Met Leu
            100                 105                 110

Lys Thr Pro Ala Gln Phe Asp Ala Asp Glu Leu Arg Gly Ala Met Lys
        115                 120                 125

Gly Leu Gly Thr Asp Glu Asp Thr Leu Ile Glu Ile Leu Thr Thr Arg
130                 135                 140

Ser Asn Glu Gln Ile Arg Glu Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Lys Ala Leu Leu Ala Leu Ala Lys Gly Asp Arg Cys Gln Asp Leu
            180                 185                 190

Ser Val Asn Gln Asp Leu Ala Asp Thr Asp Ala Arg Ala Leu Tyr Glu
        195                 200                 205

Ala Gly Glu Arg Arg Lys Gly Thr Asp Val Asn Val Phe Thr Thr Ile
210                 215                 220

Leu Thr Ser Arg Ser Phe Pro His Leu Arg Arg Val Phe Gln Asn Tyr
225                 230                 235                 240

Gly Lys Tyr Ser Gln His Asp Met Asn Lys Ala Leu Asp Leu Glu Leu
                245                 250                 255

Lys Gly Asp Ile Glu Lys Cys Leu Thr Thr Ile Val Lys Cys Ala Thr
            260                 265                 270

Ser Thr Pro Ala Phe Phe Ala Glu Lys Leu Tyr Glu Ala Met Lys Gly
        275                 280                 285

Ala Gly Thr Arg His Lys Ala Leu Ile Arg Ile Met Val Ser Arg Ser
290                 295                 300

Glu Ile Asp Met Asn Glu Ile Lys Val Phe Tyr Gln Lys Lys Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345
```

<210> SEQ ID NO 7
<211> LENGTH: 10
<212> TYPE: PRT
<213> ORGANISM: Artificial sequence
<220> FEATURE:
<223> OTHER INFORMATION: synthetic peptide

<400> SEQUENCE: 7

```
Cys Thr Thr His Trp Gly Phe Thr Leu Cys
1               5                   10
```

<210> SEQ ID NO 8
<211> LENGTH: 779
<212> TYPE: PRT
<213> ORGANISM: artificial sequence
<220> FEATURE:
<223> OTHER INFORMATION: pre-cleavage amino acid sequence of the mCGL-AV
      fusion protein

<400> SEQUENCE: 8

```
Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Met Leu Glu Val Leu
        35                  40                  45

Phe Gln Gly Pro Met Gln Lys Asp Ala Ser Leu Ser Gly Phe Leu Pro
    50                  55                  60

Ser Phe Gln His Phe Ala Thr Gln Ala Ile His Val Gly Gln Glu Pro
65                  70                  75                  80

Glu Gln Trp Asn Ser Arg Ala Val Val Leu Pro Ile Ser Leu Ala Thr
                85                  90                  95

Thr Phe Lys Gln Asp Phe Pro Gly Gln Ser Ser Gly Phe Asn Tyr Ser
            100                 105                 110

Arg Ser Gly Asn Pro Thr Arg Asn Cys Leu Glu Lys Ala Val Ala Ala
        115                 120                 125

Leu Asp Gly Ala Lys His Ser Leu Ala Phe Ala Ser Gly Leu Ala Ala
    130                 135                 140

Thr Ile Thr Ile Thr His Leu Leu Lys Ala Gly Asp Glu Ile Ile Cys
145                 150                 155                 160

Met Asp Glu Val Tyr Gly Gly Thr Asn Leu Tyr Phe Arg Arg Val Ala
                165                 170                 175

Ser Glu Phe Gly Leu Lys Ile Ser Phe Val Asp Cys Ser Lys Thr Lys
            180                 185                 190

Leu Leu Glu Ala Ala Ile Thr Pro Gln Thr Lys Leu Val Trp Ile Glu
        195                 200                 205

Thr Pro Thr Asn Pro Thr Leu Lys Leu Ala Asp Ile Gly Ala Cys Ala
    210                 215                 220

Gln Ile Val His Lys Arg Gly Asp Ile Ile Leu Val Val Asp Asn Thr
225                 230                 235                 240

Phe Met Ser Ala Tyr Phe Gln Arg Pro Leu Ala Leu Gly Ala Asp Ile
                245                 250                 255

Cys Met Cys Ser Ala Thr Lys Tyr Met Asn Gly His Ser Asp Val Val
            260                 265                 270

Met Gly Leu Val Ser Val Asn Ser Asp Asp Leu Asn Ser Arg Leu Arg
        275                 280                 285

Phe Leu Gln Asn Ser Leu Gly Ala Val Pro Ser Pro Phe Asp Cys Tyr
    290                 295                 300
```

```
Leu Cys Cys Arg Gly Leu Lys Thr Leu Gln Val Arg Met Glu Lys His
305                 310                 315                 320

Phe Lys Asn Gly Met Ala Val Ala Arg Phe Leu Glu Thr Asn Pro Arg
                325                 330                 335

Val Glu Lys Val Val Tyr Pro Gly Leu Pro Ser His Pro Gln His Glu
            340                 345                 350

Leu Ala Lys Arg Gln Cys Ser Gly Cys Pro Gly Met Val Ser Phe Tyr
                355                 360                 365

Ile Lys Gly Ala Leu Gln His Ala Lys Ala Phe Leu Lys Asn Leu Lys
370                 375                 380

Leu Phe Thr Leu Ala Val Ser Leu Gly Gly Tyr Glu Ser Leu Ala Glu
385                 390                 395                 400

Leu Pro Ala Ile Met Thr His Ala Ser Val Pro Glu Lys Asp Arg Ala
                405                 410                 415

Thr Leu Gly Ile Asn Asp Thr Leu Ile Arg Leu Ser Val Gly Leu Glu
            420                 425                 430

Asp Glu Gln Asp Leu Leu Glu Asp Leu Asp Arg Ala Leu Lys Ala Ala
                435                 440                 445

His Pro Ser Gly Gly Gly Ser Gly Gly Gly Met Ala Thr Arg
450                 455                 460

Gly Thr Val Thr Asp Phe Pro Gly Phe Asp Gly Arg Ala Asp Ala Glu
465                 470                 475                 480

Val Leu Arg Lys Ala Met Lys Gly Leu Gly Thr Asp Glu Asp Ser Ile
                485                 490                 495

Leu Asn Leu Leu Thr Ser Arg Ser Asn Ala Gln Arg Gln Glu Ile Ala
            500                 505                 510

Gln Glu Phe Lys Thr Leu Phe Gly Arg Asp Leu Val Asp Asp Leu Lys
                515                 520                 525

Ser Glu Leu Thr Gly Lys Phe Glu Lys Leu Ile Val Ala Met Met Lys
530                 535                 540

Pro Ser Arg Leu Tyr Asp Ala Tyr Glu Leu Lys His Ala Leu Lys Gly
545                 550                 555                 560

Ala Gly Thr Asp Glu Lys Val Leu Thr Glu Ile Ala Ser Arg Thr
                565                 570                 575

Pro Glu Glu Leu Ser Ala Ile Lys Gln Val Tyr Glu Glu Tyr Gly
                580                 585                 590

Ser Asn Leu Glu Asp Asp Val Val Gly Asp Thr Ser Gly Tyr Tyr Gln
            595                 600                 605

Arg Met Leu Val Val Leu Leu Gln Ala Asn Arg Asp Pro Asp Thr Ala
        610                 615                 620

Ile Asp Asp Ala Gln Val Glu Leu Asp Ala Gln Ala Leu Phe Gln Ala
625                 630                 635                 640

Gly Glu Leu Lys Trp Gly Thr Asp Glu Glu Lys Phe Ile Thr Ile Phe
                645                 650                 655

Gly Thr Arg Ser Val Ser His Leu Arg Arg Val Phe Asp Lys Tyr Met
                660                 665                 670

Thr Ile Ser Gly Phe Gln Ile Glu Glu Thr Ile Asp Arg Glu Thr Ser
            675                 680                 685

Gly Asn Leu Glu Gln Leu Leu Leu Ala Val Val Lys Ser Ile Arg Ser
        690                 695                 700

Ile Pro Ala Tyr Leu Ala Glu Thr Leu Tyr Tyr Ala Met Lys Gly Ala
705                 710                 715                 720
```

```
Gly Thr Asp Asp His Thr Leu Ile Arg Val Val Ser Arg Ser Glu
                725                 730                 735

Ile Asp Leu Phe Asn Ile Arg Lys Glu Phe Arg Lys Asn Phe Ala Thr
            740                 745                 750

Ser Leu Tyr Ser Met Ile Lys Gly Asp Thr Ser Gly Asp Tyr Lys Lys
        755                 760                 765

Ala Leu Leu Leu Leu Cys Gly Gly Glu Asp Asp
    770                 775

<210> SEQ ID NO 9
<211> LENGTH: 806
<212> TYPE: PRT
<213> ORGANISM: artificial sequence
<220> FEATURE:
<223> OTHER INFORMATION: pre-cleavage amino acid sequence of the mCGL-AI
      fusion protein

<400> SEQUENCE: 9

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
                20                  25                  30

Ser Pro Asp Leu Gly Thr Asp Asp Asp Lys Met Leu Glu Val Leu
            35                  40                  45

Phe Gln Gly Pro Met Gln Lys Asp Ala Ser Leu Ser Gly Phe Leu Pro
50                  55                  60

Ser Phe Gln His Phe Ala Thr Gln Ala Ile His Val Gly Gln Glu Pro
65                  70                  75                  80

Glu Gln Trp Asn Ser Arg Ala Val Val Leu Pro Ile Ser Leu Ala Thr
                85                  90                  95

Thr Phe Lys Gln Asp Phe Pro Gly Gln Ser Ser Gly Phe Asn Tyr Ser
            100                 105                 110

Arg Ser Gly Asn Pro Thr Arg Asn Cys Leu Glu Lys Ala Val Ala Ala
        115                 120                 125

Leu Asp Gly Ala Lys His Ser Leu Ala Phe Ala Ser Gly Leu Ala Ala
    130                 135                 140

Thr Ile Thr Ile Thr His Leu Leu Lys Ala Gly Asp Glu Ile Ile Cys
145                 150                 155                 160

Met Asp Glu Val Tyr Gly Gly Thr Asn Leu Tyr Phe Arg Arg Val Ala
                165                 170                 175

Ser Glu Phe Gly Leu Lys Ile Ser Phe Val Asp Cys Ser Lys Thr Lys
            180                 185                 190

Leu Leu Glu Ala Ala Ile Thr Pro Gln Thr Lys Leu Val Trp Ile Glu
        195                 200                 205

Thr Pro Thr Asn Pro Thr Leu Lys Leu Ala Asp Ile Gly Ala Cys Ala
    210                 215                 220

Gln Ile Val His Lys Arg Gly Asp Ile Ile Leu Val Val Asp Asn Thr
225                 230                 235                 240

Phe Met Ser Ala Tyr Phe Gln Arg Pro Leu Ala Leu Gly Ala Asp Ile
                245                 250                 255

Cys Met Cys Ser Ala Thr Lys Tyr Met Asn Gly His Ser Asp Val Val
            260                 265                 270

Met Gly Leu Val Ser Val Asn Ser Asp Asp Leu Asn Ser Arg Leu Arg
        275                 280                 285

Phe Leu Gln Asn Ser Leu Gly Ala Val Pro Ser Pro Phe Asp Cys Tyr
    290                 295                 300
```

```
Leu Cys Cys Arg Gly Leu Lys Thr Leu Gln Val Arg Met Glu Lys His
305                 310                 315                 320

Phe Lys Asn Gly Met Ala Val Ala Arg Phe Leu Glu Thr Asn Pro Arg
            325                 330                 335

Val Glu Lys Val Val Tyr Pro Gly Leu Pro Ser His Pro Gln His Glu
        340                 345                 350

Leu Ala Lys Arg Gln Cys Ser Gly Cys Pro Gly Met Val Ser Phe Tyr
            355                 360                 365

Ile Lys Gly Ala Leu Gln His Ala Lys Ala Phe Leu Lys Asn Leu Lys
370                 375                 380

Leu Phe Thr Leu Ala Val Ser Leu Gly Gly Tyr Glu Ser Leu Ala Glu
385                 390                 395                 400

Leu Pro Ala Ile Met Thr His Ala Ser Val Pro Glu Lys Asp Arg Ala
                405                 410                 415

Thr Leu Gly Ile Asn Asp Thr Leu Ile Arg Leu Ser Val Gly Leu Glu
            420                 425                 430

Asp Glu Gln Asp Leu Leu Glu Asp Leu Asp Arg Ala Leu Lys Ala Ala
                435                 440                 445

His Pro Ser Gly Gly Gly Ser Gly Gly Gly Met Ala Met Val
            450                 455                 460

Ser Glu Phe Leu Lys Gln Ala Arg Phe Leu Glu Asn Gln Glu Gln Glu
465                 470                 475                 480

Tyr Val Gln Ala Val Lys Ser Tyr Lys Gly Pro Gly Ser Ala Val
                485                 490                 495

Ser Pro Tyr Pro Ser Phe Asn Val Ser Ser Asp Val Ala Ala Leu His
            500                 505                 510

Lys Ala Ile Met Val Lys Gly Val Asp Glu Ala Thr Ile Ile Asp Ile
            515                 520                 525

Leu Thr Lys Arg Thr Asn Ala Gln Arg Gln Gln Ile Lys Ala Ala Tyr
530                 535                 540

Leu Gln Glu Asn Gly Lys Pro Leu Asp Glu Val Leu Arg Lys Ala Leu
545                 550                 555                 560

Thr Gly His Leu Glu Glu Val Val Leu Ala Met Leu Lys Thr Pro Ala
                565                 570                 575

Gln Phe Asp Ala Asp Glu Leu Arg Gly Ala Met Lys Gly Leu Gly Thr
            580                 585                 590

Asp Glu Asp Thr Leu Ile Glu Ile Leu Thr Thr Arg Ser Asn Glu Gln
            595                 600                 605

Ile Arg Glu Ile Asn Arg Val Tyr Arg Glu Glu Leu Lys Arg Asp Leu
            610                 615                 620

Ala Lys Asp Ile Thr Ser Asp Thr Ser Gly Asp Phe Arg Lys Ala Leu
625                 630                 635                 640

Leu Ala Leu Ala Lys Gly Asp Arg Cys Gln Asp Leu Ser Val Asn Gln
                645                 650                 655

Asp Leu Ala Asp Thr Asp Ala Arg Ala Leu Tyr Glu Ala Gly Glu Arg
            660                 665                 670

Arg Lys Gly Thr Asp Val Asn Val Phe Thr Thr Ile Leu Thr Ser Arg
            675                 680                 685

Ser Phe Pro His Leu Arg Arg Val Phe Gln Asn Tyr Gly Lys Tyr Ser
            690                 695                 700

Gln His Asp Met Asn Lys Ala Leu Asp Leu Glu Leu Lys Gly Asp Ile
705                 710                 715                 720
```

```
Glu Lys Cys Leu Thr Thr Ile Val Lys Cys Ala Ser Thr Pro Ala
                725                 730                 735

Phe Phe Ala Glu Lys Leu Tyr Glu Ala Met Lys Gly Ala Gly Thr Arg
            740                 745                 750

His Lys Ala Leu Ile Arg Ile Met Val Ser Arg Ser Glu Ile Asp Met
            755                 760                 765

Asn Glu Ile Lys Val Phe Tyr Gln Lys Lys Tyr Gly Ile Ser Leu Cys
            770                 775                 780

Gln Ala Ile Leu Asp Glu Thr Lys Gly Asp Tyr Glu Lys Ile Leu Val
785                 790                 795                 800

Ala Leu Cys Gly Gly Asn
                805
```

<210> SEQ ID NO 10
<211> LENGTH: 729
<212> TYPE: PRT
<213> ORGANISM: artificial sequence
<220> FEATURE:
<223> OTHER INFORMATION: post-cleavage amino acid sequence of the mCGL-AV fusion protein

<400> SEQUENCE: 10

```
Gly Pro Met Gln Lys Asp Ala Ser Leu Ser Gly Phe Leu Pro Ser Phe
1               5                   10                  15

Gln His Phe Ala Thr Gln Ala Ile His Val Gly Gln Glu Pro Glu Gln
            20                  25                  30

Trp Asn Ser Arg Ala Val Val Leu Pro Ile Ser Leu Ala Thr Thr Phe
            35                  40                  45

Lys Gln Asp Phe Pro Gly Gln Ser Ser Gly Phe Asn Tyr Ser Arg Ser
50                  55                  60

Gly Asn Pro Thr Arg Asn Cys Leu Glu Lys Ala Val Ala Ala Leu Asp
65                  70                  75                  80

Gly Ala Lys His Ser Leu Ala Phe Ala Ser Gly Leu Ala Ala Thr Ile
            85                  90                  95

Thr Ile Thr His Leu Leu Lys Ala Gly Asp Glu Ile Ile Cys Met Asp
            100                 105                 110

Glu Val Tyr Gly Gly Thr Asn Leu Tyr Phe Arg Arg Val Ala Ser Glu
        115                 120                 125

Phe Gly Leu Lys Ile Ser Phe Val Asp Cys Ser Lys Thr Lys Leu Leu
    130                 135                 140

Glu Ala Ala Ile Thr Pro Gln Thr Lys Leu Val Trp Ile Glu Thr Pro
145                 150                 155                 160

Thr Asn Pro Thr Leu Lys Leu Ala Asp Ile Gly Ala Cys Ala Gln Ile
            165                 170                 175

Val His Lys Arg Gly Asp Ile Ile Leu Val Val Asp Asn Thr Phe Met
            180                 185                 190

Ser Ala Tyr Phe Gln Arg Pro Leu Ala Leu Gly Ala Asp Ile Cys Met
        195                 200                 205

Cys Ser Ala Thr Lys Tyr Met Asn Gly His Ser Asp Val Val Met Gly
    210                 215                 220

Leu Val Ser Val Asn Ser Asp Asp Leu Asn Ser Arg Leu Arg Phe Leu
225                 230                 235                 240

Gln Asn Ser Leu Gly Ala Val Pro Ser Pro Phe Asp Cys Tyr Leu Cys
            245                 250                 255

Cys Arg Gly Leu Lys Thr Leu Gln Val Arg Met Glu Lys His Phe Lys
            260                 265                 270
```

```
Asn Gly Met Ala Val Ala Arg Phe Leu Glu Thr Asn Pro Arg Val Glu
        275                 280                 285

Lys Val Val Tyr Pro Gly Leu Pro Ser His Pro Gln His Glu Leu Ala
        290                 295                 300

Lys Arg Gln Cys Ser Gly Cys Pro Gly Met Val Ser Phe Tyr Ile Lys
305                 310                 315                 320

Gly Ala Leu Gln His Ala Lys Ala Phe Leu Lys Asn Leu Lys Leu Phe
                    325                 330                 335

Thr Leu Ala Val Ser Leu Gly Gly Tyr Glu Ser Leu Ala Glu Leu Pro
                340                 345                 350

Ala Ile Met Thr His Ala Ser Val Pro Glu Lys Asp Arg Ala Thr Leu
                355                 360                 365

Gly Ile Asn Asp Thr Leu Ile Arg Leu Ser Val Gly Leu Glu Asp Glu
        370                 375                 380

Gln Asp Leu Leu Glu Asp Leu Asp Arg Ala Leu Lys Ala Ala His Pro
385                 390                 395                 400

Ser Gly Gly Gly Gly Ser Gly Gly Gly Met Ala Thr Arg Gly Thr
                    405                 410                 415

Val Thr Asp Phe Pro Gly Phe Asp Gly Arg Ala Asp Ala Glu Val Leu
                420                 425                 430

Arg Lys Ala Met Lys Gly Leu Gly Thr Asp Glu Asp Ser Ile Leu Asn
                435                 440                 445

Leu Leu Thr Ser Arg Ser Asn Ala Gln Arg Gln Glu Ile Ala Gln Glu
        450                 455                 460

Phe Lys Thr Leu Phe Gly Arg Asp Leu Val Asp Asp Leu Lys Ser Glu
465                 470                 475                 480

Leu Thr Gly Lys Phe Glu Lys Leu Ile Val Ala Met Met Lys Pro Ser
                    485                 490                 495

Arg Leu Tyr Asp Ala Tyr Glu Leu Lys His Ala Leu Lys Gly Ala Gly
                500                 505                 510

Thr Asp Glu Lys Val Leu Thr Glu Ile Ile Ala Ser Arg Thr Pro Glu
                515                 520                 525

Glu Leu Ser Ala Ile Lys Gln Val Tyr Glu Glu Glu Tyr Gly Ser Asn
        530                 535                 540

Leu Glu Asp Asp Val Val Gly Asp Thr Ser Gly Tyr Tyr Gln Arg Met
545                 550                 555                 560

Leu Val Val Leu Leu Gln Ala Asn Arg Asp Pro Asp Thr Ala Ile Asp
                    565                 570                 575

Asp Ala Gln Val Glu Leu Asp Ala Gln Ala Leu Phe Gln Ala Gly Glu
                580                 585                 590

Leu Lys Trp Gly Thr Asp Glu Glu Lys Phe Ile Thr Ile Phe Gly Thr
                595                 600                 605

Arg Ser Val Ser His Leu Arg Arg Val Phe Asp Lys Tyr Met Thr Ile
        610                 615                 620

Ser Gly Phe Gln Ile Glu Glu Thr Ile Asp Arg Glu Thr Ser Gly Asn
625                 630                 635                 640

Leu Glu Gln Leu Leu Leu Ala Val Val Lys Ser Ile Arg Ser Ile Pro
                    645                 650                 655

Ala Tyr Leu Ala Glu Thr Leu Tyr Tyr Ala Met Lys Gly Ala Gly Thr
                660                 665                 670

Asp Asp His Thr Leu Ile Arg Val Val Ser Arg Ser Glu Ile Asp
                675                 680                 685
```

-continued

```
Leu Phe Asn Ile Arg Lys Glu Phe Arg Lys Asn Phe Ala Thr Ser Leu
    690                 695                 700

Tyr Ser Met Ile Lys Gly Asp Thr Ser Gly Asp Tyr Lys Lys Ala Leu
705                 710                 715                 720

Leu Leu Leu Cys Gly Gly Glu Asp Asp
                725
```

<210> SEQ ID NO 11
<211> LENGTH: 756
<212> TYPE: PRT
<213> ORGANISM: artificial sequence
<220> FEATURE:
<223> OTHER INFORMATION: post-cleavage amino acid sequence of the
      mCGL-AV fusion protein

<400> SEQUENCE: 11

```
Gly Pro Met Gln Lys Asp Ala Ser Leu Ser Gly Phe Leu Pro Ser Phe
1               5                   10                  15

Gln His Phe Ala Thr Gln Ala Ile His Val Gly Gln Glu Pro Glu Gln
            20                  25                  30

Trp Asn Ser Arg Ala Val Val Leu Pro Ile Ser Leu Ala Thr Thr Phe
        35                  40                  45

Lys Gln Asp Phe Pro Gly Gln Ser Ser Gly Phe Asn Tyr Ser Arg Ser
    50                  55                  60

Gly Asn Pro Thr Arg Asn Cys Leu Glu Lys Ala Val Ala Ala Leu Asp
65                  70                  75                  80

Gly Ala Lys His Ser Leu Ala Phe Ala Ser Gly Leu Ala Ala Thr Ile
                85                  90                  95

Thr Ile Thr His Leu Leu Lys Ala Gly Asp Glu Ile Ile Cys Met Asp
            100                 105                 110

Glu Val Tyr Gly Gly Thr Asn Leu Tyr Phe Arg Arg Val Ala Ser Glu
        115                 120                 125

Phe Gly Leu Lys Ile Ser Phe Val Asp Cys Ser Lys Thr Lys Leu Leu
    130                 135                 140

Glu Ala Ala Ile Thr Pro Gln Thr Lys Leu Val Trp Ile Glu Thr Pro
145                 150                 155                 160

Thr Asn Pro Thr Leu Lys Leu Ala Asp Ile Gly Ala Cys Ala Gln Ile
                165                 170                 175

Val His Lys Arg Gly Asp Ile Ile Leu Val Val Asp Asn Thr Phe Met
            180                 185                 190

Ser Ala Tyr Phe Gln Arg Pro Leu Ala Leu Gly Ala Asp Ile Cys Met
        195                 200                 205

Cys Ser Ala Thr Lys Tyr Met Asn Gly His Ser Asp Val Val Met Gly
    210                 215                 220

Leu Val Ser Val Asn Ser Asp Asp Leu Asn Ser Arg Leu Arg Phe Leu
225                 230                 235                 240

Gln Asn Ser Leu Gly Ala Val Pro Ser Pro Phe Asp Cys Tyr Leu Cys
                245                 250                 255

Cys Arg Gly Leu Lys Thr Leu Gln Val Arg Met Glu Lys His Phe Lys
            260                 265                 270

Asn Gly Met Ala Val Ala Arg Phe Leu Glu Thr Asn Pro Arg Val Glu
        275                 280                 285

Lys Val Val Tyr Pro Gly Leu Pro Ser His Pro Gln His Glu Leu Ala
    290                 295                 300

Lys Arg Gln Cys Ser Gly Cys Pro Gly Met Val Ser Phe Tyr Ile Lys
305                 310                 315                 320
```

-continued

```
Gly Ala Leu Gln His Ala Lys Ala Phe Leu Lys Asn Leu Lys Leu Phe
                325                 330                 335
Thr Leu Ala Val Ser Leu Gly Gly Tyr Glu Ser Leu Ala Glu Leu Pro
            340                 345                 350
Ala Ile Met Thr His Ala Ser Val Pro Glu Lys Asp Arg Ala Thr Leu
        355                 360                 365
Gly Ile Asn Asp Thr Leu Ile Arg Leu Ser Val Gly Leu Glu Asp Glu
    370                 375                 380
Gln Asp Leu Leu Glu Asp Leu Asp Arg Ala Leu Lys Ala Ala His Pro
385                 390                 395                 400
Ser Gly Gly Gly Ser Gly Gly Gly Met Ala Met Val Ser Glu
                405                 410                 415
Phe Leu Lys Gln Ala Arg Phe Leu Glu Asn Gln Glu Gln Glu Tyr Val
                420                 425                 430
Gln Ala Val Lys Ser Tyr Lys Gly Gly Pro Gly Ser Ala Val Ser Pro
                435                 440                 445
Tyr Pro Ser Phe Asn Val Ser Ser Asp Val Ala Ala Leu His Lys Ala
            450                 455                 460
Ile Met Val Lys Gly Val Asp Glu Ala Thr Ile Ile Asp Ile Leu Thr
465                 470                 475                 480
Lys Arg Thr Asn Ala Gln Arg Gln Gln Ile Lys Ala Ala Tyr Leu Gln
                485                 490                 495
Glu Asn Gly Lys Pro Leu Asp Glu Val Leu Arg Lys Ala Leu Thr Gly
                500                 505                 510
His Leu Glu Glu Val Val Leu Ala Met Leu Lys Thr Pro Ala Gln Phe
            515                 520                 525
Asp Ala Asp Glu Leu Arg Gly Ala Met Lys Gly Leu Gly Thr Asp Glu
            530                 535                 540
Asp Thr Leu Ile Glu Ile Leu Thr Thr Arg Ser Asn Glu Gln Ile Arg
545                 550                 555                 560
Glu Ile Asn Arg Val Tyr Arg Glu Glu Leu Lys Arg Asp Leu Ala Lys
                565                 570                 575
Asp Ile Thr Ser Asp Thr Ser Gly Asp Phe Arg Lys Ala Leu Leu Ala
            580                 585                 590
Leu Ala Lys Gly Asp Arg Cys Gln Asp Leu Ser Val Asn Gln Asp Leu
            595                 600                 605
Ala Asp Thr Asp Ala Arg Ala Leu Tyr Glu Ala Gly Glu Arg Arg Lys
610                 615                 620
Gly Thr Asp Val Asn Val Phe Thr Thr Ile Leu Thr Ser Arg Ser Phe
625                 630                 635                 640
Pro His Leu Arg Arg Val Phe Gln Asn Tyr Gly Lys Tyr Ser Gln His
                645                 650                 655
Asp Met Asn Lys Ala Leu Asp Leu Glu Leu Lys Gly Asp Ile Glu Lys
                660                 665                 670
Cys Leu Thr Thr Ile Val Lys Cys Ala Thr Ser Thr Pro Ala Phe Phe
            675                 680                 685
Ala Glu Lys Leu Tyr Glu Ala Met Lys Gly Ala Gly Thr Arg His Lys
        690                 695                 700
Ala Leu Ile Arg Ile Met Val Ser Arg Ser Glu Ile Asp Met Asn Glu
705                 710                 715                 720
Ile Lys Val Phe Tyr Gln Lys Lys Tyr Gly Ile Ser Leu Cys Gln Ala
                725                 730                 735
```

Ile Leu Asp Glu Thr Lys Gly Asp Tyr Glu Lys Ile Leu Val Ala Leu
             740                 745                 750

Cys Gly Gly Asn
        755

<210> SEQ ID NO 12
<211> LENGTH: 2421
<212> TYPE: DNA
<213> ORGANISM: artificial sequence
<220> FEATURE:
<223> OTHER INFORMATION: DNA sequence of the mCGL-AI fusion gene
      including sequencing primer

<400> SEQUENCE: 12

| | | | | | |
|---|---|---|---|---|---|
| atgcaccatc | atcatcatca | ttcttctggt | ctggtgccac | gcggttctgg | tatgaaagaa     60 |
| accgctgctg | ctaaattcga | acgccagcac | atggacagcc | agatctgggt | accgatgac     120 |
| gacgacaaga | tgctggaagt | tctgttccag | ggtccgatgc | agaaagacgc | gagcctgtct    180 |
| ggcttcctgc | cgtcttttca | gcacttcgca | actcaggcga | tccacgttgg | tcaggagcct    240 |
| gaacaatgga | actctcgtgc | ggttgttctg | ccgatcagcc | tcgccacgac | cttcaaacag    300 |
| gatttcccgg | tcagtcttc  | tggtttcaac | tactcccgtt | ctggcaatcc | gacccgtaac    360 |
| tgcctggaaa | aagcggtagc | cgcgctggac | ggtgcgaaac | actctctggc | gttcgcctct    420 |
| ggtctcgcgg | cgaccatcac | gatcacccat | ctgctcaagg | ccggtgacga | aatcatctgt    480 |
| atggacgaag | tttacggtgg | caccaacctg | tattttcgtc | gtgttgcgtc | tgaattcggt    540 |
| ctgaaaatct | ctttcgttga | ctgctctaaa | accaaactcc | tggaggcagc | aattactccg    600 |
| cagacgaaac | tcgtttggat | cgaaaccccg | accaacccga | ccctgaagct | cgccgacatc    660 |
| ggtgcgtgcg | ctcaaatcgt | tcacaaacgt | ggtgacatca | tcctggttgt | tgataatacc    720 |
| ttcatgtctg | cgtactttca | gcgtccgctg | gcgctgggcg | ctgacatctg | catgtgctcc    780 |
| gcgaccaaat | acatgaacgg | tcactctgac | gtagttatgg | gtctggttag | cgttaacagc    840 |
| gacgatctca | attcccgcct | gcgtttcctg | cagaactccc | tcggcgcagt | accgtccccg    900 |
| ttcgactgct | atctctgctg | ccgtggtctc | aaaacgctgc | aggttcgtat | ggaaaagcat    960 |
| ttcaagaacg | gtatggcggt | ggcgcgcttc | ctcgaaacga | accgcgtgt  | tgaaaaagtt   1020 |
| gtttaccctg | gcctcccgtc | ccacccgcag | cacgaactgg | cgaaacgtca | gtgctctggt   1080 |
| tgccctggca | tggtttcctt | ctacatcaaa | ggtgccctcc | agcacgcgaa | agccttcctg   1140 |
| aaaaacctga | aactgttcac | cctcgcggtt | tctctgggtg | gttacgaatc | tctcgctgaa   1200 |
| ctgccggcga | tcatgaccca | cgcttctgta | cctgaaaaag | accgtgcgac | cctcggtatc   1260 |
| aacgataccc | tgatccgtct | gtctgttggt | ctggaggacg | aacaggacct | gctggaagac   1320 |
| ctggatcgtg | ctctcaaagc | ggcgcacccg | agcggtggtg | gtggtagtgg | tggcggtggt   1380 |
| atggcaatgg | ttagcgaatt | tctgaaacag | gcacgttttc | tggaaaacca | agaacaagaa   1440 |
| tatgttcagg | ccgtgaaaag | ctataaaggt | ggtccgggta | cgcagttag  | cccgtatccg   1500 |
| agctttaatg | ttagcagtga | tgttgcagca | ctgcataaag | ccattatggt | taaaggtgtt   1560 |
| gatgaagcca | ccatcattga | tattctgacc | aaacgtacca | atgcacagcg | tcagcagatt   1620 |
| aaagcagcat | atctgcaaga | aaatggtaaa | ccgctggatg | aagttctgcg | taaagcactg   1680 |
| acaggtcatc | tggaagaggt | tgttctggca | atgctgaaaa | caccggcaca | gtttgatgca   1740 |
| gatgaactgc | gtggtgcaat | gaaaggtctg | gcaccgatg  | aagatacact | gattgaaatc   1800 |
| ctgaccaccc | gtagcaatga | gcagattcgt | gaaattaatc | gtgtgtatcg | cgaagaactg   1860 |

|   |   |   |   |   |   |
|---|---|---|---|---|---|
| aaacgtgatc | tggcaaaaga | tatcaccagc | gataccagcg | gtgattttcg | taaagccctg | 1920 |
| ctggcactgg | ccaaaggtga | tcgttgtcag | gatctgagcg | ttaaccagga | tctggcagat | 1980 |
| accgatgcac | gtgccctgta | tgaagccggt | gagcgtcgta | aaggtactga | tgtgaacgtt | 2040 |
| ttcactacga | ttctgacctc | ccgttctttc | ccgcatctcc | gtcgtgtgtt | ccagaactat | 2100 |
| ggtaagtact | ctcagcacga | catgaacaaa | gcgctggacc | tggaactcaa | aggtgacatt | 2160 |
| gaaaagtgcc | tcaccaccat | cgttaaatgc | gcgacctcta | cccctgcttt | cttcgcggaa | 2220 |
| aaactgtatg | aggccatgaa | gggtgcgggc | actcgtcaca | aggctctgat | ccgtattatg | 2280 |
| gtttcccgta | gcgagattga | tatgaacgaa | attaaggttt | tctaccagaa | aaagtacggt | 2340 |
| atcagcctgt | gccaggcgat | cctggacgaa | accaaaggcg | actacgaaaa | gattctggtt | 2400 |
| gcgctgtgcg | gtggtaactg | a |   |   |   | 2421 |

<210> SEQ ID NO 13
<211> LENGTH: 2340
<212> TYPE: DNA
<213> ORGANISM: artificial sequence
<220> FEATURE:
<223> OTHER INFORMATION: DNA sequence of the mCGL-AV fusion gene (SEQ ID NO:13) including sequencing primer

<400> SEQUENCE: 13

|   |   |   |   |   |   |
|---|---|---|---|---|---|
| atgcaccatc | atcatcatca | ttcttctggt | ctggtgccac | gcggttctgg | tatgaaagaa | 60 |
| accgctgctg | ctaaattcga | acgccagcac | atggacagcc | cagatctggg | taccgatgac | 120 |
| gacgacaaga | tgctggaagt | tctgttccag | ggtccgatgc | agaaagacgc | gagcctgtct | 180 |
| ggcttcctgc | cgtcttttca | gcacttcgca | actcaggcga | tccacgttgg | tcaggagcct | 240 |
| gaacaatgga | actctcgtgc | ggttgttctg | ccgatcagcc | tcgccacgac | cttcaaacag | 300 |
| gatttcccgg | gtcagtcttc | tggtttcaac | tactcccgtt | ctggcaatcc | gacccgtaac | 360 |
| tgcctggaaa | aagcggtagc | cgcgctggac | ggtgcgaaac | actctctggc | gttcgcctct | 420 |
| ggtctcgcgg | cgaccatcac | gatcacccat | ctgctcaagg | ccggtgacga | aatcatctgt | 480 |
| atggacgaag | tttacggtgg | caccaacctg | tattttcgtc | gtgttgcgtc | tgaattcggt | 540 |
| ctgaaaatct | ctttcgttga | ctgctctaaa | accaaactcc | tggaggcagc | aattactccg | 600 |
| cagacgaaac | tcgtttggat | cgaaacccg | accaacccga | ccctgaagct | cgccgacatc | 660 |
| ggtgcgtgcg | ctcaaatcgt | tcacaaacgt | ggtgacatca | tcctggttgt | tgataatacc | 720 |
| ttcatgtctg | cgtactttca | gcgtccgctg | gcgctgggcg | ctgacatctg | catgtgctcc | 780 |
| gcgaccaaat | acatgaacgg | tcactctgac | gtagttatgg | gtctggttag | cgttaacagc | 840 |
| gacgatctca | attcccgcct | gcgtttcctg | cagaactccc | tcggcgcagt | accgtccccg | 900 |
| ttcgactgct | atctctgctg | ccgtggtctc | aaaacgctgc | aggttcgtat | ggaaaagcat | 960 |
| ttcaagaacg | gtatggcggt | ggcgcgcttc | ctcgaaacga | acccgcgtgt | gaaaaagtt | 1020 |
| gtttaccctg | gcctcccgtc | ccacccgcag | cacgaactgg | cgaaacgtca | gtgctctggt | 1080 |
| tgccctggca | tggtttcctt | ctacatcaaa | ggtgccctcc | agcacgcgaa | agccttcctg | 1140 |
| aaaaacctga | aactgttcac | cctcgcggtt | tctctgggtg | gttacgaatc | tctcgctgaa | 1200 |
| ctgccggcga | tcatgaccca | cgcttctgta | cctgaaaaag | accgtgcgac | cctcggtatc | 1260 |
| aacgataccc | tgatccgtct | gtctgttggt | ctggaggacg | aacaggacct | gctggaagac | 1320 |
| ctggatcgtg | ctctcaaagc | ggcgcacccg | agcggtggtg | gtggtagtgg | tggcggtggt | 1380 |
| atggcgaccc | gtggtaccgt | tactgatttc | ccgggtttcg | acggtcgtgc | ggacgcggaa | 1440 |

```
gttctgcgta aagcgatgaa aggcctgggt acggatgaag attctatcct gaacctgctg  1500
acgtctcgtt ctaacgcgca acgccaggaa atcgcgcagg agttcaaaac gctgtttggc  1560
cgcgacctgg tggacgacct caagtccgag ctgaccggta aattcgaaaa actgattgtt  1620
gccatgatga agccgtcccg tctgtatgac gcgtacgagc tcaagcatgc gctgaaaggt  1680
gctggcaccg acgaaaaggt tctgaccgag atcatcgcct ctcgtacccc ggaagaactg  1740
tctgcgatta aacaggttta cgaggaagaa tacggttcta atctggagga cgacgtggtc  1800
ggcgatactt ctggttacta tcagcgtatg ctcgttgtcc tgctccaggc caatcgtgat  1860
ccggacactg cgatcgacga tgcgcaagtt gagctggacg cacaggcgct cttccaggct  1920
ggtgaactga aatggggcac ggacgaggag aagttcatca ccatcttcgg cacgcgttct  1980
gttagccacc tgcgtcgtgt tttcgacaaa tacatgacca tctctggctt tcagatcgaa  2040
gaaaccattg accgtgagac ctctggtaac ctggaacagc tgctgctggc ggttgttaaa  2100
tctatccgtt ctattccggc gtacctggcg gaaaccctgt actacgccat gaagggtgcg  2160
ggcactgacg atcacaccct gattcgtgtt gttgtttctc gctccagat tgatctcttc  2220 aatatccgta aggaatttcg taaaaacttt gcgacttccc tctactctat gatcaaaggc  2280
gacactagcg gcgactacaa aaaagcgctg ctcctgctgt gcggtggtga agacgactga  2340
```

UNITED STATES PATENT AND TRADEMARK OFFICE
CERTIFICATE OF CORRECTION

PATENT NO. : 9,987,241 B2
APPLICATION NO. : 14/865650
DATED : June 5, 2018
INVENTOR(S) : Roger G. Harrison, Jr. and John J. Krais Page 1 of 1

It is certified that error appears in the above-identified patent and that said Letters Patent is hereby corrected as shown below:

In the Specification

Column 9, Line 48: Delete "Factor II/II," and replace with -- Factor II/IIa, --
Column 9, Line 49: Delete "Factor VIII/IIIa," and replace with -- Factor VIII/VIIIa, --

In the Claims

Column 62, Line 44: Before "95%" delete "94%"

Signed and Sealed this
Twenty-fourth Day of July, 2018

Andrei Iancu
*Director of the United States Patent and Trademark Office*